United States Patent
Tyler et al.

(10) Patent No.: US 9,042,201 B2
(45) Date of Patent: May 26, 2015

(54) METHOD AND SYSTEM FOR DIRECT COMMUNICATION

(71) Applicants: William J. Tyler, Roanoke, VA (US); Isy Goldwasser, Los Gatos, CA (US); Robert Muratore, Huntington, NY (US); Sumon Pal, Boston, MA (US); Tomo Sato, Roanoke, VA (US); Daniel Z. Wetmore, San Francisco, CA (US)

(72) Inventors: William J. Tyler, Roanoke, VA (US); Isy Goldwasser, Los Gatos, CA (US); Robert Muratore, Huntington, NY (US); Sumon Pal, Boston, MA (US); Tomo Sato, Roanoke, VA (US); Daniel Z. Wetmore, San Francisco, CA (US)

(73) Assignee: Thync, Inc., Los Gatos, CA (US)

( * ) Notice: Subject to any disclaimer, the term of this patent is extended or adjusted under 35 U.S.C. 154(b) by 198 days.

(21) Appl. No.: 13/657,401

(22) Filed: Oct. 22, 2012

(65) Prior Publication Data
US 2014/0211593 A1 Jul. 31, 2014

Related U.S. Application Data

(60) Provisional application No. 61/550,334, filed on Oct. 21, 2011.

(51) Int. Cl.
*H04B 11/00* (2006.01)
*A61B 5/0476* (2006.01)
*G06F 3/01* (2006.01)
*A61B 5/16* (2006.01)

(52) U.S. Cl.
CPC ............. *H04B 11/00* (2013.01); *A61B 5/0476* (2013.01); *A61B 5/165* (2013.01); *G06F 3/015* (2013.01)

(58) Field of Classification Search
CPC ...... A61B 5/0476; A61B 5/165; G06F 3/015; H04B 11/00; A61N 2/02; A61N 2/004; A61N 2/006; A61N 2/008; A61N 1/05; A61N 1/372; A61N 1/36; A61N 1/3605; A61N 1/0529
USPC .................... 367/139, 137; 600/9–15; 607/45
See application file for complete search history.

(56) References Cited

U.S. PATENT DOCUMENTS

| | | | |
|---|---|---|---|
| 4,002,221 A | 1/1977 | Buchalter |
| 4,059,098 A | 11/1977 | Murdock |
| 4,556,066 A | 12/1985 | Semrow |
| 4,646,744 A | 3/1987 | Capel |
| 4,723,552 A | 2/1988 | Kenyon et al. |
| 4,886,068 A | 12/1989 | Kaneko et al. |
| 5,127,410 A | 7/1992 | King et al. |
| 5,394,877 A | 3/1995 | Orr et al. |
| 5,413,550 A | 5/1995 | Castel |

(Continued)

FOREIGN PATENT DOCUMENTS

| | | |
|---|---|---|
| CN | 101288600 A | 10/2008 |
| JP | S 62-35906 U | 3/1987 |

(Continued)

OTHER PUBLICATIONS

U.S. Appl. No. 14/025,586, filed Sep. 12, 2013, Tyler et al.

(Continued)

*Primary Examiner* — Daniel Pihulic
(74) *Attorney, Agent, or Firm* — Wilson Sonsini Goodrich & Rosati

(57) ABSTRACT

Information is communicated to an individual by directing an acoustic signal transcranially to a target region in the brain. The target region is stimulated to produce a cognitive effect, and the cognitive effect is modulated or encoded to carry the desired information.

28 Claims, 11 Drawing Sheets bioTU communication framework

(56) References Cited

U.S. PATENT DOCUMENTS

| | | |
|---|---|---|
| 5,476,438 A | 12/1995 | Edrich et al. |
| 5,494,038 A | 2/1996 | Wang et al. |
| 5,505,205 A | 4/1996 | Solomon et al. |
| 5,520,612 A | 5/1996 | Winder et al. |
| 5,522,878 A | 6/1996 | Montecalvo et al. |
| 5,540,736 A | 7/1996 | Haimovich et al. |
| 5,558,092 A | 9/1996 | Unger et al. |
| 5,752,924 A | 5/1998 | Kaufman et al. |
| 5,782,767 A | 7/1998 | Pretlow, III |
| 5,951,476 A | 9/1999 | Beach |
| 6,039,694 A | 3/2000 | Larson et al. |
| 6,078,838 A | 6/2000 | Rubinstein |
| 6,182,341 B1 | 2/2001 | Talbot et al. |
| 6,394,969 B1 | 5/2002 | Lenhardt |
| 6,432,069 B1 | 8/2002 | Godo et al. |
| 6,478,754 B1 | 11/2002 | Babaev |
| 6,526,318 B1 | 2/2003 | Ansarinia |
| 6,536,440 B1 | 3/2003 | Dawson |
| 6,575,922 B1 | 6/2003 | Fearnside et al. |
| 6,584,357 B1 | 6/2003 | Dawson |
| 6,663,554 B2 | 12/2003 | Babaev |
| 6,729,337 B2 | 5/2004 | Dawson |
| 6,733,450 B1 | 5/2004 | Alexandrov et al. |
| 6,735,475 B1 | 5/2004 | Whitehurst et al. |
| 6,770,031 B2 | 8/2004 | Hynynen et al. |
| 6,846,290 B2 | 1/2005 | Lizzi et al. |
| 6,964,684 B2 | 11/2005 | Ortiz et al. |
| 6,978,179 B1 | 12/2005 | Flagg et al. |
| 7,104,947 B2 | 9/2006 | Riehl |
| 7,108,663 B2 | 9/2006 | Talish et al. |
| 7,190,998 B2 | 3/2007 | Shalev et al. |
| 7,283,861 B2 | 10/2007 | Bystritsky |
| 7,350,522 B2 | 4/2008 | Dawson |
| 7,363,076 B2 | 4/2008 | Yun et al. |
| 7,410,469 B1 | 8/2008 | Talish et al. |
| 7,429,248 B1 | 9/2008 | Winder et al. |
| 7,431,704 B2 | 10/2008 | Babaev |
| 7,510,536 B2 | 3/2009 | Foley et al. |
| 7,699,768 B2 | 4/2010 | Kishawi et al. |
| 7,699,778 B2 | 4/2010 | Adam |
| 7,713,218 B2 | 5/2010 | Babaev et al. |
| 7,914,470 B2 | 3/2011 | Babaev |
| 7,974,845 B2 | 7/2011 | Spiridigliozzi et al. |
| 8,123,707 B2 | 2/2012 | Huckle et al. |
| 8,150,537 B2 | 4/2012 | Tanaka et al. |
| 8,190,248 B2 | 5/2012 | Besio et al. |
| 8,235,919 B2 | 8/2012 | Babaev |
| 8,239,030 B1 | 8/2012 | Hagedorn et al. |
| 8,591,419 B2 | 11/2013 | Tyler |
| 8,858,440 B2 | 10/2014 | Tyler |
| 2001/0040214 A1 | 11/2001 | Friedman et al. |
| 2002/0042574 A1 | 4/2002 | Manor et al. |
| 2002/0173697 A1 | 11/2002 | Lenhardt |
| 2003/0009153 A1 | 1/2003 | Brisken et al. |
| 2003/0032900 A1 | 2/2003 | Ella |
| 2003/0204135 A1 | 10/2003 | Bystritsky |
| 2004/0049134 A1 | 3/2004 | Tosaya et al. |
| 2004/0059241 A1 | 3/2004 | Suffin |
| 2004/0082857 A1 | 4/2004 | Schonenberger et al. |
| 2004/0249416 A1 | 12/2004 | Yun et al. |
| 2004/0254469 A1 | 12/2004 | Shkarlet et al. |
| 2004/0267118 A1 | 12/2004 | Dawson |
| 2005/0033140 A1 | 2/2005 | De la Rosa et al. |
| 2005/0085748 A1 | 4/2005 | Culp et al. |
| 2005/0249667 A1 | 11/2005 | Tuszynski et al. |
| 2005/0277824 A1 | 12/2005 | Aubry et al. |
| 2006/0058678 A1 | 3/2006 | Vitek et al. |
| 2006/0074355 A1 | 4/2006 | Slayton et al. |
| 2006/0111754 A1 | 5/2006 | Rezai et al. |
| 2006/0173321 A1 | 8/2006 | Kubota et al. |
| 2006/0184070 A1 | 8/2006 | Hansmann et al. |
| 2006/0201090 A1 | 9/2006 | Guevara et al. |
| 2007/0016041 A1 | 1/2007 | Nita |
| 2007/0043401 A1 | 2/2007 | John |
| 2007/0173902 A1 | 7/2007 | Maschino et al. |
| 2007/0179557 A1 | 8/2007 | Maschino et al. |
| 2007/0255085 A1 | 11/2007 | Kishawi et al. |
| 2007/0299370 A1 | 12/2007 | Bystritsky |
| 2008/0033297 A1 | 2/2008 | Sliwa |
| 2008/0045882 A1 | 2/2008 | Finsterwald |
| 2008/0154332 A1 | 6/2008 | Rezai |
| 2008/0194967 A1 | 8/2008 | Sliwa et al. |
| 2008/0200810 A1 | 8/2008 | Buchalter |
| 2008/0319376 A1 | 12/2008 | Wilcox et al. |
| 2009/0012577 A1 | 1/2009 | Rezai et al. |
| 2009/0024189 A1 | 1/2009 | Lee et al. |
| 2009/0099482 A1 | 4/2009 | Furuhata |
| 2009/0099483 A1 | 4/2009 | Rybyanets |
| 2009/0105581 A1 | 4/2009 | Widenhorn |
| 2009/0112133 A1 | 4/2009 | Deisseroth et al. |
| 2009/0114849 A1 | 5/2009 | Schneider et al. |
| 2009/0149782 A1 | 6/2009 | Cohen |
| 2009/0163964 A1 | 6/2009 | Boyden et al. |
| 2009/0221902 A1 | 9/2009 | Myhr |
| 2009/0276005 A1 | 11/2009 | Pless |
| 2010/0016707 A1 | 1/2010 | Awara et al. |
| 2010/0022889 A1 | 1/2010 | Caberg et al. |
| 2010/0030299 A1 | 2/2010 | Covalin |
| 2010/0087698 A1 | 4/2010 | Hoffman |
| 2010/0125207 A1 | 5/2010 | Kim et al. |
| 2010/0145215 A1 | 6/2010 | Pradeep et al. |
| 2010/0234728 A1 | 9/2010 | Foley et al. |
| 2010/0324440 A1 | 12/2010 | Moore et al. |
| 2011/0009734 A1 | 1/2011 | Foley et al. |
| 2011/0040171 A1 | 2/2011 | Foley et al. |
| 2011/0040190 A1 | 2/2011 | Jahnke et al. |
| 2011/0082326 A1 | 4/2011 | Mishelevich et al. |
| 2011/0092800 A1 | 4/2011 | Yoo et al. |
| 2011/0112394 A1 | 5/2011 | Mishelevich |
| 2011/0130615 A1 | 6/2011 | Mishelevich |
| 2011/0144716 A1 | 6/2011 | Bikson et al. |
| 2011/0178441 A1 | 7/2011 | Tyler |
| 2011/0178442 A1 | 7/2011 | Mishelevich |
| 2011/0190668 A1 | 8/2011 | Mishelevich |
| 2011/0196267 A1 | 8/2011 | Mishelevich |
| 2011/0208094 A1 | 8/2011 | Mishelevich |
| 2011/0213200 A1 | 9/2011 | Mishelevich |
| 2011/0270138 A1 | 11/2011 | Mishelevich |
| 2011/0288610 A1 | 11/2011 | Brocke |
| 2012/0029393 A1 | 2/2012 | Lee |
| 2012/0053391 A1 | 3/2012 | Mishelevich |
| 2012/0083719 A1 | 4/2012 | Mishelevich |
| 2012/0197163 A1 | 8/2012 | Mishelevich |
| 2012/0209346 A1 | 8/2012 | Bikson et al. |
| 2012/0245653 A1 | 9/2012 | Bikson et al. |
| 2012/0265261 A1 | 10/2012 | Bikson et al. |
| 2012/0283502 A1 | 11/2012 | Mishelevich |
| 2012/0289869 A1 | 11/2012 | Tyler |
| 2013/0066239 A1 | 3/2013 | Mishelevich |
| 2013/0066350 A1 | 3/2013 | Mishelevich |
| 2013/0144192 A1 | 6/2013 | Mishelevich |
| 2014/0094720 A1 | 4/2014 | Tyler et al. |
| 2014/0194726 A1* | 7/2014 | Mishelevich et al. ............ 601/2 |
| 2014/0211593 A1* | 7/2014 | Tyler et al. .................... 367/137 |
| 2015/0025422 A1 | 1/2015 | Tyler et al. |

FOREIGN PATENT DOCUMENTS

| | | |
|---|---|---|
| JP | H 11290368 A | 10/1999 |
| JP | 2000-040191 A | 2/2000 |
| JP | 2001-327495 A | 11/2001 |
| JP | 2006-195872 A | 7/2006 |
| JP | 2006192181 | 7/2006 |
| JP | 2007-517534 | 7/2007 |
| WO | WO 98/07367 A1 | 2/1998 |
| WO | WO 2005/122933 A1 | 12/2005 |
| WO | WO 2006/026459 A2 | 3/2006 |
| WO | WO 2007/130308 A2 | 11/2007 |
| WO | WO 2007/130308 A3 | 1/2008 |
| WO | WO 2008/017998 A2 | 2/2008 |
| WO | WO 2008/089003 A2 | 7/2008 |
| WO | WO 2008/089003 A3 | 9/2008 |
| WO | WO 2009/017264 A1 | 2/2009 |
| WO | WO 2006/026459 A3 | 4/2009 |

(56) References Cited

FOREIGN PATENT DOCUMENTS

| WO | WO 2010/009141 A1 | 1/2010 | | |
|---|---|---|---|---|
| WO | WO 2010/120823 A2 | 10/2010 | | |
| WO | WO 2011/057028 A1 | 5/2011 | | |
| WO | WO/2013/059833 | * | 4/2013 | ........... A61B 5/0476 |

OTHER PUBLICATIONS

European search report and opinion dated Mar. 18, 2013 for EP Application No. 10829128.7.
International search report and written opinion dated Jul. 24, 2013 for PCT Application No. US2013/035014.
International search report and written opinion dated Oct. 8, 2013 for PCT Application No. US2013/047174.
Office action dated Oct. 22, 2013 for U.S. Appl. No. 13/426,424.
Office action dated Oct. 22, 2013 for U.S. Appl. No. 13/551,420.
Office action dated Oct. 28, 2013 for U.S. Appl. No. 13/426,424.
Office action dated Oct. 28, 2013 for U.S. Appl. No. 13/551,420.
International search report and written opinion dated Dec. 2, 2013 for PCT Application No. US2013/057131.
Office action dated Apr. 11, 2014 for U.S. Appl. No. 14/025,586.
U.S. Appl. No. 13/718,245, filed Dec. 18, 2013, Mishelevich.
U.S. Appl. No. 13/734,216, filed Jan. 4, 2013, Mishelevich.
Additional figures for cog enhancement NPA. Jan. 1, 2013.
Boddaert, et al. Autism: functional brain mapping of exceptional calendar capacity. Br J Psychiatry. Jul. 2005;187:83-6.
ClinicalTrials. Deep brain stimulation (DBS) for treatment resistant bipolar disorder. Oct. 2012. www.clinicaltrials.gov. Accessed Dec. 17, 2012.
Fleury, et al. New piezocomposite transducers for therapeutic ultrasound. 2nd International Symposium on Therapeutic Ultrasound—Seattle—Jul. 31-Feb. 8, 2002.
International search report and written opinion dated Feb. 14, 2013 for PCT/US2012/061396.
Mayo Clinic staff. Bipolar disorder: treatments drugs. Mayo Clinic. Aug. 2012. www.mayoclinic.com. Accessed Dec. 17, 2012.
Mendelsohn, et al. Neurosurgeons' perspectives on psychosurgery and neuroenhancement: a qualitative study at one center. J Neurosurg. Dec. 2010;113(6):1212-8. doi: 10.3171/2010.5.JNS091896. Epub Jun. 4, 2010.
Miller, et al. Assessment tools for adult bipolar disorder. Clin Psychol (New York). Jun. 1, 2009;16(2):188-201.
Miller, et al. Enhanced artistic creativity with temporal lobe degeneration. Lancet. Dec. 21-28, 1996;348(9043):1744-5.
Office action dated Jan. 31, 2013 for U.S. Appl. No. 13/200,903.
Office action dated Feb. 14, 2013 for U.S. Appl. No. 12/940,052.
Office action dated Feb. 14, 2013 for U.S. Appl. No. 13/252,054.
Office action dated Feb. 19, 2013 for U.S. Appl. No. 13/031,192.
Office action dated Feb. 26, 2013 for U.S. Appl. No. 13/007,626.
Office action dated May 25, 2012 for U.S. Appl. No. 13/031,192.
Office action dated Jun. 5, 2012 for U.S. Appl. No. 13/020,016.
Office action dated Jun. 5, 2012 for U.S. Appl. No. 13/021,785.
Office action dated Jun. 6, 2012 for U.S. Appl. No. 13/252,054.
Office action dated Jun. 8, 2012 for U.S. Appl. No. 12/940,052.
Office action dated Jun. 14, 2012 for U.S. Appl. No. 13/098,473.
Office action dated Aug. 20, 2012 for U.S. Appl. No. 13/003,853.
Office action dated Sep. 27, 2012 for U.S. Appl. No. 13/007,626.
Office action dated Oct. 16, 2012 for U.S. Appl. No. 13/020,016.
Office action dated Nov. 20, 2012 for U.S. Appl. No. 13/021,785.
Patoine. Deep brain stimulation for severe depression: new results suggest it works, but how? Dana Foundation. Mar. 2012. www.dana.org/media/detail.aspx?id=35782. Accessed Dec. 17, 2012.
Shirvalkar, et al. Cognitive enhancement with central thalamic electrical stimulation. Proc Natl Acad Sci U S A. Nov. 7, 2006;103(45):17007-12. Epub Oct. 25, 2006.
Snyder, et al. Concept formation: 'object' attributes dynamically inhibited from conscious awareness. J Integr Neurosci. Mar. 2004;3(1):31-46.
Snyder, et al. Savant-like skills exposed in normal people by suppressing the left fronto-temporal lobe. J Integr Neurosci. Dec. 2003;2(2):149-58.
U.S. Appl. No. 13/551,420, filed Jul. 17, 2012, Mishelevich.
U.S. Appl. No. 13/625,677, filed Sep. 24, 2012, Mishelevich.
U.S. Appl. No. 13/689,178, filed Nov. 29, 2012, Mishelevich.
Arroyo, et al. Mirth, laughter and gelastic seizures. Brain. Aug. 1993;116 ( Pt 4):757-80.
Bachtold, et al. Focused ultrasound modifications of neural circuit activity in a mammalian brain. Ultrasound Med Biol. May 1998;24(4):557-65.
Baker, et al. Deep brain stimulation for obsessive-compulsive disorder: using functional magnetic resonance imaging and electrophysiological techniques: technical case report. Neurosurgery. Nov. 2007;61(5 Suppl 2):E367-8; discussion E368.
Bartsch, et al. Stimulation of the greater occipital nerve induces increased central excitability of dural afferent input. Brain. Jul. 2002;125(Pt 7):1496-509.
Breneman, et al. Piezo- and Flexoelectric Membrane Materials Underlie Fast Biological Motors in the Ear. Mater Res Soc Symp Proc. 2009 Spring;1186E. pii: 1186-JJ06-04.
Burns, et al. Treatment of medically intractable cluster headache by occipital nerve stimulation: long-term follow-up of eight patients. Lancet. Mar. 31, 2007;369(9567):1099-106.
Bystritsky, et al. A review of low-intensity focused ultrasound pulsation. Brain Stimul. Jul. 2011;4(3):125-36. Epub Apr. 1, 2011.
Clarke, et al. Transcranial magnetic stimulation for migraine: clinical effects. J Headache Pain. Oct. 2006;7(5):341-6. Epub Oct. 25, 2006.
Clement, et al. A non-invasive method for focusing ultrasound through the human skull. Phys Med Biol. Apr. 21, 2002;47(8):1219-36.
Dalecki. Mechanical bioeffects of ultrasound. Annu Rev Biomed Eng. 2004;6:229-48.
European search report and opinion dated Oct. 19, 2011 for EP Application No. 09798662.4.
Farrell, et al. Study of the human visual cortex: direct cortical evoked potentials and stimulation. J Clin Neurophysiol. Feb. 2007;24(1):1-10.
Feurra, et al. Frequency specific modulation of human somatosensory cortex. Front Psychol. 2011;2:13. Epub Feb. 2, 2011.
Gavrilov, et al. Application of focused ultrasound for the stimulation of neural structures. Ultrasound Med Biol. 1996;22(2):179-92.
Gavrilov, et al. The effect of focused ultrasound on the skin and deep nerve structures of man and animal. Prog Brain Res. 1976;43:279-92.
George, et al. Changes in mood and hormone levels after rapid-rate transcranial magnetic stimulation (rTMS) of the prefrontal cortex. J Neuropsychiatry Clin Neurosci. 1996 Spring;8(2):172-80.
George, et al. Daily repetitive transcranial magnetic stimulation (rTMS) improves mood in depression. Neuroreport. Oct. 2, 1995;6(14):1853-6.
George, et al. Vagus nerve stimulation: a new tool for brain research and therapy. Biol Psychiatry. Feb. 15, 2000;47(4):287-95.
Ghanam, et al. Vagal nerve stimulator implantation: an otolaryngologist's perspective. Otolaryngol Head Neck Surg. Jul. 2006;135(1):46-51.
Griesbauer, et al. Wave propagation in lipid monolayers. Biophys J. Nov. 18, 2009;97(10):2710-6.
Hauptman, et al. Potential surgical targets for deep brain stimulation in treatment-resistant depression. Neurosurg Focus. 2008;25(1):E3.
Heimburg. Lipid ion channels. Biophys Chem. Aug. 2010;150(1-3):2-22. Epub Mar. 11, 2010.
Hynynen, et al. 500-element ultrasound phased array system for noninvasive focal surgery of the brain: a preliminary rabbit study with ex vivo human skulls. Magn Reson Med. Jul. 2004;52(1):100-7.
Hynynen, et al. Clinical applications of focused ultrasound-the brain. Int J Hyperthermia. Mar. 2007;23(2):193-202.
Hynynen, et al. Demonstration of potential noninvasive ultrasound brain therapy through an intact skull. Ultrasound Med Biol. Feb. 1998;24(2):275-83.
International search report and written opinion dated Mar. 14, 2011 for PCT/US2010/055527.
International search report and written opinion dated Sep. 10, 2009 for PCT/US2009/050560.

(56) References Cited

OTHER PUBLICATIONS

Johansen-Berg, et al. Anatomical connectivity of the subgenual cingulate region targeted with deep brain stimulation for treatment-resistant depression. Cereb Cortex. Jun. 2008;18(6):1374-83. Epub Oct. 10, 2007.
Komisaruk, et al. Brain activation during vaginocervical self-stimulation and orgasm in women with complete spinal cord injury: fMRI evidence of mediation by the vagus nerves. Brain Res. Oct. 22, 2004;1024(1-2):77-88.
Komisaruk, et al. Functional MRI of the brain during orgasm in women. Annu Rev Sex Res. 2005;16:62-86.
Lee, et al. Neural correlates of affective processing in response to sad and angry facial stimuli in patients with major depressive disorder. Prog Neuropsychopharmacol Biol Psychiatry. Apr. 1, 2008;32(3):778-85. Epub Dec. 23, 2007.
Lee, et al. The neural substrates of affective processing toward positive and negative affective pictures in patients with major depressive disorder. Prog Neuropsychopharmacol Biol Psychiatry. Oct. 1, 2007;31(7):1487-92. Epub Jul. 5, 2007.
Lipton, et al. Single-pulse transcranial magnetic stimulation for acute treatment of migraine with aura: a randomised, double-blind, parallel-group, sham-controlled trial. Lancet Neurology. 2010; 9(4):373-380. doi:10.1016/S1474-4422(10)70054-5.
Mayberg, et al. Deep brain stimulation for treatment-resistant depression. Neuron. Mar. 3, 2005;45(5):651-60.
Meloy, et al. Neurally augmented sexual function in human females: a preliminary investigation. Neuromodulation. Jan. 2006;9(1):34-40. doi: 10.1111/j.1525-1403.2006.00040.x.
Menkes, et al. Right frontal lobe slow frequency repetitive transcranial magnetic stimulation (SF r-TMS) is an effective treatment for depression: a case-control pilot study of safety and efficacy. J Neurol Neurosurg Psychiatry. Jul. 1999;67(1):113-5.
Mihran, et al. Temporally-specific modification of myelinated axon excitability in vitro following a single ultrasound pulse. Ultrasound Med Biol. 1990; 16(3):297-309.
Milad, et al. The role of the orbitofrontal cortex in anxiety disorders. Ann N Y Acad Sci. Dec. 2007;1121:546-61. Epub Aug. 14, 2007.
Morris, et al. Lipid Stress at Play: Mechanosensitivity of Voltage-Gated Channels. Current Topics in Membranes. 2007; 59:297-338.
Morris, et al. Nav channel mechanosensitivity: activation and inactivation accelerate reversibly with stretch. Biophys J. Aug. 1, 2007;93(3):822-33. Epub May 11, 2007.
Muehlberger, et al. Lasting outcome of the surgical treatment of migraine headaches—a four year follow-up. Meeting of the American Society of Plastic Surgery. Abstract #14728 Nov. 3, 2008.
Nakao, et al. Working memory dysfunction in obsessive-compulsive disorder: a neuropsychological and functional MRI study. J Psychiatr Res. May 2009;43(8):784-91. Epub Dec. 10, 2008.
Nitsche, et al. Excitability changes induced in the human motor cortex by weak transcranial direct current stimulation. J Physiol. Sep. 15, 2000;527 Pt 3:633-9.
Norton. Can ultrasound be used to stimulate nerve tissue? Biomed Eng Online. Mar. 4, 2003;2:6.
O'Brien. Ultrasound-biophysics mechanisms. Prog Biophys Mol Biol. Jan.-Apr. 2007;93(1-3):212-55. Epub Aug. 8, 2006.
Petrov, et al. Flexoelectric effects in model and native membranes containing ion channels. Eur Biophys J. 1993;22(4):289-300.
Reiman, et al. Neuroanatomical correlates of a lactate-induced anxiety attack. Arch Gen Psychiatry. Jun. 1989;46(6):493-500.
Rinaldi, et al. Modification by focused ultrasound pulses of electrically evoked responses from an in vitro hippocampal preparation. Brain Res. Aug. 30, 1991;558(1):36-42.
Sailer, et al. Effects of peripheral sensory input on cortical inhibition in humans. J Physiol. Oct. 15, 2002;544(Pt 2):617-29.
Satow, et al. Mirth and laughter arising from human temporal cortex. J Neurol Neurosurg Psychiatry. Jul. 2003;74(7):1004-5.
Schienle, et al. Symptom provocation and reduction in patients suffering from spider phobia: an fMRI study on exposure therapy. Eur Arch Psychiatry Clin Neurosci. Dec. 2007;257(8):486-93. Epub Sep. 27, 2007.
Shealy, et al. Reversible effects of ultrasound on spinal reflexes. Arch Neurol. May 1962;6:374-86.
Sperli, et al. Contralateral smile and laughter, but no mirth, induced by electrical stimulation of the cingulate cortex. Epilepsia. Feb. 2006;47(2):440-3.
Sukharev, et al. Mechanosensitive channels: multiplicity of families and gating paradigms. Sci STKE. Feb. 3, 2004;2004(219):re4.
Ter Haar. Therapeutic applications of ultrasound. Prog Biophys Mol Biol. Jan.-Apr. 2007;93(1-3):111-29. Epub Aug. 4, 2006.
Tsui, et al. In vitro effects of ultrasound with different energies on the conduction properties of neural tissue. Ultrasonics. Jun. 2005;43(7):560-5. Epub Dec. 18, 2004.
Tufail, et al. Transcranial pulsed ultrasound stimulates intact brain circuits. Neuron. Jun. 10, 2010;66(5):681-94.
Tufail, et al. Ultrasonic neuromodulation by brain stimulation with transcranial ultrasound. Nat Protoc. Sep. 1, 2011;6(9):1453-70. doi: 10.1038/nprot.2011.371.
Tyler, et al. Remote excitation of neuronal circuits using low-intensity, low-frequency ultrasound. PLoS One. 2008;3(10):e3511. Epub Oct. 29, 2008.
Velling, et al. Modulation of the functional state of the brain with the aid of focused ultrasonic action. Neurosci Behav Physiol. Sep.-Oct. 1988;18(5):369-75.
Yang, et al. Transcranial ultrasound stimulation: a possible therapeutic approach to epilepsy. Med Hypotheses. Mar. 2011;76(3):381-3. Epub Dec. 8, 2010.
Yoo, et al. Focused ultrasound modulates region-specific brain activity. Neuroimage. Jun. 1, 2011;56(3):1267-75. Epub Feb. 24, 2011.
Yoo, et al. Transcranial focused ultrasound to the thalamus alters anesthesia time in rats. Neuroreport. Oct. 26, 2011;22(15):783-7.
Yucel, et al. Anterior cingulate dysfunction: implications for psychiatric disorders? J Psychiatry Neurosci. Sep. 2003;28(5):350-4.
Zaehle, et al. Transcranial alternating current stimulation enhances individual alpha activity in human EEG. PLoS One. Nov. 1, 2010;5(11):e13766.
Zaghi, et al. Noninvasive brain stimulation with low-intensity electrical currents: putative mechanisms of action for direct and alternating current stimulation. Neuroscientist. Jun. 2010;16(3):285-307. Epub Dec. 29, 2009.
Zhao, et al. Altered default mode network activity in patient with anxiety disorders: an fMRI study. Eur J Radiol. Sep. 2007;63(3):373-8. Epub Apr. 2, 2007.
U.S. Appl. No. 14/460,007, filed Aug. 14, 2014, Tyler et al.
U.S. Appl. No. 14/501,523, filed Sep. 30, 2014, Tyler et al.
European search report and opinion dated Dec. 8, 2014 for EP Application No. 14182336.9.
U.S. Appl. No. 14/576,588, filed Dec. 19, 2014, Tyler et al.
U.S. Appl. No. 14/603,671, filed Jan. 23, 2015, Sato et al.
Dmochowski, et al. Optimized multi-electrode stimulation increases focality and intensity at target. J Neural Eng. Aug. 2011;8(4):046011. doi: 10.1088/1741-2560/8/4/046011. Epub Jun. 10, 2011.
Latikka, et al. Conductivity of living intracranial tissues. Phys Med Biol. Jun. 2001;46(6):1611-6.
Notice of allowance dated Jul. 1, 2013 for U.S. Appl. No. 13/003,853.
Notice of allowance dated Aug. 1, 2014 for U.S. Appl. No. 14/025,586.

\* cited by examiner

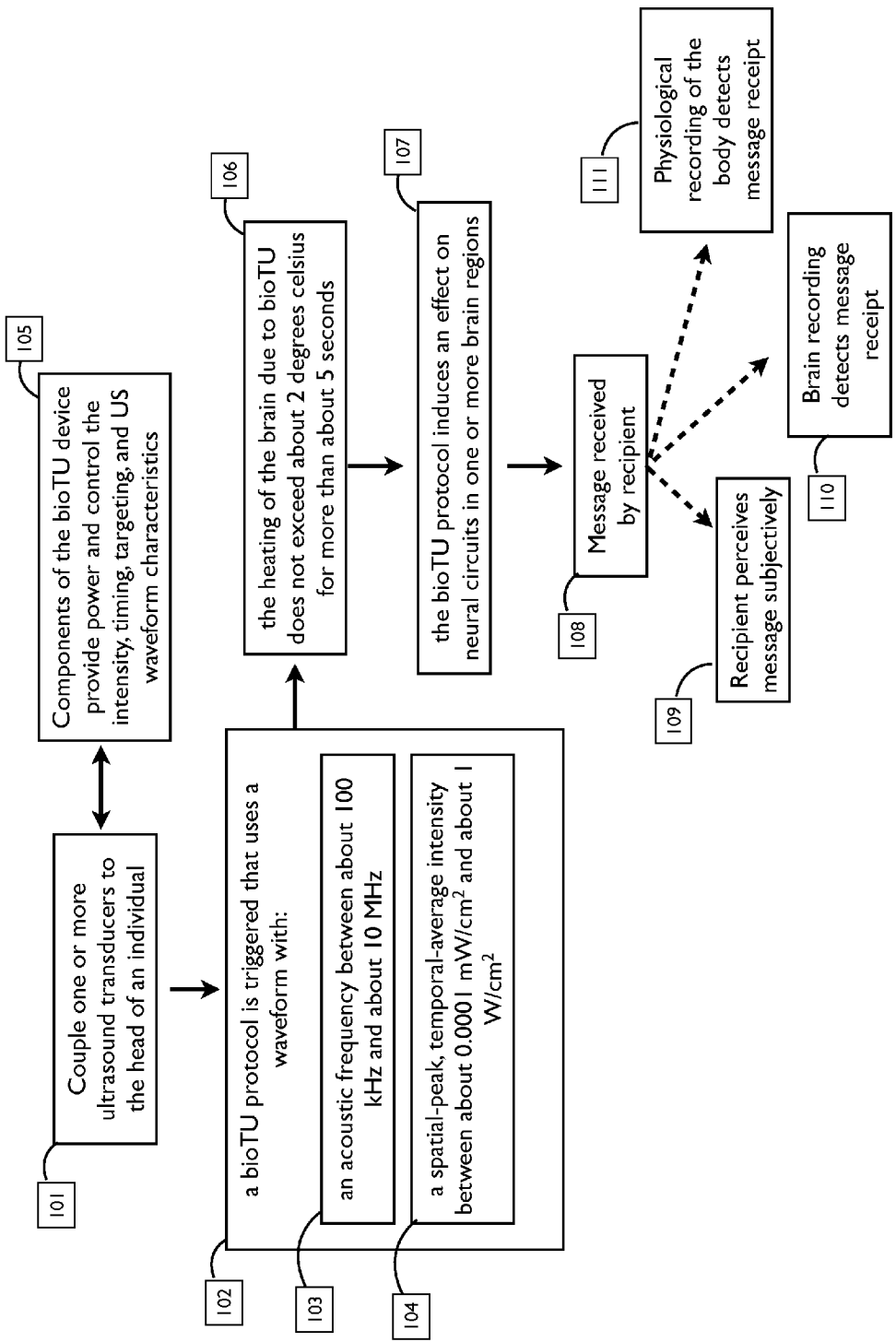
Figure 1. bioTU communication framework

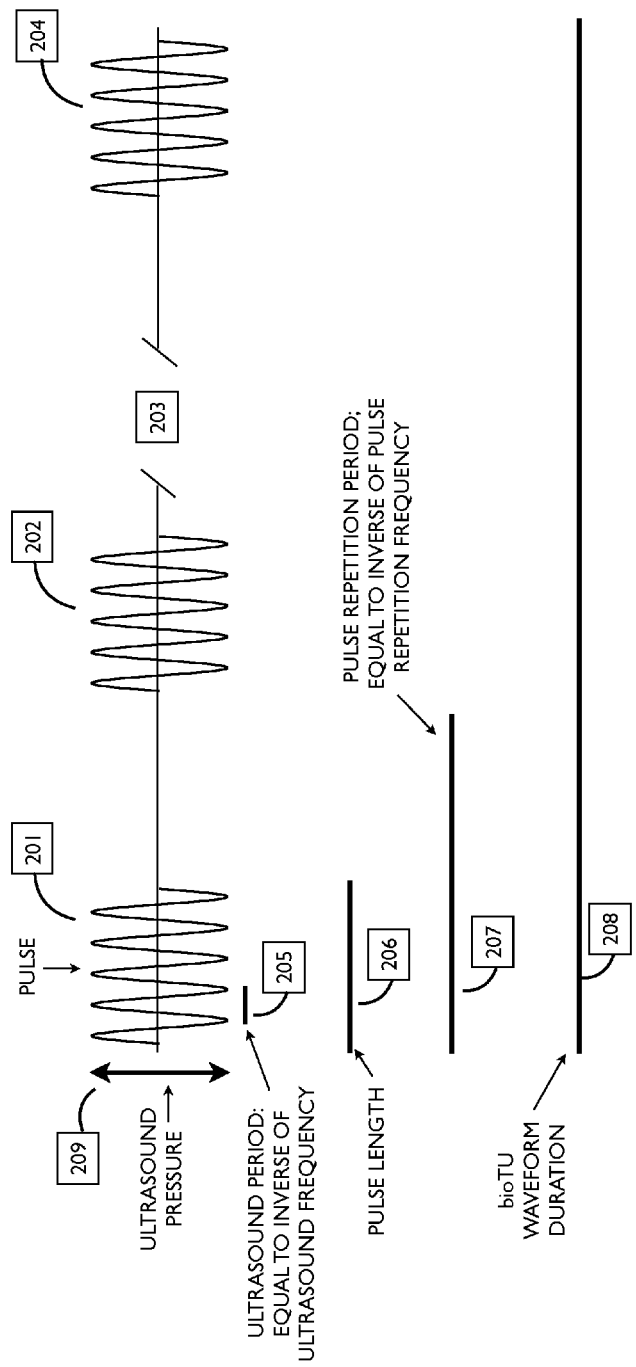
Figure 2. bioTU waveform, pulsed ultrasound protocol

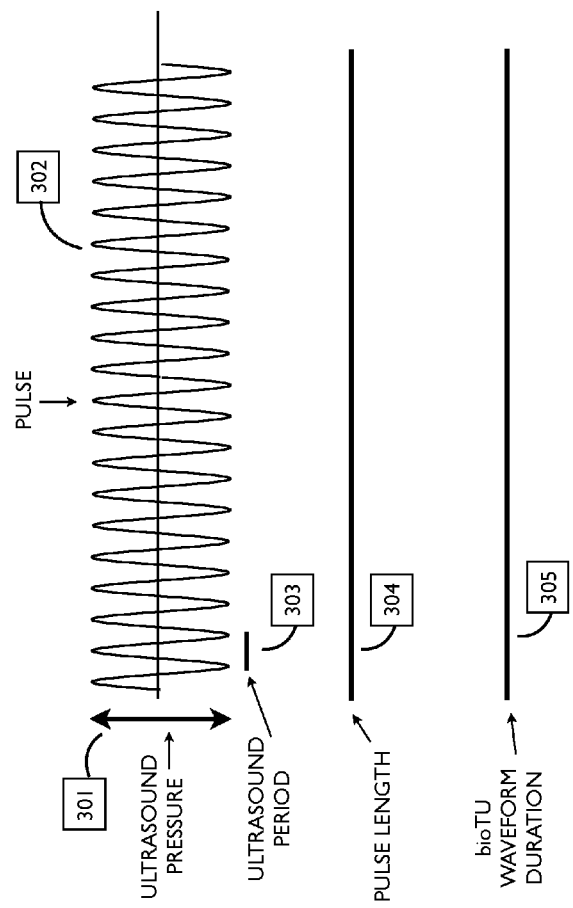
Figure 3. bioTU waveform, continuous wave ultrasound protocol

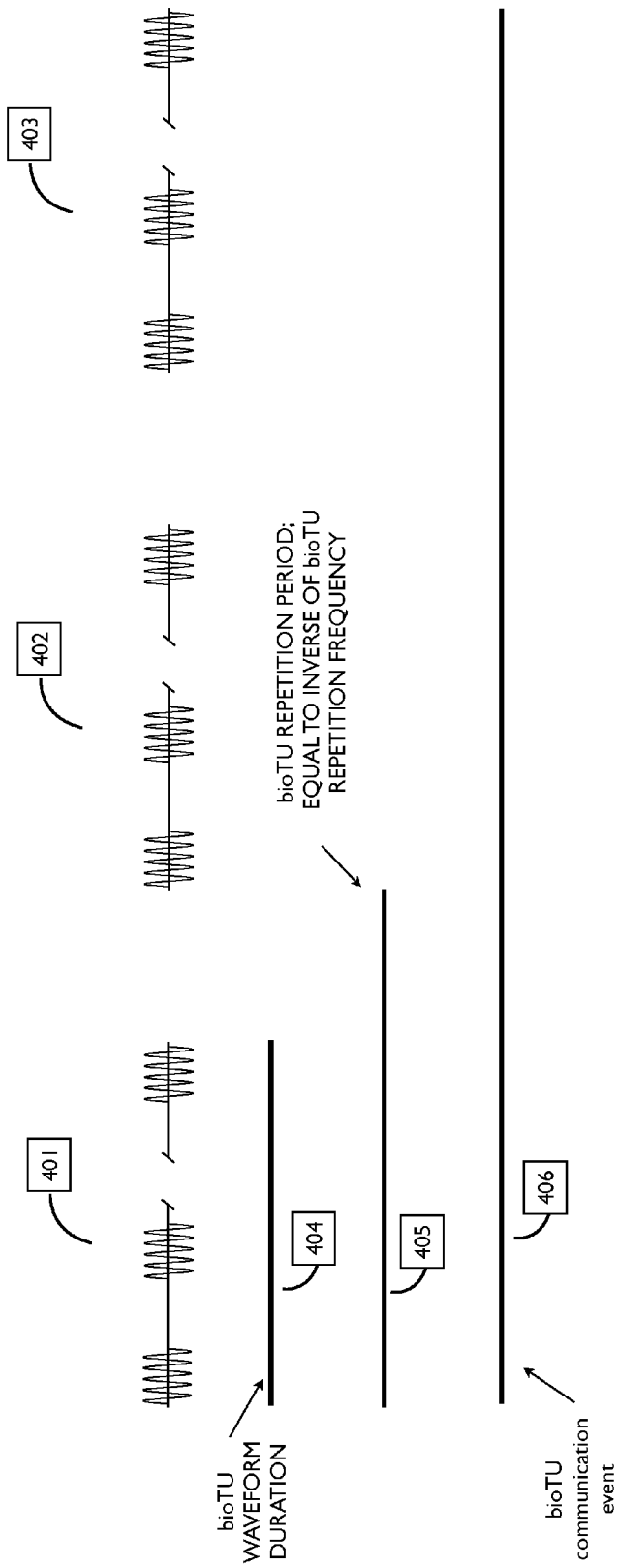
Figure 4. bioTU waveform repetition

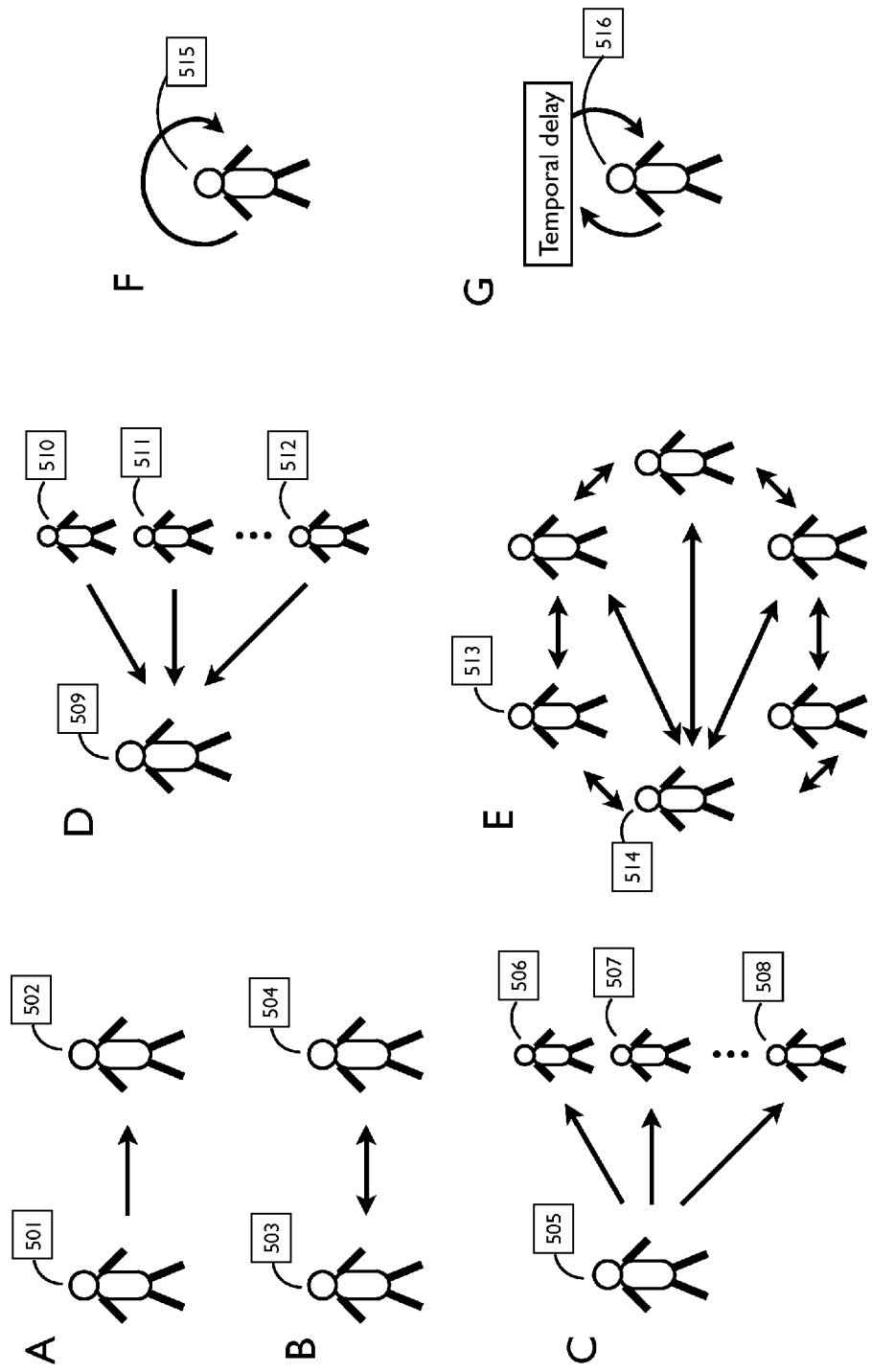
Figure 5. Routes and groups of communication

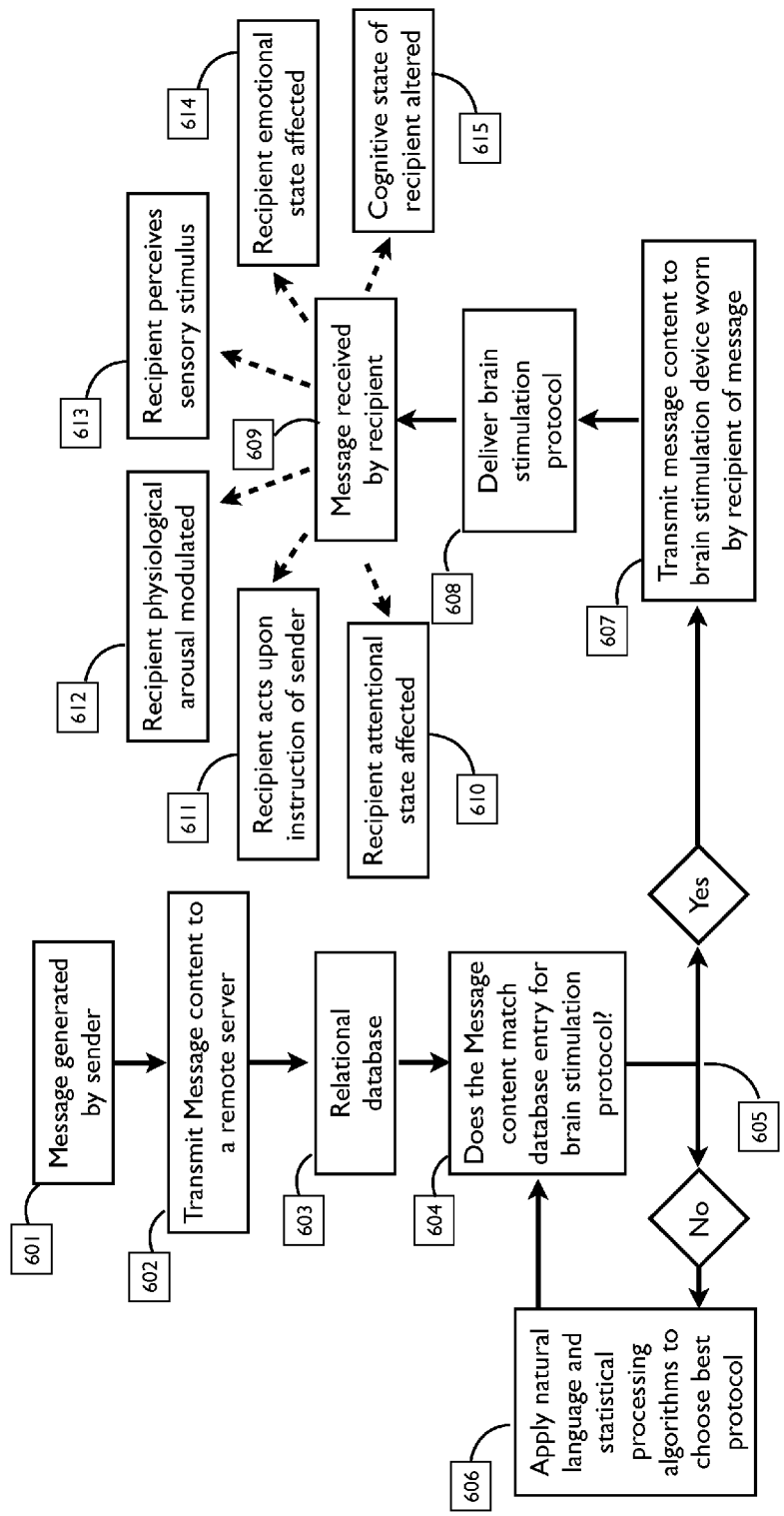
Figure 6. Data / process flow, simple version, one-way communication by brain stimulation

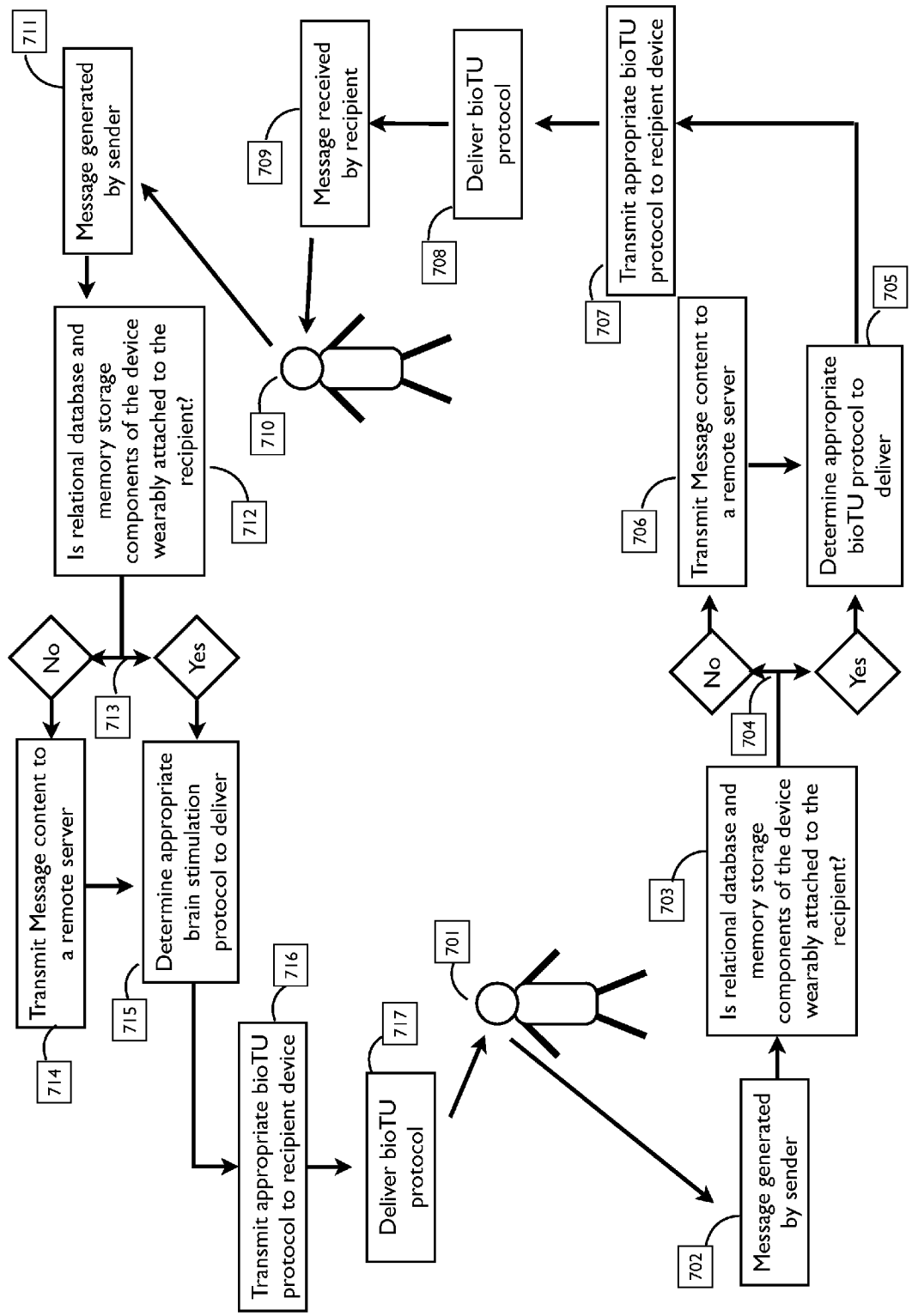
Figure 7. A conversation between two individuals via bioTU

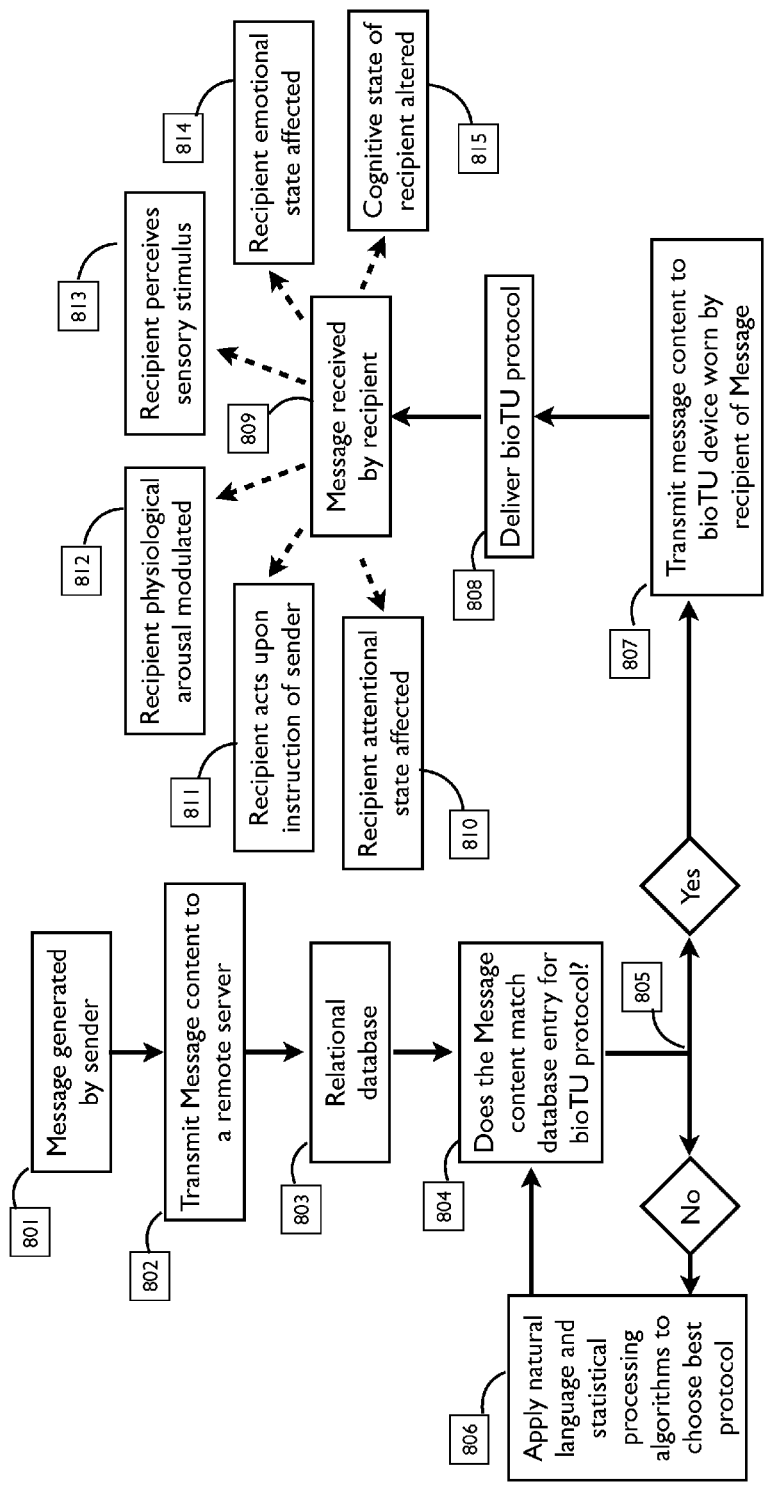
Figure 8. Data / process flow, one-way communication, bioTU

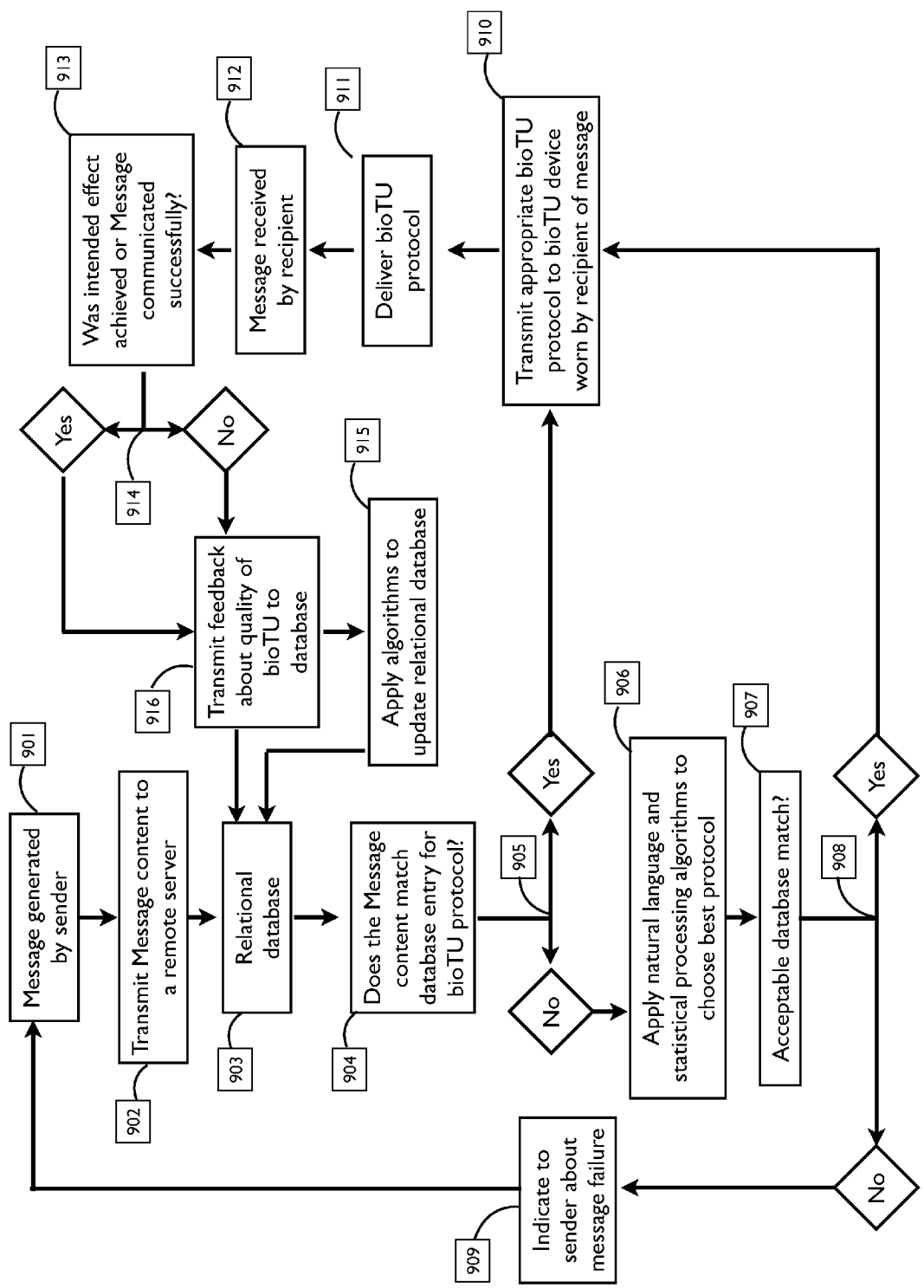
Figure 9. Data / process flow, database feedback, failure feedback, bioTU one-way communication

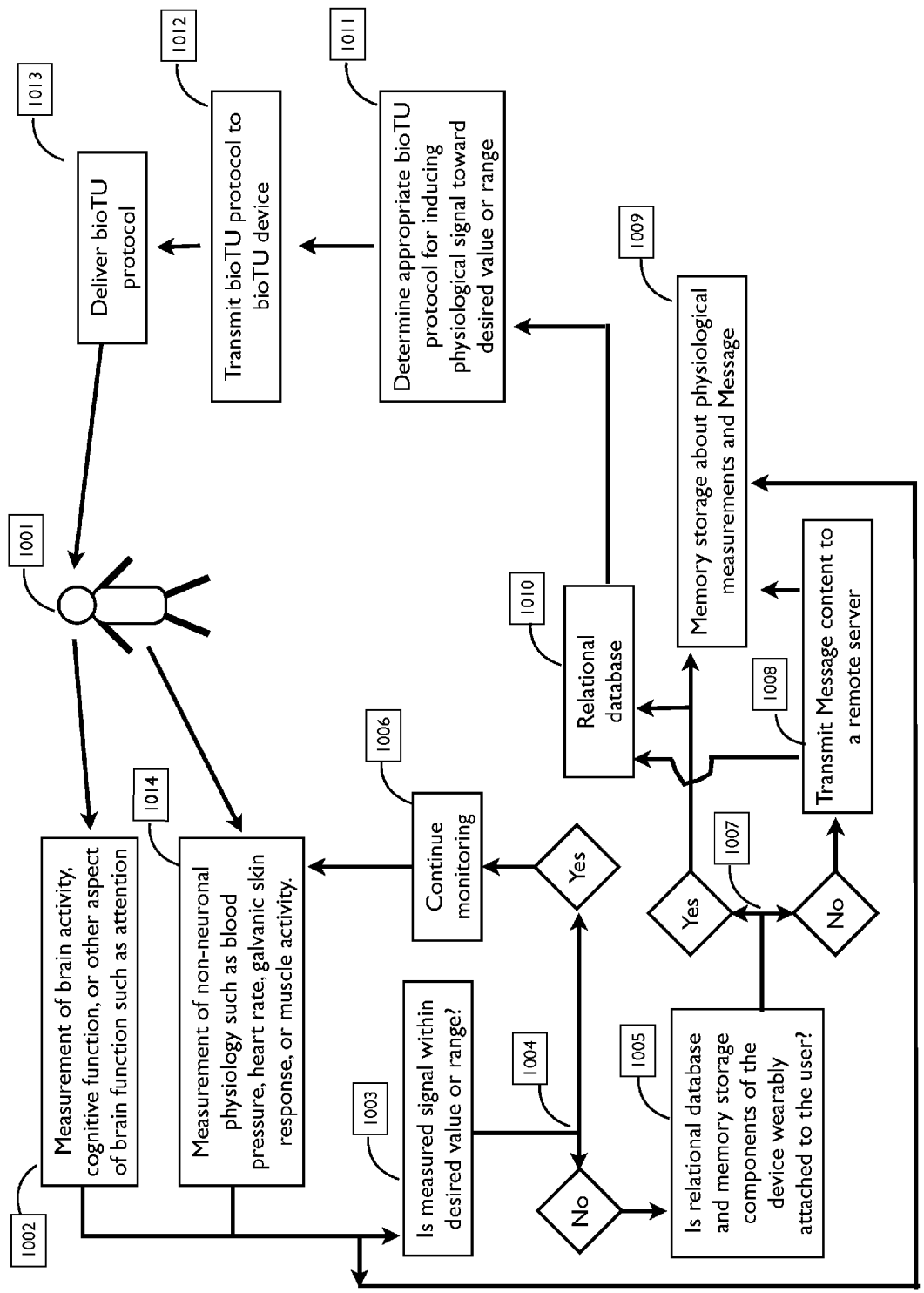
Figure 10. Closed loop communication by bioTU for an individual

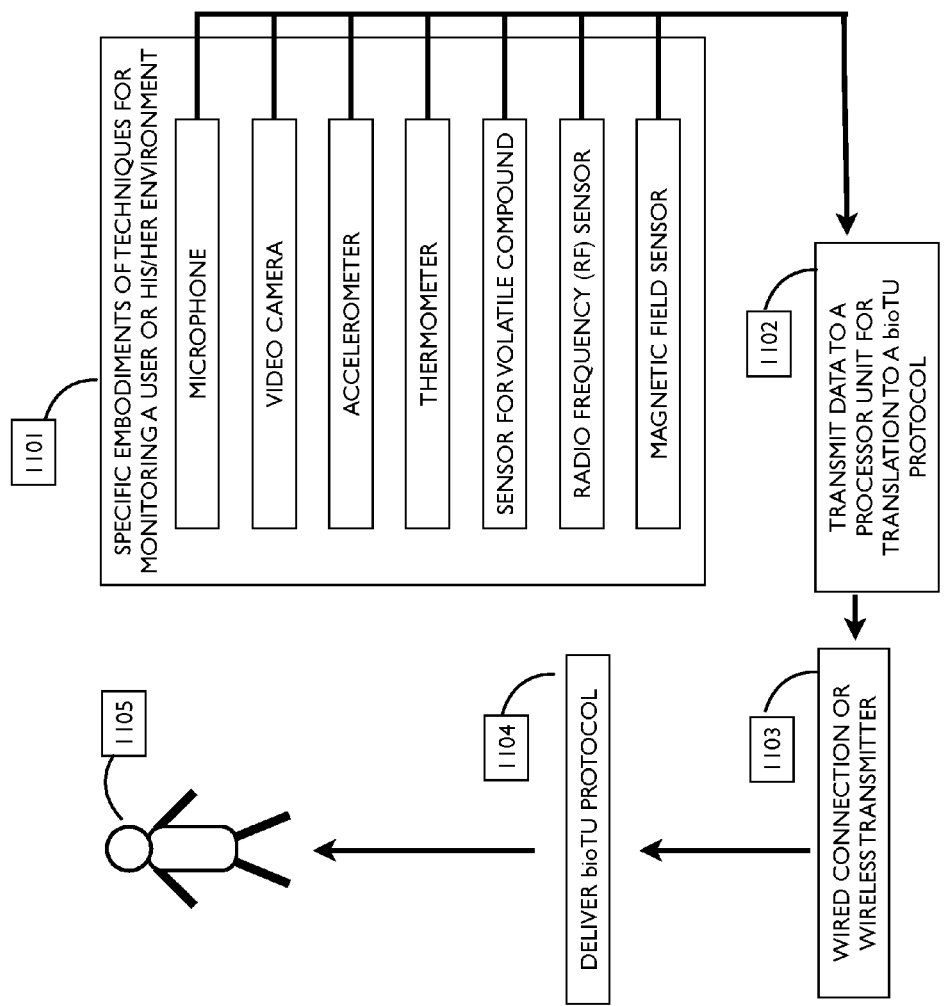
Figure 11. Communication of information via bioTU about a user's environment that cannot be detected by normal sensory transduction pathways

METHOD AND SYSTEM FOR DIRECT COMMUNICATION

CROSS-REFERENCE TO RELATED APPLICATIONS

This application claims the benefit of provisional application 61/550,334, filed on Oct. 21, 2011, the full disclosure of which is incorporated herein by reference.

BACKGROUND OF THE INVENTION

1. Field of the Invention

The present invention relates to devices and methods for communication achieved by neuromodulation via transcranial ultrasound. In various embodiments, messages are sent between one or more individuals, computerized devices, or animals to communicate instructions, words, concepts, cognitive states, emotions, experiences, sensory stimuli, or other forms of conscious or sub-conscious experience.

Communication is a fundamental feature of human and animal behavior. Information exchanged between two or more individuals underlies a wide range of human experience. Spoken, written, and signed language plays a central role in many aspects of communication—from education to storytelling to political speeches and love letters. Other important forms of communication are non-verbal: a hand signal, tap on the shoulder, emotive posture, or facial expression.

In recent years, technological advances have permitted new forms of communication that leverage computers, mobile devices, the Internet, and other digital media known in the art. For the most part, these forms of communication provide new means to use similar verbal, visual, and auditory communication modalities as have been used for millennia.

Other technological advances permit forms of communication that were not previously possible. Brain machine interfaces enable a paralyzed individual to enter text into a computer or move a mouse cursor via a system that decodes patterns of brain activity. Refreshable Braille terminals communicate language via haptic signals to the blind. A belt with an array of vibrating components has been developed that instructs an individual which direction to move or is coupled to a compass to indicate magnetic North by haptic signals. Other simple forms of communication between a device and its operator are tactile feedback such as through video game controllers, keyboards, or touch screens. Communication based on automated transmissions from computerized systems to an individual have become commonplace. An example of an automated communication from a computerized system is a text message alert that a passenger's airline flight is delayed. Further technologies to enhance or supplement existing forms of communication—and create new forms of communication—are desired.

The present invention relates to devices and methods for communication wherein the message is transmitted to the recipient via non-invasive brain neuromodulation (also known in the field as non-invasive neuromodulation).

Various techniques for invasive and non-invasive neuromodulation have been demonstrated in human beings. A non-exhaustive list of these neuromodulation techniques includes transcranial magnetic stimulation (TMS), transcranial direct current stimulation (tDCS), transcranial alternating current stimulation (tACS), targeted electrical stimulation (TES) (as described in patent application 61/663,409 from some of the named inventors of this patent titled "DEVICE AND METHODS FOR NONINVASIVE NEUROMODULATION USING TARGETED TRANSCRANIAL ELECTRICAL STIMULATION"), deep brain stimulation (DBS), and one electrode or an array of electrodes implanted on the surface of the brain or dura (electrocorticography (ECoG) arrays).

Ultrasound (US) has been used for many medical applications, and is generally known as cyclic sound pressure with a frequency greater than the upper limit of human hearing. The production of ultrasound is used in many different fields, typically to penetrate a medium and measure the reflection signature or to supply focused energy. For example, the reflection signature can reveal details about the inner structure of the medium. A well-known application of this technique is its use in sonography to produce a picture of a fetus in a womb. There are other applications which may provide therapeutic effects, such as lithotripsy for ablation of kidney stones or high-intensity focused ultrasound for thermal ablation of brain tumors. An important benefit of ultrasound therapy is its non-invasive nature. US waveforms can be defined by their acoustic frequency, intensity, waveform duration, and other parameters that vary the timecourse of acoustic waves in a target tissue. US waveforms based on pulses less than about 1 second are generally referred to as pulsed ultrasound and are repeated at a rate equivalent to the pulse repetition frequency. Tone bursts that extend for about 1 second or longer—though, strictly speaking, also pulses—are often referred to as continuous wave (CW).

Neurons are mechanically sensitive and can act as a piezoelectric material by converting a mechanical displacement into electrical currents or membrane polarization. Several potential mechanisms for the conversion of mechanical energy into neuronal activity have been proposed. Stretch-induced activation or inactivation of ion channels is one mechanism for converting mechanical force into currents that modulate neuronal activity. Mechanosensitive ion channels convert mechanical force into an electrical signal and contribute to transduction of hearing and touch. Ion channels and receptors that mediate their primary physiological effect through non-mechanical means are also sensitive to mechanical forces. Reversible activation and inactivation responses to stretch have been observed in recombinant systems for voltage-gated $Na^+$, $Ca^{2+}$ (L-type and N-type), and $K^+$ ion channels, as well as for the hyperpolarization-activated channel, HCN. The linear spring properties endowed by the structure of ion channels is one putative mechanism for stretch-induced effects. An additional or alternative mechanism of stretch-induced effects in ion channels may relate to mechanical effects on cytoskeletal proteins such as actin or tubulin that could then be transduced to membrane-bound ion channels through the cytoskeletal structure.

Flexoelectric effects are a second mechanism for converting mechanical energy into changes in neuronal activity. Flexoelectricity was first discovered in the study of liquid crystals. Petrov described flexoelectricity in the context of biological membranes as "a phenomenon of curvature-induced electric polarization of a liquid crystal membrane, in which the molecules of the membrane are uniaxially orientated. Curvature of a membrane bilayer splays the uniaxial orientation of the molecules (lipids, proteins) that it contains and imposes a polar symmetry, such that on one side of the membrane the molecules are moved apart whereas on the other side they are moved closer together. Flexoelectricity results from the resultant electrical polarization of the membrane" (Petrov et al., 1993). Alternatively, flexoelectric effects can operate in the reverse direction in which mechanical energy is converted into membrane polarization. Thermodynamic investigations of lipid-phase transitions have shown that mechanical waves can be adiabatically propagated through lipid monolayers and bilayers, as well as neuronal membranes to influence fluidity and excitability. Notably, such sound wave propagation in pure lipid membranes has been estimated to produce depolarizing potentials ranging from 1 to 50 mV with negligible heat generation (~0.01 K) (Griesbauer et al., 2009), potentially via a flexoelectric effect. In this manner, mechanical energy delivered by an acoustic wave can cause membrane polarization and affect voltage-gated channels and thus neuronal activity.

Another potential mechanism for neuromodulation by ultrasound is by causing changes in blood flow through mechanical and/or thermal effects.

Neuromodulation of the brain, spinal cord, and peripheral nervous system by ultrasound has been shown in animals using transcranial ultrasound for neuromodulation (bioTU). Other transcranial ultrasound based techniques use a combination of parameters to disrupt, damage, destroy, or otherwise affect neuronal cell populations so that they do not function properly and/or cause heating to damage or ablate tissue. Transcranial ultrasound techniques that cause these effects may include high intensities (greater than about 1 W/cm$^2$ at the target tissue) and/or high acoustic frequencies (greater than about 1 MHz) bioTU employs a combination of parameters that transmits mechanical energy through the skull to its target in the brain without causing significant thermal or mechanical damage and induces neuromodulation primarily through mechanical means.

Recent research and disclosures have described the use of bioTU to activate, inhibit, or modulate neuronal activity ((Bystritsky et al., 2011; Tufail et al., 2010; Tufail et al., 2011; Tyler et al., 2008; Yoo et al., 2011; Zaghi et al., 2010), the full disclosures of which are incorporated herein by reference. Also see U.S. Pat. No. 7,283,861 and US patent applications 20070299370, 20110092800 titled "Methods for modifying currents in neuronal circuits" by inventor Alexander Bystritsky; U.S. patent application Ser. No. 12/940,052 (US patent application publication US 2011/0112394) titled "Neuromodulation of deep-brain targets using focused ultrasound" by inventor David J. Mishelevich; and patent applications by one of the named inventors of this submission, William J Tyler: PCT application number US2009/050560 and patent Ser. No. 61/175,413 titled "Methods and Devices for Modulating Cellular Activity using Ultrasound" and PCT application number US2010/055527 titled "Devices and Methods for Modulating Brain Activity", the full disclosures of which are incorporated herein by reference.) The actual mechanisms underlying bioTU have not been fully elucidated. However, one confirmed mechanism for bioTU stimulation of electrical activity in neurons is by activating voltage-gated sodium channels and voltage-gated calcium channels (Tyler et al., 2008). bioTU can induce SNARE-mediated vesicle release and synaptic transmission (Tyler et al., 2008). In contrast to US waves with higher intensities, bioTU does not lead to significant tissue heating in the targeted brain region (Tufail et al., 2010). bioTU activates c-fos and does not disrupt the blood brain barrier (Tufail et al., 2010).

Since many aspects of human cognition relate to communication with others, application of bioTU for communication between individuals or groups would be beneficial. Due to the capacity for US to be delivered non-invasively through the skull in a targeted and focused manner, bioTU can be used to affect brain function in many cognitive domains and in so doing achieve communication to the recipient of bioTU.

The inventions described herein relate primarily to methods and systems that use bioTU as a form of communication.

2. Background Art

The following publications are relevant to the present application.

Arroyo, S., Lesser, R. P., Gordon, B., Uematsu, S., Hart, J., Schwerdt, P., Andreasson, K., and Fisher, R. S. (1993). Mirth, laughter and gelastic seizures. Brain 116 (Pt 4), 757-780.

Bystritsky, A., Korb, A. S., Douglas, P. K., Cohen, M. S., Melega, W. P., Mulgaonkar, A. P., DeSalles, A., Min, B.-K., and Yoo, S.-S. (2011). A review of low-intensity focused ultrasound pulsation. Brain Stimul 4, 125-136.

Farrell, D. F., Leeman, S., and Ojemann, G. A. (2007). Study of the human visual cortex: direct cortical evoked potentials and stimulation. J Clin Neurophysiol 24, 1-10.

Feurra, M., Paulus, W., Walsh, V., and Kanai, R. (2011). Frequency specific modulation of human somatosensory cortex. Front Psychol 2, 13.

Griesbauer, J., Wixforth, A., and Schneider, M. F. (2009). Wave Propagation in Lipid Monolayers. Biophys J 97, 2710-2716.

Petrov, A. G., Miller, B. A., Hristova, K., and Usherwood, P. N. (1993). Flexoelectric effects in model and native membranes containing ion channels. Eur Biophys J 22, 289-300.

Satow, T., Usui, K., Matsuhashi, M., Yamamoto, J., Begum, T., Shibasaki, H., Ikeda, A., Mikuni, N., Miyamoto, S., and Hashimoto, N. (2003). Mirth and laughter arising from human temporal cortex. J Neurol Neurosurg Psychiatr 74, 1004-1005.

Sperli, F., Spinelli, L., Pollo, C., and Seeck, M. (2006). Contralateral smile and laughter, but no mirth, induced by electrical stimulation of the cingulate cortex. Epilepsia 47, 440-443.

Tufail, Y., Matyushov, A., Baldwin, N., Tauchmann, M. L., Georges, J., Yoshihiro, A., Tillery, S. I. H., and Tyler, W. J. (2010). Transcranial pulsed ultrasound stimulates intact brain circuits. Neuron 66, 681-694.

Tufail, Y., Yoshihiro, A., Pati, S., Li, M. M., and Tyler, W. J. (2011). Ultrasonic neuromodulation by brain stimulation with transcranial ultrasound. Nat Protoc 6, 1453-1470.

Tyler, W. J., Tufail, Y., Finsterwald, M., Tauchmann, M. L., Olson, E. J., and Majestic, C. (2008). Remote excitation of neuronal circuits using low-intensity, low-frequency ultrasound. PLoS ONE 3, e3511.

Yoo, S.-S., Bystritsky, A., Lee, J.-H., Zhang, Y., Fischer, K., Min, B.-K., McDannold, N. J., Pascual-Leone, A., and Jolesz, F. A. (2011). Focused ultrasound modulates region-specific brain activity. Neuroimage 56, 1267-1275.

Zaehle, T., Rach, S., and Herrmann, C. S. (2010). Transcranial Alternating Current Stimulation Enhances Individual Alpha Activity in Human EEG. PLoS ONE 5, e13766.

Zaghi, S., Acar, M., Hultgren, B., Boggio, P. S., and Fregni, F. (2010). Noninvasive brain stimulation with low-intensity electrical currents: putative mechanisms of action for direct and alternating current stimulation. Neuroscientist 16, 285-307.

See also WO 2011/057028, WO 2011/009141; and U.S. Pat. No. 7,350,522.

SUMMARY OF THE INVENTION

The present invention comprises methods and systems for modulating the activity of the brain using transcranial ultrasound energy (bioTU) in humans and other organisms for the purpose of communication. Communication can be considered broadly to represent the direct activation of brain regions to deliver information or "messages" to an individual via the subjective experience of sensory stimuli, emotions, physiological arousal, or other higher-order concepts in a manner which can be interpreted by the individual as words or abstract ideas. Devices and systems of the present invention comprise an ultrasound or other neuromodulation device operably attached or coupled to the head of the individual (the recipient) and a mechanism whereby a message is entered, transmitted, and translated to a bioTU protocol.

In the first aspect of present invention, methods for communicating information to an individual comprise directing acoustic energy to the individual and modulating the acoustic energy to encode information to be delivered to the individual. The acoustic energy is preferably directed to the individual's brain through the individual's cranium to produce a cognitive effect. The acoustic energy is modulated to encode the information to be delivered. In particular, the acoustic energy is modulated in a way in which the encoded information is perceptible to the individual through variations in the cognitive effect.

In specific examples, the acoustic energy can be directed at/or to a target region in the brain to cause a selected cognitive effect. Particular examples of target regions and cognitive effects may be found in the following list:

| Cognitive effect | Target region |
|---|---|
| Perception of touch | Somatosensory cortex |
| Auditory perception | Auditory cortex |
| Vestibular perception | Temporal-parietal junction, central sulcus, intraparietal sulcus, and insular cortex |
| Visual perception | Primary and extrastriate visual cortex |
| Olfactory perception | Piriform cortex |
| Language comprehension | Wernicke's area |
| Language production | Broca's area |
| Long-term memory | Hippocampus and parahippocampal formation (and connected portions of cortex, e.g. entorhinal cortex and perirhinal cortex) |
| Modulation of pain processing | Rostral anterior cingulate cortex |
| Emotion | Limbic system (e.g. amygdala) |
| Motor control and movements | Primary and supplementary motor cortex; thalamus; cerebellum; basal ganglia; substantia nigra |
| Attention | Gamma rhythms |
| Relaxation | Alpha rhythms |
| Empathy, social interaction | Brainstem nuclei, hypothalamus, amygdala, anterior cingulated cortex, prefrontal cortex, ventromedial prefrontal cortex, and other brain regions involved in oxytocin and arginine vasopressin function |
| Mirth and laughter | Inferior temporal gyrus, cingulated gyrus, subthalamic nucleus |
| Fear | Amygdala, insular cortex, internal capsule, nucleus accumbens, and anterior temporal gyrus |
| Physiological arousal, sleep state | Various brainstem nuclei |
| Modulation of risk taking | Dorsolateral prefrontal cortex |

Modulating the acoustic energy may be accomplished in any way which produces changes in the cognitive effect which are perceptible to the individual. Most simply, the duration of delivering the acoustic energy which produces the cognitive effect can be controlled. For example, the acoustic energy can be turned off and on in a series of perceptible pulses to communicate information. Complex information can be delivered using a code, such as Morse code or other pre-selected patterns, which are known both to the sender and the individual who receives the information allowing information to be delivered. Alternatively or additionally, the ultrasonic energy could be delivered to different target regions in order to produce different perceptible cognitive effects. The pattern chosen for the different perceptible cognitive effects can be defined or pre-selected in order to convey a particular message to the receiving individual. As a still further example, the intensity of the cognitive effect can be controlled to produce a perceptible pattern which is again recognizable by the individual as information. A variety of other specific patterns and controls are described herein below.

The acoustic energy will typically have a frequency in the range from 100 kHz to 10 MHz, and the energy will typically have a spatial-peak, temporal-average intensity in brain tissue in the range from 0.0001 mW/cm$^2$ to 1 W/cm$^2$. In some examples, the spatial-peak, temporal-average intensity may be modulated in order to encode the information to be delivered to the individual. The energy will typically be selected so that heating of the target region of the brain tissue causes a temperature rise no more than 2° C. for no more than 5 seconds. The energy may be delivered with a pulse length in the range between 0.5 microseconds and 5 seconds. In some cases, the pulse length may be modulated, and in other cases the pulse repetition frequency may be in the range between 50 Hz and 25 kHz.

In addition to these methods, the present invention further provides systems for performing the methods. The systems will comprise means for directing acoustic energy to the individual's brain through the individual's cranium to produce a cognitive effect. Systems will further include means for modulating the acoustic energy to encode information which is perceptible to the individual through variations in the cognitive effect. Other specific aspects of the systems of the present invention have been described above with reference to the methods of the present invention.

BRIEF DESCRIPTION OF DRAWINGS

FIG. 1. bioTU communication framework
FIG. 2. bioTU waveform, pulsed ultrasound protocol
FIG. 3. bioTU waveform, continuous wave ultrasound protocol
FIG. 4. bioTU waveform repetition
FIG. 5. Routes and groups of communication
FIG. 6. Data/process flow, simple version, one-way communication by brain stimulation
FIG. 7. A conversation between two individuals via bioTU
FIG. 8. Data/process flow, one-way communication, bioTU
FIG. 9. Data/process flow, database feedback, failure feedback, bioTU one-way communication
FIG. 10. Closed loop communication by bioTU for an individual
FIG. 11. Communication of information via bioTU about a user's environment that cannot be detected by normal sensory transduction pathways

DETAILED DESCRIPTION

Recent research and disclosures have described the use of transcranial energy (bioTU). As used herein, "bioTU" means transcranial ultrasound energy which can be delivered to an individual human subject to activate, inhibit, or modulate neuronal activity (Tyler et al., 2008). bioTU protocols directed at the brain of a human or animal activate, inhibit, or modulate neuronal activity primarily through mechanical effects when delivered with the appropriate acoustic frequency, duration, intensity, pulse repetition frequency, and pulse length.

Communication via brain stimulation by bioTU represents a novel technique for the delivery and exchange of messages, including information or inducement of a physiological, behavioral, attentional, or emotional response in another. Methods and systems of the present invention permit communication wherein the brain stimulation modulates neuronal activity in a manner such that the recipient perceives a message which can, for example, modify the recipient's cognitive, emotional, physiological, or attentional state according to the sender's message.

bioTU is a beneficial new form of communication achieved through the modulation of brain circuit activity induced by patterned, local vibration of brain tissue using US having an acoustic frequency greater than about 100 kHz and less than about 10 MHz. bioTU transmits mechanical energy through the skull to its target in the brain without causing significant thermal or mechanical damage and induces neuromodulation. bioTU employs low intensity ultrasound such that the spatial-peak, temporal-average intensity ($I_{spta}$) of the bioTU protocol is less than about 1 W/cm$^2$ in the targeted brain tissue. The acoustic intensity measure $I_{spta}$ is calculated according to established techniques well known to those skilled in the art that relate to the ultrasound acoustic pressure (201, 301, FIGS. 2 and 3) and other bioTU protocol characteristics such as the temporal average power during the bioTU waveform duration (208, 305). To provide a large matrix of complex patterns of localized brain tissue vibration, US may be delivered as short-lived continuous waves less than about 5 seconds or in a pulsed manner during bioTU protocols such that diverse patterns of neuromodulation can be delivered to achieve communication as herein described. For modulating the activity of brain circuits through localized tissue vibration, bioTU protocols may utilize US waveforms of any type known in the art including but not limited to amplitude modulated waveforms, tone-bursts, pulsed waveforms, and continuous waveforms.

In a preferred embodiment of this invention, bioTU is used to communicate a message whereby:

One or more ultrasound transducers are coupled to the head of an individual human or animal (the 'recipient') (101, FIG. 1);

Components of the bioTU device are near or wearably attached to the recipient in order to provide power and control the intensity, timing, targeting, and waveform characteristics of the transmitted acoustic waves (105, FIG. 1);

a bioTU protocol is triggered that uses a waveform that (102, FIG. 1):

a. has an acoustic frequency between about 100 kHz and about 10 MHz (103, FIG. 1); and b. has a spatial-peak, temporal-average intensity between about 0.0001 mW/cm$^2$ and about 1 W/cm$^2$ at the target tissue site (104, FIG. 1); and c. does not induce heating of the brain due to bioTU that exceeds about 2 degrees Celsius for more than about 5 seconds (106, FIG. 1)

the bioTU protocol induces an effect on neural circuits in one or more brain regions (107, FIG. 1);

the effect of bioTU on brain function is detected (108, FIG. 1):

a. subjectively by the recipient as a perception, movement, concept, instruction, other symbolic communication, or by modifying the recipient's cognitive, emotional, physiological, attentional, or other cognitive state (109, FIG. 1);

b. through physiological measurement of brain activity by one or a plurality of: electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), or other techniques for measuring brain activity known to one skilled in the art; (101, FIG. 1); or c. physiological measurement of the body such as by electromyogram (EMG), galvanic skin response (GSR), heart rate, blood pressure, respiration rate, pupil dilation, eye movement, gaze direction, or other physiological measurement (111, FIG. 1).

In secondary embodiments, one or more other techniques for invasive or non-invasive brain stimulation can be used for communication in addition to or instead of bioTU. In these secondary embodiments, the methods and devices comprise use of alternative technologies for delivering electrical, magnetic, or mechanical stimulation to brain tissue to activate, inhibit, or modulate the activity of cells in the brain such as transcranial magnetic stimulation (TMS), transcranial direct current stimulation (tDCS), transcranial alternating current stimulation (tACS), targeted electrical stimulation (TES), deep brain stimulation (DBS), one electrode or an array of electrodes implanted on the surface of the brain or dura, and light activation of specially engineered proteins for neuromodulation known as optogenetics. These alternative methods for brain stimulation are limited relative to bioTU in terms of targeting, depth of penetration, richness of stimulation parameters available, invasiveness, and/or discomfort, but in certain limited embodiments are useful for communication.

Ultrasound can be defined as low or high intensity. In contrast to bioTU, ultrasound imaging generally employs high intensity (greater than about 1 W/cm$^2$), high frequency ultrasound (greater than about 1 MHz). In ultrasound, acoustic intensity is a measure of power per unit of cross sectional area (e.g. mW/cm$^2$) and requires averaging across space and time. The intensity of the acoustic beam can be quantified by several metrics that differ in the method for spatial and temporal averaging. These metrics are defined according to technical standards established by the American Institute for Ultrasound in Medicine and National Electronics Manufacturers Administration (NEMA. Acoustic Output Measurement Standard For Diagnostic Ultrasound Equipment (National Electrical Manufacturers Association, 2004)). A commonly used intensity index is the 'spatial-peak, temporal-average' intensity ($I_{spta}$). The intensities reported herein refer to $I_{spta}$ at the targeted brain region.

Acoustic frequencies greater than about 1 MHz used in ultrasound imaging and most previous ultrasound neuromodulation studies have disadvantages in regard to tissue heating and transmission of mechanical energy. Damage due to ultrasound can occur due to thermal effects (heating) or mechanical effects (such as inertial cavitation—the creation of air bubbles that expand and contract with the time-varying pressure waves). High-intensity US can readily produce mechanical and/or thermal tissue damage, precluding it from use in non-invasive brain-circuit stimulation. High-intensity US (>1 W/cm$^2$) influences neuronal excitability by producing thermal effects. Transcranial delivery of ultrasound at these frequencies leads to tissue heating, particularly of bone in the skull.

Since low-frequency US can be reliably transmitted through skull bone transcranial US is capable of safely and reliably stimulating in vivo brain circuits in humans and animals. Until recently, appropriate acoustic waveform protocols for neuromodulation without causing damage had not been discovered. bioTU employs an ultrasound acoustic waveform that transmits mechanical energy through the skull to its target in the brain without causing damage. bioTU is an advantageous form of brain stimulation for communication due to its non-invasiveness, safety, focusing characteristics, and the capacity to vary bioTU waveform protocols for specificity of neuromodulation.

US causes the local vibration of particles, leading to both mechanical and thermal effects. In some embodiments, bioTU brain stimulation protocols modulate neuronal activity primarily through mechanical means.

One important piece of evidence indicating that the mechanism of bioTU is primarily mechanical rather than thermal is that the timecourse of neuromodulation correlates more strongly with the timecourse of mechanical energy transmission than with the timecourse of thermal effects in the tissue. Tufail, Tyler, and colleagues showed that electrophysiological responses to bioTU in mice occur within tens to hundreds of milliseconds of the onset of the bioTU protocol. In contrast, tissue heating occurs on a timescale of 100 s of milliseconds to seconds (Tufail et al., 2010). Moreover, effective bioTU brain stimulation occurred in these mice without tissue heating. In these studies, a 0.87 mm diameter thermocouple (TA-29, Warner Instruments, LLC, Hamden, Conn., USA) was inserted into motor cortex through a cranial window and no deviation in brain temperature greater than the noise level of these recordings (about 0.01 degrees Celsius) was observed (Tufail et al., 2010).

The mechanical effects of US induce neuromodulation before mechanical energy becomes absorbed to a sufficient degree such that sufficient tissue heating can occur to affect neural circuit function by thermal means. The acoustic pressure wave begins to affect the mechanosensitivty of lipid bilayers, protein channels, and neuronal membranes at the speed of sound in tissue (microseconds to tens of microseconds). The temporally lagging tissue heating incurred by US tends to be slower than the mechanical effects requiring tens of milliseconds in time or longer.

The thermal index (TI) of ultrasound is the ratio of power applied to that which would raise the temperature of tissue by 1 degree Celsius. The TI is an important parameter used to assess the heating of tissue due to absorption of energy from the acoustic waves. Bone absorbs ultrasound to a greater degree than other tissues, so TI values for bone are higher for a given ultrasound waveform relative to other tissues. The skull reflects, diffracts, and absorbs acoustic energy fields during transcranial US transmission. The acoustic impedance mismatches between the skin-skull and skull-brain interfaces present additional challenges for transmitting and focusing US through the skull into the intact brain. The absorption of ultrasound by bone is highly dependent on the acoustic frequency with more absorption at frequencies greater than about 1 MHz. Ultrasound below about 0.7 MHz is transmitted more effectively through bone and thus beneficial for bioTU due to reduced heating of the skull. A second reason that bioTU employs lower acoustic frequencies than used for imaging applications is that the mechanical index of ultrasound scales inversely with the square root of the acoustic frequency. Thus, reducing the acoustic frequency by half (e.g. from 1 MHz to 0.5 MHz) increases the mechanical power transmitted to the target tissue by about 1.4 (the square root of 2).

The parameters of bioTU are critical for ensuring that neuromodulation occurs without damage. bioTU parameters, described in more detail below, include the use of low intensity (less than about 1 W/cm$^2$ at the target tissue), low acoustic frequency (between about 100 kHz and about 10 MHz), and an appropriate pulse repetition frequency, pulse length, and waveform duration such that the temperature of the target brain region does not rise by more than about 2 degrees Celsius for a period longer than about 5 seconds. Specific communication embodiments may employ distinct combinations of acoustic intensity, acoustic frequency, pulse repetition frequency, pulse length, and waveform duration to achieve the desired effect on the targeted brain region. In some specific communication embodiments, a single pulse is delivered that may be referred to as a continuous wave (CW) pulse by one skilled in the art and extends in time for about longer than 10 ms, about longer than 100 ms, about longer than 1 second, or about longer than any length of time up to and including 5 seconds.

Appropriate bioTU protocols are advantageous for mitigating or eliminating tissue damage while simultaneously modulating neuronal activity primarily through mechanical means. For example, low temporal average intensity can be achieved by reducing the acoustic power of the ultrasound waves or by varying one or more bioTU parameters to decrease the effective duty cycle—the proportion of time during a bioTU waveform that ultrasound is delivered. Reduced duty cycles can be achieved by decreasing one or more bioTU parameters chosen from pulse length, cycles per pulse, and pulse repetition frequency.

Depending on the bioTU protocol, activation or inhibition of brain activity can be achieved. Although not intending to be restricted to any one theory for the activation of voltage-gated channels by bioTU, one hypothesis for opening of these channels is by mechanical stretching of the receptors to an open configuration. In alternative embodiments, alternate bioTU stimulation protocols can be chosen in order to specifically activate one or more types of membrane bound, cytoskeletal, or cytoplasmic proteins including ion channels, ion pumps, or secondary messenger receptors. In this embodiment, it would be possible to selectively activate or inhibit specific cell types based on their expression of the targeted protein.

A bioTU protocol delivers ultrasound to one or more brain regions and induces neuromodulation that correlates more strongly in time with the timecourse of mechanical effects on tissue than thermal effects. The acoustic frequency for bioTU is generally greater than about 100 kHz and less than about 10 MHz (205, 303, FIGS. 2 and 3), i.e. generally greater than about 100 kHz and less than about 10 MHz; optionally greater than about 0.3 MHz and less than about 0.8 MHz; optionally greater than about 0.3 MHz and less than about 1 MHz; optionally greater than about 0.3 MHz and less than about 0.5 MHz; optionally greater than about 0.3 MHz and less than about 0.4 MHz; optionally greater than about 0.3 MHz and less than about 0.6 MHz; optionally greater than about 0.3 MHz and less than about 10 MHz; optionally greater than about 0.25 MHz and less than about 0.8 MHz; optionally greater than about 0.25 MHz and less than about 1 MHz; optionally greater than about 0.25 MHz and less than about 0.5 MHz; optionally greater than about 0.25 MHz and less than about 0.4 MHz; optionally greater than about 0.25 MHz and less than about 0.6 MHz; optionally greater than about 0.25 MHz and less than about 10 MHz; optionally greater than about 0.1 MHz and less than about 0.8 MHz; optionally greater than about 0.1 MHz and less than about 1 MHz; optionally greater than about 0.1 MHz and less than about 0.5 MHz; optionally greater than about 0.1 MHz and less than about 0.4 MHz; optionally greater than about 0.1 MHz and less than about 0.6 MHz; optionally greater than about 0.1 MHz and less than about 10 MHz; optionally greater than about 0.5 MHz and less than about 0.8 MHz; optionally greater than about 0.5 MHz and less than about 1 MHz; optionally greater than about 0.5 MHz and less than about 0.55 MHz; optionally greater than about 0.5 MHz and less than about 0.7 MHz; optionally greater than about 0.5 MHz and less than about 0.6 MHz; optionally greater than about 0.5

MHz and less than about 10 MHz; optionally greater than about 0.7 MHz and less than about 0.8 MHz; optionally greater than about 0.7 MHz and less than about 1 MHz; optionally greater than about 0.7 MHz and less than about 0.75 MHz; or optionally greater than about 0.5 MHz and less than about 10 MHz. Particularly advantageous acoustic frequencies are between about 0.3 MHz and about 0.7 MHz. The spatial-peak temporal-average ($I_{spta}$) intensity of the ultrasound wave in brain tissue is greater than about 0.0001 mW/cm$^2$ and less than about 1 W/cm$^2$, i.e. generally from 21 mW/cm$^2$ to 0.1 W/cm$^2$; optionally from 21 mW/cm$^2$ to 0.5 W/cm$^2$; optionally from 21 mW/cm$^2$ to 1 W/cm$^2$; optionally from 50 mW/cm$^2$ to 0.1 W/cm$^2$; optionally from 50 mW/cm$^2$ to 0.5 W/cm$^2$; optionally from 50 mW/cm$^2$ to 1 W/cm$^2$; optionally from 0.1 W/cm$^2$ to 0.2 W/cm$^2$; optionally from 0.1 W/cm$^2$ to 0.5 W/cm$^2$; and optionally from 0.1 W/cm$^2$ to 1 W/cm$^2$. Particularly advantageous $I_{spta}$ values are between about 100 mW/cm$^2$ and about 700 mW/cm$^2$, usually in the range from about 200 mW/cm$^2$ to about 500 mW/cm$^2$. The $I_{spta}$ value for any particular bioTU protocol is calculated according to methods well known in the art that relate to the ultrasound pressure (FIG. 209) and temporal average of the bioTU waveform over its duration (FIG. 208). Effective ultrasound intensities for activating neurons or neuronal circuits do not cause tissue heating greater than about 2 degrees Celsius, usually less than 1 degree Celsius, for a period longer than about 5 seconds, preferably no longer than 3 seconds.

Significant attenuation of ultrasound intensity occurs at the boundaries between skin, skull, dura, and brain due to impedance mismatches, absorption, and reflection so the required ultrasound intensity delivered to the skin or skull may exceed the intensity at the targeted brain region by up to 10-fold or more depending on skull thickness and other tissue and anatomical properties.

Pulsing of ultrasound is an effective strategy for activating neurons that reduces the temporal average intensity while also achieving desired brain stimulation or neuromodulation effects. In addition to acoustic frequency and transducer variables, several waveform characteristics such as cycles per pulse, pulse repetition frequency, number of pulses, and pulse length affect the intensity characteristics and outcome of any particular bioTU stimulus on brain activity. A pulsed bioTU protocol generally uses pulse lengths (206) between about 0.5 microseconds and about 1 second, i.e. generally from 0.5 microseconds to 5 microseconds; optionally from 0.5 microseconds to 50 microseconds; optionally from 0.5 microseconds to 100 microseconds; optionally from 0.5 microseconds to 500 microseconds; optionally from 0.5 microseconds to 1 ms; optionally from 0.5 microseconds to 10 ms; optionally from 0.5 microseconds to 100 ms; optionally from 0.5 microseconds to 500 ms; optionally from 0.5 microseconds to 1 second; optionally from 5 microseconds to 50 microseconds; optionally from 5 microseconds to 100 microseconds; optionally from 5 microseconds to 500 microseconds; optionally from 5 microseconds to 1 ms; optionally from 5 microseconds to 10 ms; optionally from 5 microseconds to 100 ms; optionally from 5 microseconds to 500 ms; optionally from 5 microseconds to 1 second; optionally from 100 microseconds to 500 microseconds; optionally from 100 microseconds to 1 ms; optionally from 100 microseconds to 10 ms; optionally from 100 microseconds to 100 ms; optionally from 100 microseconds to 500 ms; optionally from 100 microseconds to 1 second; optionally from 500 microseconds to 1 ms; optionally from 500 microseconds to 10 ms; optionally from 500 microseconds to 100 ms; optionally from 500 microseconds to 500 ms; optionally from 500 microseconds to 1 second; optionally from 1 ms to 10 ms; optionally from 1 ms to 100 ms; optionally from 1 ms to 500 ms; optionally from 1 ms to 1 second; and optionally from and 100 ms to 1 second. A bioTU protocol may use pulse repetition frequencies (PRFs) between about 50 Hz and about 25 kHz, (207) i.e. generally from 50 Hz to 100 Hz; optionally from 50 Hz to 250 Hz; optionally from 50 Hz to 1 kHz; optionally from 50 Hz to 2 kHz; optionally from 50 Hz to 3 kHz; optionally from 50 Hz to 4 kHz; optionally from 50 Hz to 5 kHz; optionally from 50 Hz to 10 kHz; optionally from 50 Hz to 25 kHz; optionally from 100 Hz to 250 Hz; optionally from 100 Hz to 1 kHz; optionally from 100 Hz to 2 kHz; optionally from 100 Hz to 3 kHz; optionally from 100 Hz to 4 kHz; optionally from 100 Hz to 5 kHz; optionally from 100 Hz to 10 kHz; optionally from 100 Hz to 25 kHz; optionally from 250 Hz to 500 Hz; optionally from 250 Hz to 1 kHz; optionally from 250 Hz to 2 kHz; optionally from 250 Hz to 3 kHz; optionally from 250 Hz to 4 kHz; optionally from 250 Hz to 5 kHz; optionally from 250 Hz to 10 kHz; optionally from 250 Hz to 25 kHz; optionally from 500 Hz to 1 kHz; optionally from 500 Hz to 2 kHz; optionally from 500 Hz to 3 kHz; optionally from 500 Hz to 4 kHz; optionally from 500 Hz to 5 kHz; optionally from 500 Hz to 10 kHz; optionally from 500 Hz to 25 kHz; optionally from 1 kHz to 2 kHz; optionally from 1 kHz to 3 kHz; optionally from 1 kHz to 4 kHz; optionally from 1 kHz to 5 kHz; optionally from 1 kHz to 10 kHz; optionally from 1 kHz to 25 kHz; optionally from 3 kHz to 4 kHz; optionally from 3 kHz to 5 kHz; optionally from 3 kHz to 10 kHz; optionally from 3 kHz to 25 kHz; optionally from 5 kHz to 10 kHz; optionally from 5 kHz to 25 kHz; and optionally from and 10 kHz to 25 kHz. Particularly advantageous PRFs are generally between about 1 kHz and about 3 kHz. For pulsed bioTU waveforms, the number of cycles per pulse (cpp) is between about 5 and about 10,000,000. Particularly advantageous cpp values vary depending on the choice of other bioTU parameters and are generally between about 10 and about 250. The number of pulses for pulsed bioTU waveforms is between about 1 pulse and about 125,000 pulses. In FIG. 2, the 1$^{st}$ (201), 2$^{nd}$ (202), and nth (204) pulses are shown, with the gap in the horizontal line (203) indicating additional pulses that may number between about 1 and about 125,000 pulses. Particularly advantageous pulse numbers for pulsed bioTU waveforms are between about 100 pulses and about 250 pulses.

Tone bursts that extend for about 1 second or longer—though, strictly speaking, also pulses—are often referred to as continuous wave (CW). In alternative embodiments, one or more continuous wave (CW) ultrasound waveforms less than about five seconds in duration, typically being from 1 second to 5 seconds. (302, 304, 305, FIG. 3) is directed to the brain for the purpose communication via neuromodulation. US protocols that include such CW waveforms offer advantages for neuromodulation due to their capacity to drive activity robustly. However, one disadvantage of bioTU protocols with CW pulses is that the temporal average intensity is significantly higher which may cause painful thermal stimuli on the scalp or skull and may also induce heating and thus damage in brain tissue. Thus, advantageous embodiments using CW pulses may employ a lower acoustic intensity and/or a slow pulse repetition frequency of less than about 1 Hz. For instance, a CW US stimulus waveform with 1 second pulse lengths repeated at 0.5 Hz would deliver US every other second. Alternative pulsing protocols including those with slower pulse repetition frequencies of less than about 0.5 Hz or less than about 0.1 Hz or less than about 0.01 Hz or less than about 0.001 Hz are also beneficial. In some useful embodiments, the interval between pulses or pulse length may be varied during a bioTU protocol that include CW pulses.

In some embodiments, repeating the bioTU protocol is advantageous for achieving particular forms of neuromodulation during a bioTU communication event (406, FIG. 4). In some embodiments, the number of times a bioTU protocol of appropriate duration (404) is repeated is chosen to be in the range between 2 times and 100,000 times. (401, 402, 403) presents a schematic of three repeated bioTU protocols. Particularly advantageous numbers of bioTU protocol repeats are between 2 and 1,000 repeats. The repetition frequency (405) of a bioTU protocol may be less than about 10 Hz, less than about 1 Hz, less than about 0.1 Hz, or lower. The bioTU repetition frequency may be fixed or variable. Variable bioTU repetition frequency values may be random, pseudo-random, ramped, or otherwise modulated. The bioTU repetition period is defined as the inverse of the bioTU repetition frequency.

Providing a mixture of ultrasound frequencies is useful for efficient brain stimulation. Various strategies for achieving a mixture of ultrasound frequencies to the brain of the user are known. Driving an ultrasound transducer at a frequency other than the resonant frequency of the transducer is one way to create ultrasound waves that contain power in a range of frequencies. For instance, an ultrasound transducer with a center frequency of 0.5 MHz can be driven with a sine wave at 0.35 MHz. A second strategy for producing ultrasound waves that contain power in a range of frequencies is to use square waves to drive the transducer. A third strategy for generating a mixture of ultrasound frequencies is to choose transducers that have different center frequencies and drive each at their resonant frequency. One or more of the above strategies or alternative strategies known to those skilled in the art for generating US waves with a mixture of frequencies would also be beneficial. Mixing, amplitude modulation, or other strategies for generating more complex bioTU waveforms can be beneficial for driving distinct brain wave activity patterns or to bias the power, phase, or spatial extent of brain oscillations such as slow-wave, delta, beta, theta, gamma, or alpha rhythms.

The effect of bioTU on brain activity may be increased or decreased by the action of at least one of the ultrasound waves, which may include increasing or decreasing neuron firing, receptivity, release or uptake of neurohormones, neurotransmitters or neuromodulators, increase or decrease of gene transcription, protein translation or protein phosphorylation or cell trafficking of proteins or mRNA, or affect the activity of other brain cell or brain structure activity.

The major advantages of bioTU for brain stimulation are that it offers a mesoscopic spatial resolution of a few millimeters and the ability to penetrate beyond the brain surface while remaining completely non-invasive. bioTU has beneficial advantages over other forms of non-invasive neuromodulation that include focusing, targeting tissues at depth, and painless stimulation procedures. Ultrasound also offers a rich degree of flexibility for modifying the stimulation protocol. One potentially advantageous aspect of the large parameter space available for bioTU is the possibility of improving the specificity of the induced neuromodulation effect with regard to cell type, sub-cellular compartment, receptor type, or brain structure by varying bioTU parameters. In contrast, other non-invasive forms of brain stimulation are more limited in the extent to which stimulation parameters can be varied. For instance, the spatial extent of TMS is fixed for a given electromagnet. For tDCS, only the location and type of electrodes, current amplitude, and stimulus duration can be varied. Due to its rich parameter space for being able to generate a wide variety of distinct stimulus waveforms yielding different effects on neural activity patterns (Tufail et al., 2011), bioTU is well-suited to provide a non-invasive brain stimulation method for communication as invented here.

In some embodiments, bioTU can be delivered from an array of transducers for improved targeting of one or more brain regions. Constructive and destructive interference of acoustic waves transmitted by multiple transducers can be used to deliver complex spatiotemporal patterns of acoustic waves. Moreover, the spectral density of acoustic pressure profiles delivered to a targeted brain region can be varied to produce differential effects on neuronal activity. These properties of bioTU offer the possibility of activating widely distributed brain networks. In certain embodiments, the capacity to target distributed brain regions concurrently or with a specific order further extends the possibilities for communication by modulating brain activity.

A device for brain stimulation using bioTU includes a plurality of components to generate, transduce, and couple ultrasound acoustic waves to the head of a human or animal.

A power source provides power to the various components of the device including one or more of function generators, controllers, radio frequency (RF) power amplifiers, and ultrasound transducers. A computer or other controller hardware with general or custom software is used to control the timing and protocol parameters of bioTU and other aspects of a bioTU communication system. In one embodiment, a first function generator (FG1) is used to trigger US pulses, establish the pulse-repetition frequency (PRF) and define the number of pulses (np) in a bioTU stimulus waveform (Tufail et al., 2011). FG1 triggers a second function generator 2 (FG2) that establishes the acoustic frequency (Af) and the number of cycles per pulse (cpp) in a bioTU stimulus waveform. An RF amplifier receives a voltage waveform input from FG2 and provides output power to an ultrasound transducer that generates the acoustic wave of the bioTU stimulus.

Various ultrasound transducers can be used to generate the acoustic wave. Specific water immersion type transducers are the Ultran GS500-D13, NDT Systems IBMF0.53, Ultran GS350-D19, Olympus Panametrics V318 focused transducer 0.5 MHz/0.75" F=0.85", Ultran GS200-D25 and Olympus Panametrics V301S 0.5 MHz/1.0".

For the vast majority of transducers (air-coupled transducers being an exception), the ultrasound device must be in physical contact with the subject due to the poor impedance match between air and tissue. Ultrasound gel (or another coupling material) is usually used to couple the transducer apparatus to the head to minimize distortion or reflection of the ultrasound waveform due to acoustic impedance mismatch. In some embodiments of a bioTU device, components for cooling are used due to heating that can occur in the transducer, coupling gel, brain, and/or body. Although some components of the bioTU device may be placed remotely from the subject, transducers other than air-coupled transducers require physical attachment to the subject in this embodiment. The subject's head may be placed in an assembly that holds the transducer assembly in contact with the user. Alternatively, the transducer apparatus may be wearably attached to the user with a helmet, headband, adhesive material, hat, eyeglasses, or other piece of wearable hardware or clothing.

bioTU can be delivered in a targeted manner to activate a specific brain region. Alternatively, a bioTU device can be unfocused in order to modulate the activity of multiple brain regions, a cerebral hemisphere, or other large areas up to the size of the entire brain.

Several strategies are known for targeting bioTU to a specific brain region. When using water-matched transducers, the transmission of US from the transducer into the brain only occurs at points at which acoustic gel (or other coupling fluid) physically couples the transducer to the head. On the basis of this acoustic transmission property, coupling the transducer to the head through small gel contact points represents one physical method for transmitting US into restricted brain regions (Tufail et al., 2010). In this embodiment, the entire face of the transducer should always be covered with acoustic gel to prevent heating and damage of the transducer face. The area of gel coupling the transducer to the head, however, can be sculpted to restrict the lateral extent through which US is transmitted into the brain. Although this method does provide an effective approach for stimulating coarsely targeted brain regions, calculating acoustic intensities transmitted into the brain with this method can be difficult because of nonlinear variations in the acoustic pressure fields generated.

Alternatively, the lateral extent of the spatial envelope of US transmitted into the brain can be restricted by using acoustic collimators. Single-element transducers having concave focusing lenses or transducers shaped to deliver a targeted acoustic wave can also be used for delivering focused acoustic pressure fields to brains. Such single-element focused transducers can be manufactured having various focal lengths depending on the lens curvature, as well as the physical size and center frequency of the transducer. The most accurate yet complicated US focusing method involves the use of multiple transducers operating in a phased array.

Components for communication via neuromodulation delivered by bioTU require both general-purpose communication hardware and specialized components. In a first step, the sender generates a message. The message can be generated using any known communication hardware or software. Such devices and methods can take the form of messages entered on a computer or mobile device, or communicated through speech, signaled movement, written text, or detected through recording the physiological, cognitive, or other state of the sender. In some embodiments, the sender is an automated or computerized system. The content of the message is processed by a specialized system to translate the message to determine an appropriate protocol to communicate the message to the recipient. The system may reside on a device used to generate the message, on the device used to transmit bioTU to the recipient, or remotely on a server connected to the sender and recipient via the Internet.

The appropriate bioTU protocol may include bioTU parameters such as intensity, duration, pulse repetition frequency, frequency, or cycles per pulse. Alternatively, the appropriate protocol for communication may also include targeting information to modify the targeting of ultrasound delivery to a specific brain region appropriate for eliciting the intended effect. One aspect of the bioTU device may relate to targeting of the ultrasound pulse to achieve the intended effect by moving the ultrasound transducer or altering its focusing. Finally, the bioTU stimulus is triggered and the message is communicated to the recipient by activating, inhibiting, or modulating the activity of neuronal circuits in the targeted brain region. In response, the recipient receives a message, executes a movement, perceives a sensory stimulus, or experiences modification to their mood, energy level, attention, physiological arousal, or other cognitive state. (See U.S. Pat. No. 7,350,522 titled "Scanning method for applying ultrasonic acoustic data to the human neural cortex" by inventor Thomas Patrick Dawson, the full disclosures of which are incorporated herein by reference.)

Communication is a fundamental aspect of interactions among organisms. Humans and animals communicate via vocal, visual, physical, and chemical means. Broadly defined, communication refers to the process whereby information is exchanged through a common system of symbols, signs, or behavior. Communication requires a sender, a message, and an intended recipient.

A variety of methods and modalities for an individual to receive information, including communication from another individual, are well known. Communication can take the form of spoken language, written language, facial expressions, postures, drawings, paintings, musical performances, symbolic representations (Morse code, signaling flags, hieroglyphics, sign language, haptic input such as Braille, etc.), or utterances from an animal such as a bark, growl, or meow. However, communication has to date been limited to modalities that activate sensory organs for sight, hearing, smell, taste, touch, and linear or rotational accelerations detected by the vestibular system. Of these senses, sight, hearing, and touch are the primary modalities underlying the production and receipt of communication.

Cognitive processes are required to derive meaning and other higher order insights from such forms of communication. For instance, recognition of words, concepts, specific individuals, or emotional content of a message requires higher order processing. It is well known from psychophysical and neurobiological experiments that deriving such insights from a communication is relatively slow compared to, for instance, recognition of the location of a flash of light, indicating that a period of some 10 s to 100 s of milliseconds or longer is required for processing more complex concepts.

Communication can occur through direct interaction or over great distance for instance through the use of letters sent through the mail, email messages, or phone calls. In some instances of communication, the content, meaning, intention, or sender of the message may be unknown or not understood by the recipient of the communication. Communication can take many different forms and may be mediated through different sensory modalities. Communication includes explicit forms of verbal communication such as written and spoken language, lip reading, and sign language. Communication in modern society takes advantage of devices such as cellular phones, mobile handsets, computers, tablet computers, and other interactive devices. Many forms of communication use the Internet such as email, blog postings, or postings to social media sites such as Twitter or Facebook.

In some instances of communication, the sender may not be aware that they are sending a message, including, but not limited to, cases in which an individual's facial expressions, posture, pheromones, or verbal tone are interpreted by another individual (the recipient) as a communication of emotion, intent, or level of physiological or sexual arousal.

In other instances of communication, the sender may communicate a message without having a specific intended recipient or recipients. Specific embodiments of this type of communication—though not intended as an exhaustive list—include graffiti, recorded musical performances, and blog postings.

In some instances of communication, the recipient is not present at the time or place that the sender creates a message. This form of communication is asynchronous. For instance, an artist who creates a drawing or painting or a musician who records a song or writes a musical score effectively communicates an artistic message to a future audience. At the time the artist creates the piece of art—or at a time in the near or distant future—an audience member (the recipient) receives a communicated message related to the content of the created art. Asynchronous forms of communication include text messaging, voicemail messages, and email.

Communication can evoke an emotional response in the recipient or the sender of the communication. Communication can lead to long-lasting emotional relationships including those between a husband and wife, parent and child, or mentor and mentee. Communication can also evoke strong negative emotions as is the case for hateful speech or threats. Neurobiologically, some of these long-lasting emotional connections are known to relate to hormones such as oxytocin, which is believed to play a role in the formation of pair bonds between individuals.

Communication also occurs between individuals through touch for instance by a hug, handshake, kiss, or pat on the back. Communication commonly takes a multimodal form in which multiple modes of communication are used such as emotional cues derived from an expression and concepts expressed verbally.

Communication can occur between two individuals with one-way communication (501, 502, FIG. 5) or two-way communication (503, 504); an individual (505) to a group of two or more individuals (506, 507, 508); from a group of two or more individuals (510, 511, 512) to an individual (509); among a group of two or more individuals (513, 514), or between two or more groups of two or more individuals. Communication can also occur between animals of the same species or between individuals of different species. Communication can occur for instance between a human and an animal such as a pet dog.

Some forms of communication are public such as a political speech or radio broadcast. Other forms of communication are private as occurs in discrete conversation, coded messages, or written letters. Yet other forms of communication are made to oneself as is the case with talking to oneself (e.g. for the purposes of calming in a stressful situation) (515) or a note written as a reminder for a later time (516). In modern society, many forms of communication are generated automatically by a computer system, gaming system, or other automated system, while some forms of communication take artistic and/or entertaining forms such as television shows, movies, and theatric plays.

The development of new modes of communication are desired. Here, we describe systems and methods for achieving a new mode of communication in which the recipient of a message, signal, symbol, or other form of communication becomes aware of the message through bioTU. In alternative embodiments, brain stimulation for communication is delivered by other forms of invasive or non-invasive brain stimulation. Following is a brief and non-exhaustive list of beneficial features of a system for communication via bioTU or another form of brain stimulation: (1) New modalities of communication such as direct communication of an emotional state; (2) Communication of subjective experiences; (3) Concurrent communication of a concept and an emotional response such as a visual image of a person, place, or object and a feeling of satisfaction or desire; (4) Faster communication, for instance by communicating a higher order concept directly to the brain that would otherwise require 10 s to 100 s of milliseconds or seconds or longer for the brain to process; (5) communication that affects behavior such as brain stimulation that modulates the risk-taking behavior for a soldier or trader in the financial markets; (6) Parallel communication in multiple sensory domains that circumvents our general limitation of being able to attend to a limited number of sensory stimuli (e.g. circumventing our limited ability to listen to two spoken conversations concurrently by using brain stimulation to communicate multiple concepts at the same time); (7) private communications that cannot be eavesdropped upon; and (8) numerous additional beneficial aspects described herein that relate to entertainment, cognitive enhancement, improved decision-making, cognitive processes related to learning and memory, the quality of sleep, physiological arousal, sexual arousal, attention, mood, emotions, creativity, and other applications.

The inventions described herein relate to methods and systems for neuromodulation that serves as a form of communication. The method and system for communication by neuromodulation involves four core steps:

A message is generated by an individual (601, 801, FIGS. 6 and 8) or automated system (1002, 1014, 1101, FIGS. 10 and 11);

A message is transmitted to a computer processor unit (602, 802) that translates the message into a brain stimulation protocol appropriate for communicating the message (603, 604, 803, 804). For instance, a one-word message of 'happy' may be translated to a neuromodulation protocol that induces a subjective feeling of improved mood. In other embodiments, the brain stimulation may relate to the message indirectly, as for a message sent by Morse code. One advantageous feature of the system for transmitting and translating a message from a sender to a recipient is a personalized database (605, 606, 805, 806) or one that can be updated to improve the quality of translation based on feedback from users (905, 906, 907, 908, 909).

Next, an instruction is transmitted to a device that delivers neuromodulation stimuli that is near or wearably attached to the recipient of the message (607, 807). FIG. 8 shows systems and methods for communicating via bioTU, while FIG. 6 shows systems and methods for communicating via alternative methods of brain stimulation that may be of limited utility relative to bioTU for communication.

At the instructed time, a bioTU protocol is delivered to stimulate the targeted region of the brain in order to activate, inhibit, or modulate its activity (608, 808) and induce an altered subjective experience or cognitive state for the user (609, 809). Specific embodiments of neuromodulation are described herein and include stimulation targeting primary sensory cortex, primary and secondary motor cortex, association cortex (including areas involved in emotion, executive control, language, and memory), neuromodulatory pathways, the amygdala, the hippocampal formation, and other brain regions. The message may affect one or more of the attentional state (610, 810), emotional state (614, 814), or cognitive state (615, 815) of the recipient. Alternatively, the message may cause one or more of the following effects: the recipient may act based on an instruction contained in the message (611, 811); the recipient may experience a state of physiological arousal (612, 812); the recipient may perceive a sensory stimulus (613, 813).

In a common embodiment of the invention, a relational database, lookup table, or other storage system is created that includes parameters for brain stimulation appropriate for a particular technique of neuromodulation, a target brain region, and an intended effect on the brain of the recipient (603, 604, 803, 804). The database may include protocols for activation of multiple brain regions concurrently or with a specified temporal delay. The relational database may be dynamic and capable of modification based on feedback from users, manual modification by a skilled practitioner of brain stimulation techniques, or other automated or semi-automated algorithms. The relational database may exist on a device near or wearably attached to the sender of a message, on a device near or wearably attached to the recipient of the message that may include devices for brain stimulation, or in a remote location on a server operated by a company, government agency, military force, first responder department, or community group. The database may also exist in multiple copies at a plurality of locations.

An important feature of communication by brain stimulation is that a message is generated by one individual, group of individuals, or automated/computerized service, then transmitted to the recipient of the message by wired or wireless means known to those skilled in the art (607, 807). In some embodiments, the message is sent directly to the brain stimulation device near or wearably attached to the user or implanted in the user.

In the embodiment of the invention whereby the database is stored on a remote server, communication via the Internet or dedicated transmission network is used to transmit to and from the sender and recipient of the communicated message. In some embodiments, the content of the database may be general and unspecialized such that all messages are associated with a single brain stimulation protocol. In this simple design, a message serves as a trigger for a fixed neuromodulation protocol. In other embodiments, the content of the database may associate each message with a specific bioTU protocol for brain stimulation.

Feedback about the efficacy of neuromodulation can be used to modify and improve the quality of message translation by the relational database. In a related embodiment of the invention, the effect of a particular brain stimulation protocol on the recipient is assessed to determine whether the intended effect was achieved or message was communicated successfully. The determination of successful brain stimulation for the intended message can be done manually by feedback from the message recipient for instance by pressing a button on the device, sending an email to the message sender, or by making a selection in a computer, mobile device, or web-based application. In some embodiments of the device, the feedback signals are stored locally for some period of time for instance on a memory storage device and transmitted to the remote server at a later time. Upon receiving an update from the device, software running on the remote server adjusts the relational database or statistical and analytical algorithms used to determine which stimulation protocol should be used for a particular message.

In one specific embodiment shown in FIG. 9, feedback is provided to the sender. One form of feedback indicates whether an acceptable translation of the intended message to a bioTU protocol was identified and thus whether the bioTU message was transmitted. A second form of feedback is directed at the relational database that translates a message into an appropriate bioTU protocol and provides feedback concerning whether the intended message was successfully received by the recipient. A message is generated by a sender (901, FIG. 9), transmitted to a remote server (902), and compared to a relational database on the remote server (903). If the message content matches a database entry (904), the bioTU protocol is transmitted to the recipient's bioTU device (910). If there is no exact match in the database (905), natural language algorithms and/or statistical processing algorithms are applied to the message to identify an appropriate bioTU protocol (906). If an acceptable match is identified based on these algorithms (907, 908), the bioTU protocol is transmitted to the recipient's bioTU device (910). If no acceptable match is identified, the sender is informed that the message was not sent (909). If an acceptable bioTU protocol has been transmitted to the recipient's bioTU device, the bioTU protocol is delivered to the recipient (911) and the recipient receives the message (912). Next, a system determines whether the intended message content or effect was achieved in the recipient (913, 914) and feedback concerning the quality of bioTU is transmitted to the relational database (916). Based on this feedback, statistical or other algorithms can be used to update, modify, or otherwise improve the relational database (915). In some embodiments of the invention, feedback concerning whether the intended message content or effect was achieved in the recipient is also transmitted to the sender.

In other beneficial embodiments, the effect of neuromodulation can be measured by using a device near, wearably attached to, or implanted in the recipient. In this embodiment, the feedback concerning the quality of brain stimulation can be transmitted to the relational database without any input by the recipient. Upon receipt of the feedback, an algorithm is applied that determines how—or if—to integrate this feedback into the database so that translation of a message in the future is modified to better achieve the desired effect on the recipient—or another individual—of the message. In another embodiment, the database is personalized for an individual user, group of users, or demographic group defined by age, sex, race, nationality, cognitive ability, neuroanatomy, or other useful categorical variable known to those skilled in the art. In yet another embodiment, the database maintains a record of brain stimulation protocols delivered to a particular user as well as the messages sent by a specific individual or automated communication system. The data concerning neuromodulation effects can be used for research purposes, for improving the quality of brain stimulation, sold to third parties, or for other uses.

The database may include functionality to process the content of the message using computational linguistic or other beneficial algorithms to determine the intended meaning of the message (606). Specific embodiments of computational linguistic algorithms include natural language processing, automatic summarization, coreference resolution, discourse analysis, machine translation from one language to another so that messages can be compared across languages (e.g. similar to Google translate), part-of-speech tagging, parsing, question answering, relationship extraction, sentence breaking, sentiment analysis to determine emotional valence and intensity, topic segmentation, and word segmentation. In one such embodiment, a natural language processing algorithm determines the intended meaning of a message so that it can be mapped to a specific brain stimulation protocol contained in the database. In some embodiments, any number of statistical frameworks may be included for improving the quality of the translation of a message to a brain stimulation protocol using bioTU or another method of brain stimulation.

Messages to be communicated by the system can be generated in ways that are well known in the art. Specific embodiments include methods for a user to create a message through speech, written language, selection of a message from among a pre-populated set of possible messages, or other method for a user to generate an instruction or signal. Alternative embodiments use automated generation of message content. Specific embodiments include content chosen automatically by a computerized system or website that relate to content of particular interest to a user. An additional set of advantageous embodiments use techniques well known in the art for measuring the physiology of an individual human or animal including techniques for measuring brain activity. These measurements can then be translated into an appropriate brain stimulation protocol to be delivered to the individual from which the measurement was made. In this way, an individual can receive a message that provides information related to an aspect of brain function that is not otherwise knowable consciously. In another embodiment, the measurements are used for communication via neuromodulation to another individual. In this way, automated communication occurs between the brain of one individual and the brain of another individual. These specific embodiments will be described in greater detail below.

The message sender may enter the message into dedicated hardware for the brain stimulation communication device using a computer interface. Alternatively, the dedicated device may be a mobile device such as a smartphone, tablet, handset, smartwatch, smartband, or other interactive computing device. The message may also be entered using a custom 'app' for a mobile device such as a smartphone. Additional beneficial features may include a message to be generated by voice, hand signal, or other movement. The device can be designed to communicate with other devices in a wired or wireless fashion. Communication may be made with devices and controllers onboard or remotely located using methods known in the art, including but not limited to, RF, WIFI, WiMax, Bluetooth, UHF, NHF, GSM, CDMA, LAN, WAN, or TCP/IP.

Other methods for manual input of a signal include communication by email, text message, instant message, Twitter message ('tweet') or other messaging system, a post written on an online forum or social media site such as Facebook or mySpace, spoken language that is processed by a speech recognition system, writing a letter that is scanned by a remote service and converted to machine-readable text via optical character recognition (OCR), or other forms of verbal or non-verbal communication that may be known by one skilled in the art.

In an embodiment, a message is generated and/or received by a participant in a Massively Multiplayer Online Role-Playing Game (MMORPG) (such as World of Warcraft or Age of Conan) or online action game (such as Halo or Call of Duty). In an embodiment, a MMORPG, online action game, or other game played on a computerized system is the sender of an automated message to a participant for communication by neuromodulation.

In another embodiment, a message is generated automatically. In specific embodiments, the signal may be generated by a computer system or website. For instance it is well known in the art how to create a news feed on a particular topic that is sent to a user on a regular basis. Another well-known embodiment for automatically generating content is an RSS (Really Simple Syndication) feed that sends updates on a particular topic or from a particular individual, group, or service to a user. For instance, a user can receive updates about financial news. Other methods of automatically generating content are well known in the art and include automated email or text messages for instance to report the weather for the day or traffic for a morning commute.

In another embodiment for content generation, a device and system are used to automatically detect brain signals or other physiological measurements in order to generate a message. Physiological measurements may include electromyogram (EMG), galvanic skin response (GSR), heart rate, blood pressure, respiration rate, pupil dilation, eye movement, gaze direction, or other physiological measurement. A simple ohmeter is effective for measuring skin conductance for assessing the galvanic skin response. A small current is passed between two leads placed near each other on the skin and the conductance is measured. Blood pressure, body temperature, and heart rate can be measured using a sphygmomanometer, thermometer, and pulse oximeter, respectively. These various measurements can be decoded to determine a cognitive state, sleep state, physiological state, or thought, sensory perception, emotion, concept, or state of physiological arousal, sexual arousal, or attention. The decoded brain state can then be communicated to a recipient via brain stimulation so that the recipient shares an experience of another individual. Brain activity can be recorded non-invasively by one or more techniques chosen from electroencephalography (EEG), magnetoencephalography (MEG), functional magnetic resonance imaging (fMRI), functional near-infrared spectroscopy (fNIRS), positron emission tomography (PET), single-photon emission computed tomography (SPECT), computed tomography (CT), functional tissue pulsatility imaging (fTPI), or other techniques for measuring brain activity known to one skilled in the art.

One specific embodiment of a system that automatically detects brain activity or other physiological signals generates a message to be communicated via bioTU intended to provide feedback about the measured physiological signal in order to achieve a desired value or range of the physiological or brain signal (FIG. 10). A message is generated based on one or more methods for recording of brain activity (1002) or other physiological measurement (1014) as described in the paragraph above. Monitoring of brain activity and/or other physiology continues (1006) until at least one of these measured parameters is detected to be outside a desired value or range (1003, 1004, 1006). In some embodiments, the measured physiological signal is transmitted to a relational database (1010) and memory storage unit (1009) that stores some or all of the physiological data and the message to be communicated. The database and memory storage may be remote (1005, 1007, 1008) or a component of the device wearably attached to the recipient. The appropriate bioTU protocol for inducing the physiological signal toward a desired value or range is determined (1011). This appropriate bioTU protocol is transmitted to the bioTU device (1012) and delivered to the brain (1013).

In some embodiments of the invention, brain stimulation protocols are pre-determined. These embodiments include applications for entertainment, marketing, or to communicate another aspect of the location or behavioral state of an individual. For entertainment applications, a movie, game, or theme park ride can be designed to include communication via brain stimulation. In these embodiments, brain stimulation can be used to enhance the immersiveness of the entertainment experience. In one specific embodiment, communication by brain stimulation can be used to otherwise modify the entertainment experience. For instance, in a gaming environment, brain stimulation can be used to modulate the attention of the gamer to alter the difficulty of gameplay. Neuromodulation that enhances attention may make gameplay easier while forms of neuromodulation that reduce attention may make the gameplay more difficult and challenging for the user. Effective performance in other types of games may be enhanced by increased creativity that may occur concurrently with neuromodulation that causes reduced attention. Alternatively, signals related to the gaming experience can be transmitted directly via brain stimulation rather than by sight or sound. Brain stimulation targeted to primary somatosensory cortex can be used to deliver stimuli that are perceived by the gamer as a touch on the shoulder. Stimulation in other portions of somatosensory cortex can transmit a sense of touch or other perception related to a specific part of the body according to the somatosensory homunculus known by those skilled in the art. Alternatively, communication via bioTU can be used to enhance the immersiveness of a movie, television show, or theme park ride.

One beneficial feature of communication via bioTU or other forms of brain stimulation relates to the various ways that individuals and groups can communicate. In one embodiment of the invention, communication is one to one between two individuals (FIG. 7). This form of communication can be unidirectional with messages sent by one individual and received by a second individual via bioTU. In another embodiment, communication between two individuals can be bidirectional with responsive communication as occurs during a conversation using spoken language or a written email exchange. One embodiment of communication via bioTU between two individuals is schematized in FIG. 7. The system is designed so that one or both of a first individual (701) and a second individual (710) may generate a message to be communicated to the other individual via bioTU. In one embodiment, the first individual (701), generates a message (702). The message may be generated by any or all of the methods described herein, including written and verbal communication, and direct readout of brain activity or other physiological measurement. A relational database translates the message into an appropriate bioTU communication protocol. Depending on whether the relational database is stored on a remote server or a component of the bioTU device wearably attached to the recipient (703, 704), the message may be transmitted to a remote server (706) before determining the appropriate brain stimulation protocol to deliver (705). Next, the appropriate bioTU protocol is transmitted to the recipient's bioTU device (707) for delivery of the bioTU protocol (708). Upon receiving the message (709), the recipient (710) may choose to generate another message (a response) that is transmitted via similar systems and methods (711, 712, 713, 714, 715, 716, 717) to the first individual (701).

In another embodiment, communication is delivered from one individual to many individuals, as may be advantageous for communication between a teacher and students. In yet another embodiment, communication is delivered from many individuals to one individual, as may occur from a team of soldiers all reporting to a commanding officer. In another embodiment, communication is delivered by a group of two or more individuals to all or a subset of the members of the same group, as may occur when a group of friends sends messages among themselves to share their daily experiences. In another embodiment, communication is delivered by a group of two or more individuals to a second group of individuals that includes individuals not part of the group sending the messages. This embodiment would permit a new type of group interaction as could occur between fans of two competing sports teams for communicating the emotional intensity of the fan experience during the course of the game or event.

Communication may occur synchronously such that the bioTU protocol delivers a communicated perception immediately following the generation of the message. In another embodiment, communication occurs asynchronously. A message is generated by a sender at one point in time and delivered at a future time or a plurality of future times.

Brain Stimulation to Communicate Realistic Virtual Experiences

Brain stimulation can be used to communicate realistic virtual experiences. Communication is limited by its form and may be incapable of reproducing a particular subjective cognitive state or perception. For instance, a written description of the smell of freshly baked cookies cannot fully reproduce the subjective experience of smelling fresh cookies themselves. The communication of a particular subjective experience can be induced or triggered by activating neuronal circuits in similar patterns as would occur for the experience itself. bioTU is particularly well-suited to this application due to its capacity for targeting, as well as the possibility of using multiple transducers in an array to create a complex spatiotemporal pattern of neuromodulation. Beneficial embodiments would target one or more brain regions that mediate sensory experience, motor performance, and the formation of ideas and thoughts, as well as states of emotion, physiological arousal, sexual arousal, attention, creativity, relaxation, empathy, connectedness, and other cognitive states. To achieve a suitably realistic virtual subjective experience, delivering bioTU to modulate neuronal activity underlying multiple sensory domains and/or cognitive states concurrently or in close temporal arrangements would be beneficial. Moreover, an additional beneficial embodiment of a device for virtual subjective experience would include devices or systems to record the brain state of an individual in order to re-create that subjective experience in that individual or another individual at a later time or concurrently.

Communicating virtual subjective experiences via bioTU would be desired for a wide variety of subjective experiences. An individual may wish to re-experience a significant moment in his or her life such as the birth of a child or receiving an award. Alternatively, an individual may wish to re-create the subjective experience of youthful exuberance or contented wisdom from another time in their lives. In some embodiments, a virtual subjective experience would be advantageous for psychiatric, behavioral, or occupational therapy. By briefly creating a controlled, alternative subjective experience, the subject could benefit by learning how to control their own brain states to achieve a similar therapeutic effect. A similar, albeit simpler, technique has been used to provide biofeedback to patients with chronic pain regarding the activation of a pain processing brain region in the rostral anterior cingulate cortex.

Embodiments of virtual subjective experiences created via bioTU neuromodulation would also be beneficial for generating novel experiences for an individual for entertainment, training, or other purposes. Virtual subjective experience would provide a high level of immersiveness for gaming, movie, or theme park applications. In another embodiment, individuals may be entertained by the subjective experience of climbing Mt. Everest, dunking a basketball like LeBron James, receiving a raucous standing ovation as a musician, or innumerable other interesting or entertaining experiences. In other embodiments, virtual subjective experiences may be designed for training purposes such as for training soldiers, firefighters, or trauma surgeons for situations that would be otherwise difficult or dangerous to create or reproduce.

In yet another embodiment, one individual communicates one or more aspects of their subjective experience to a friend, loved-one, doctor, psychiatrist, or coach such that the recipient may better understand their feelings, thoughts, or subjective experiences. In one such embodiment, an individual receives the virtual subjective experience of having a neurodevelopmental, neurodegenerative, or psychiatric disorder so as to better understand that condition. Specific embodiments of this application include virtual subjective experiences of having Autism spectrum disorder, Down syndrome, Alzheimer's disease, schizophrenia, or another disorder or pathological behavioral or cognitive state. In this way, individuals such as teachers, caretakers, or colleagues of an individual with such a condition could increase their empathy for the individual by better understanding their subjective experience. In yet another set of embodiments, the virtual subjective experience gives the individual a feeling of being drunk or high on drugs without the dangerous side effects of the compounds that induce these cognitive states.

In yet another embodiment, communication via bioTU or another form of brain stimulation provides a novel mechanism for sensing the user's environment. For instance, an infrared-sensitive camera affixed to the user's head can be used to identify objects in the user's environment based on their heat signature and this information can be communicated to the user via bioTU to visual cortex or a higher visual processing brain region. In alternative embodiments, sensors can be used to communicate in the context of other sensory modalities not normally transduced by human sensory systems such as acoustic waves outside the normal hearing range, wavelengths of light outside the normal range of sight, new senses such as an embodiment to communicate the presence and nature of magnetic fields, or other aspects of a user's environment not otherwise detectable by sensory transduction systems directly. In some embodiments, communication via bioTU can effectively compensate for a sensory deficit such as color blindness, high frequency hearing loss, or another form of sensory deficit.

FIG. 11 shows a system to achieve specific embodiments in which information is communicated about a user's environment that cannot be detected by normal sensory transduction pathways. One or more techniques are used to monitor the user or his/her environment (1101) that may include one or more of a microphone, video camera, accelerometer, thermometer, sensor for a volatile compound, radiofrequency sensor, magnetic field sensor, or other useful device or sensor. Data from these sensors is transmitted to a processor unit that may be on a remote server or a component of a bioTU device (1102). The data are appropriately processed to derive useful information, translated to a bioTU protocol, and transmitted by wired or wireless connection to a bioTU device (1103) for delivery of a bioTU protocol (1104) to the user or recipient (1105).

Beneficial embodiments of communication via bioTU or another form of brain stimulation involve the communication of words, instructions, or concepts. In some embodiments, bioTU can be used to transmit to a recipient a word, instruction, or concept directly. In other embodiments, the recipient is trained to associate a particular spatiotemporal pattern of bioTU stimulation with a specific word, instruction, or concept. In yet another embodiment, bioTU stimulation is used to transmit a new language. The term language refers to a symbolic framework of communication. Differences in structure and lexicon among different languages account for differences in communication that can be difficult to translate such as idiomatic expressions. Accordingly, development of a language in which words and concepts are transmitted directly to the brain could provide new richness to verbal communication by associating a particular word or concept with brain regions that mediate particular sensory perceptions, emotional responses, or other cognitive states.

The use of bioTU or another brain stimulation technique to communicate symbolic concepts such as words and instructions offers various advantages. Communication frameworks that permit private communication without the possibility of eavesdropping would be advantageous in military, intelligence, and first responder applications. Direct brain stimulation permits private communication of an instruction or signal that can evade unwanted detection by a third party as would otherwise be possible for a message conveyed by verbal, written, or hand signaling routes. Coded messages can be delivered that induce a particular cognitive state or communicate a specific message based on previous training or learning. Such coded messages could be designed to be meaningless if delivered to an individual other than the recipient. Another advantage of linguistic content transmitted directly to the brain via bioTU is the potential for creating a common bioTU code that translates between different languages such as French and English.

In some embodiments, a recipient will require training—just as for learning any new language—to understand the words, instructions, or concepts delivered via bioTU. In other embodiments, the bioTU stimulation induces subjective recognition or virtual experience of the appropriate words, instructions, or concepts without training In written language, words are distinguished by the order and content of letters. In spoken language, words are distinguished by a specific arrangement of phonemes and context. In sign language, words are represented by the position and movement of hands and arms. For communication via bioTU or another form of brain stimulation, specificity of words, instructions, or concepts can be achieved by varying one or more of parameters of bioTU stimulation including brain region or regions targeted, ultrasound intensity, ultrasound acoustic frequency, pulse repetition frequency, cycles per pulse, pulse length, or the pattern of modulation of any of the preceding parameters during a bioTU protocol. An important feature of the bioTU parameters is to induce neuromodulation that is distinguishable by the recipient for distinct words, instructions, or concepts. Various brain regions could be targeted by bioTU for communication of words, instructions, or concepts, including but not limited to: various portions of somatosensory or primary motor cortex that represent distinct portions of the periphery, auditory cortex, visual cortex, other cortical regions, or other non-cortical regions such as the amygdala, hippocampus, thalamus, cerebellum, or other brain region.

In alternate embodiments, the complexity of the linguistic communication can vary considerably. In simple embodiments, a recipient receives a "yes" or "no" instruction. In one alternative embodiment, a recipient receives an instruction to move in one of eight body-centered directions. In this embodiment, the direction the recipient is facing may be used to determine which direction to instruct for an intended movement in a compass-defined direction. In another alternative embodiment, bioTU is used to communicate more than about 10 words, concepts, or instructions; more than about 100 words, concepts, or instructions; more than about 1,000 words, concepts, or instructions; more than about 10,000 words, concepts, or instructions; or a larger number of words, concepts, or instructions.

In some embodiments, the sender generates the message using speech, written language, or other means to choose instructions or words via mobile or computer devices. In other embodiments, the message is generated by decoding brain recordings or physiological measurements from the sender. For instance, EEG brain recordings can be used to distinguish brain rhythms based on the phase and power of oscillations in particular frequency bands, the brain region that is the source location of their generation, and other metrics. In trained users, self-control of brain rhythms can be used to transmit content for communication via bioTU to a recipient. Alternatively, measurements of other aspects of physiology including but not limited to electromyogram (EMG), galvanic skin response (GSR), heart rate, blood pressure, respiration rate, pupil dilation, eye movement, or gaze direction can be used to trigger the generation of an appropriate bioTU message for a recipient.

Emotional connections and bonds of friendship, love, or respect are significant aspects of human relationships. Pair-bonding, as between a husband and wife or parent and child, is among the strongest human relationship. Empathy relates to the comprehension and understanding of the emotions, feelings, and cognitive state of another individual and underlies numerous positive aspects of human interactions. Neurobiologically, various cognitive processes related to empathy such as the capacity to recognize an emotion in others, form memories of emotions, and engage successfully in social interactions involve neuronal pathways affected by the neuropeptides oxytocin and arginine vasopressin.

Embodiments of communication mediated by bioTU or another form of brain stimulation that target pathways related to emotion and social processing would be beneficial for modulating the interaction of individuals or groups. Advantageous targets include brain regions involved in empathy and cognitive processes related to emotion and social interactions such as brainstem nuclei, hypothalamus, amygdala, anterior cingulate cortex, prefrontal cortex, ventromedial prefrontal cortex, and other brain regions involved in oxytocin and arginine vasopressin function.

Communication can be considered broadly to represent the direct activation of brain regions that underlie the subjective experience of sensory stimuli, emotions, physiological arousal, or higher-order concepts such as words or abstract ideas. The concept of communication by bioTU also includes systems and methods for neuromodulation that cause a change in behavior, physiological arousal, sexual arousal, or attention of an individual human or animal.

The capacity for targeting any brain region non-invasively is one beneficial aspect of bioTU. Due to the effective transmission of ultrasound waves through tissue, bioTU permits neuromodulation throughout the brain. Distinct brain regions are known to mediate specific cognitive functions. Other aspects of brain function are highly distributed. In various embodiments of communication systems based on bioTU, one or more brain regions may be targeted to achieve the desired subjective effect for the recipient. Various methods of targeting ultrasound are well known in the art, including focused transducers, phased arrays of transducers, and acoustic collimators.

In some embodiments of communication via bioTU, ultrasound waves are targeted to areas of the cerebral cortex. The cerebral cortex is composed of four lobes: the frontal, parietal, occipital, and temporal lobes. The frontal lobe underlies motor planning, motor control, executive control, decision-making, pain-processing, social cognition, and many other higher cognitive functions. Sub-regions of frontal cortex have been identified that underlie these and other specific processes. The parietal lobe is involved in sensory processing, some aspects of motor control such as gaze control, and a variety of other functions. The occipital lobe is primarily involved in visually processing. The temporal lobe mediates auditory processing, many aspects of language production and reception, and important aspects of long-term memory. Various regions of cerebral cortex are sensory processing areas, including: striate visual cortex, visual association cortex, primary and secondary auditory cortex, somatosensory cortex, primary motor cortex, supplementary motor cortex, premotor cortex, the frontal eye fields, prefrontal cortex, orbitofrontal cortex, dorsolateral prefrontal cortex, ventrolateral prefrontal cortex, and anterior cingulate cortex. bioTU targeted to one or more of these regions of cerebral cortex can modulate related cognitive processes or motor commands by activating, inhibiting, or otherwise modulating the function of neuronal circuits.

In other embodiments of communication via bioTU, deeper brain regions are targeted. A non-exhaustive list of brain regions that may be targeted including: the limbic system, the amygdala, hippocampus, parahippocampal formation, entorhinal cortex, subiculum, thalamus, hypothalamus, white matter tracts, brainstem nuclei, cerebellum, or other brain region. An alternative embodiment employs a strategy of targeting brain regions underlying the function of a neuromodulatory system for communication via bioTU or another form of brain stimulation. Neuromodulatory systems include those that use serotonin, dopamine, norepinephrine, acetylcholine, and other neurotransmitters.

Some forms of communication using brain stimulation such as bioTU can be achieved without targeting a specific brain region. For instance, diffuse regions of cerebral cortex have been shown to be sensitive to reward. Moreover, brain oscillations such as slow-wave, delta, beta, theta, gamma, or alpha rhythms are created by the synchronous activation of populations of neurons that may be distributed in non-contiguous brain regions. bioTU protocols designed to oscillate at frequencies consistent with a brain rhythm of interest can be targeted broadly to one or more brain regions known to mediate that form of brain oscillation. For instance, slow-wave oscillations occur in a concerted manner in regions of cerebral cortex that may be discrete or extend through an entire hemisphere. Another embodiment of bioTU to affect brain rhythms could modulate thalamocortical oscillations by targeting the thalamus, sharp-wave ripples by targeting the CA3 region of the hippocampus, or alpha waves by modulating 8-12 Hz rhythms that originate in the occipital lobe. In alternative embodiments, other brain rhythms or distributed neuronal pathways are targeted for communication by bioTU or another form of brain stimulation. For each of the targeted rhythms, bioTU may be used in some embodiments to enhance the rhythms and in other embodiments to reduce the rhythms.

DEFINITIONS

A message is defined to include instructions, words, concepts, emotions, experiences, sensory stimuli, other forms of conscious or sub-conscious experience, or alterations in behavior, physiological arousal, sexual arousal, attentional, or other cognitive state of an individual human or animal.

In this application, we use the terms 'brain stimulation', 'neuromodulation', and 'neuronal activation' interchangeably to refer to invasive or non-invasive techniques to alter the excitability, action potential rate, vesicular release rate, or other biochemical pathway in neurons or other cell types in the brain.

In this application we use the terms "bioTU", "bioTU protocol", "bioTU communication event", and "bioTU stimulation" interchangeably to refer a modulation of brain circuit activity induced by patterned, local vibration of brain tissue using US whereby:

Ultrasound is transmitted into the brain;

The acoustic frequency is generally greater than about 100 kHz and less than about 10 MHz. Particularly advantageous acoustic frequencies are between about 0.3 MHz and 0.7 MHz;

The spatial-peak temporal-average ($I_{spta}$) intensity of the ultrasound waveform at the brain tissue is less than about 1 W/cm$^2$. Advantageous $I_{spta}$ values are greater than 20 mW/cm$^2$ and less than 700 mW/cm$^2$. Particularly advantageous $I_{spta}$ values are greater than 20 mW/cm$^2$ and less than 100 mW/cm$^2$.

The ultrasound pulse length is less than about 5 seconds; and

The protocol induces an effect in one or more brain regions such as neuromodulation, brain activation, neuronal activation, neuronal inhibition, or a change in blood flow whereby heating of brain tissue does not exceed approximately 2 degrees Celsius for a period greater than about 5 seconds.

We define mechanical effects of ultrasound waves in the brain as effects caused by the local vibration of brain tissue. We define thermal effects of ultrasound waves in the brain as effects caused by the heating of brain tissue.

We define the term "pulse length" as the amount of time of a non-interrupted tone burst of one or more ultrasound acoustic wave frequency components.

We define the term "pulse repetition period" to be the amount of time between the onset of consecutive ultrasound pulses. The "pulse repetition frequency" is equivalent to the inverse of the "pulse repetition period".

We define the term "bioTU waveform" to be a period of ultrasound delivered with a pulsed or continuous wave construction that includes a specified number of pulses that may be repeated at the pulse repetition frequency. In some cases, a bioTU waveform is composed of a single continuous wave tone burst of greater than about one second that is not repeated. In such cases, the "pulse length" and "bioTU waveform duration" may be about equal.

We define the term "bioTU repetition period" to be the amount of time between the onset of consecutive bioTU waveforms. The "bioTU repetition frequency" is equivalent to the inverse of the "bioTU repetition period".

As used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. The term "treating" refers to inhibiting, preventing, curing, reversing, attenuating, alleviating, minimizing, suppressing or halting the deleterious effects of a disease and/or causing the reduction, remission, or regression of a disease. Those of skill in the art will understand that various methodologies and assays can be used to assess the development of a disease, and similarly, various methodologies and assays may be used to assess the reduction, remission or regression of the disease.

"Increase" is defined throughout as less than a doubling such as an increase of 5%, 10%, or 50% or as an increase of 1, 2, 3, 4, 5, 6, 7, 8, 9, 10, 11, 12, 13, 14, 15, 16, 17, 18, 19, 20 21, 22, 23, 24, 25, 26, 27, 28, 29, 30, 31, 32, 33, 34, 35, 36, 37, 38, 39, 40, 20 41, 42, 43, 44, 45, 46, 47, 48, 49, 50 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 400, or 500 times increase as compared with basal levels or a control.

EXAMPLES

Example 1

Communicate Instructions Privately by Delivering bioTU to a Trained Recipient

In this example, bioTU is used to communicate instructions privately to a recipient trained to associate a specific bioTU protocol targeting a brain region with a word, instruction, or concept. The targeted brain region or regions is primary auditory cortex. In man, primary auditory cortex (Brodmann's areas 41 and 42) is located in the superior temporal lobe, predominantly on the brain surface and thus readily targeted. The duration of the bioTU is chosen to be brief so that communication can occur rapidly. The length chosen is sufficient to communicate the word, instruction, or concept and is generally within a range between about 10 milliseconds and 10 seconds. In an alternative embodiment, the number of messages that can be transmitted is increased by varying the intensity, duration, or targeted brain region of bioTU neuromodulation. A further level of privacy for communication can be achieved by using a physiological measurement to generate the message such as EEG recordings of alpha rhythms.

Communication frameworks that permit private communication without the possibility of eavesdropping would be advantageous in military, intelligence, and first responder applications. Direct brain stimulation permits private communication of an instruction or signal that can evade unwanted detection by a third party as would otherwise be possible for message conveyed by verbal, written, or hand signaling routes.

A key feature of a system for transmitting an instruction or other simple message by brain stimulation is a known association by the recipient of the correspondence between brain stimulation at a particular site or with particular temporal or intensity characteristics. In this way, a code is developed that relates a concept, word, or instruction with a protocol for brain stimulation. Using the pre-determined code, the recipient of the bioTU-mediated message is trained to associate a particular word, concept, or instruction with a specific sensory perception or other alteration of cognitive state that can be detected by the recipient.

In one simple version of this communication system, "yes" or "no" instructions are communicated by bioTU delivered through one bioTU ultrasound transducer targeting primary auditory cortex (approximately Brodmann's areas 41 and 42 in the ventral portions of the temporal lobe). Various strategies are possible for creating two distinguishable auditory perceptions that correspond to "yes" and "no". Auditory cortex has a tonotopic arrangement, so two nearby transducers can be used to transmit bioTU signals that are perceived by the recipient as sounds with distinct frequencies. A second alternative is to use two distinct bioTU protocols via a single transducer that differ in duration or intensity. A third alternative is to use bioTU transducers targeting auditory cortex bilaterally such that brain stimulation delivered to each side of the brain represent "yes" and "no" messages respectively.

By increasing the number of transducers targeting different regions of the brain, such as visual, auditory, somatosensory, or motor cortex, a larger number of distinct bioTU stimulation patterns can be distinguished by the recipient, thus enabling a larger vocabulary of words, concepts, or instructions to be transmitted. For bioTU communication systems with n transducers and a single stimulation protocol per transducer, $2^n$ distinct messages can be delivered simply by turning a particular transducer on or off. By varying the stimulation parameters for each transducer, the number of messages can further increase. By varying the length of bioTU stimulation (e.g. short (less than about 1 second) and long (greater than about 2 seconds)) and the intensity of acoustic waves delivered (e.g. strong, weak, and off), the number of messages would scale by $6^n$ for n transducers.

In an embodiment that employs a phased array of ultrasound transducers, a single phased array can be used to focus ultrasound energy at more than one location at a time and/or to generate a spatial pattern of stimulation that sequentially targets different brain regions. In this way, a distinct message can be recognized by a recipient based on the set of brain regions targeted in a similar way that the meaning of a sentence composed of words depends on the choice and order of words used.

In an embodiment, larger numbers of unique messages can be transmitted by increasing the number of distinct values for a particular waveform parameter. For instance, instead of having three levels of acoustic intensity (strong, weak, and off), messages can be generated by delivering ultrasound energy at a larger number of levels of acoustic intensity. In various embodiments, the number of levels can be greater than 3, greater than 4, greater than 5, greater than 7, greater than 10, greater than 15, greater than 20, greater than 25, greater than 50, greater than 100, greater than 1000, greater than 10000, or a larger number of levels up to the number that can be distinguished by a recipient with an appropriate level of reliability.

In some embodiments, larger numbers of unique messages can be transmitted by varying additional parameters of the ultrasound waveform transmitted, including: pulse repetition frequency, acoustic frequency, waveform length, and amplitude modulation frequency. In some embodiments, different temporal patterns of variation of one or more ultrasound waveform parameters are used to transmit different messages. Time-varying patterns of one or more ultrasound parameter can be arbitrary or not, including but not limited to, sine, square, sawtooth, triangle, ramp, and spike patterns. The varied ultrasound parameter can be one of: acoustic intensity, acoustic frequency, pulse repetition frequency, pulse length, waveform length, amplitude modulation frequency, or other parameter.

In an embodiment, a component of a message is variation of one or more waveform parameters at an endogenous brain rhythm frequency to modulate brain rhythms in order to change cognitive state and achieve the communication of a message. Brain oscillations such as slow-wave, delta, beta, theta, gamma, or alpha rhythms have well-known frequency ranges. These ranges can vary between individuals. In some embodiments, EEG or another brain recording technology is used to determine an individual's frequency range for a particular brain rhythm. In some embodiments, a brain rhythm is triggered or enhanced by modulating ultrasound stimulation at an appropriate frequency. In other embodiments, a brain rhythm is disrupted, phase-shifted, or reduced in amplitude by ultrasound neuromodulation as part of a message.

A further level of privacy for communication can be achieved by using a physiological measurement to generate the message. Alpha brain rhythms (~8-12 Hz) can be monitored with electroencephalography (EEG) and predominantly originate from the occipital lobe during wakeful relaxation with closed eyes. A trained operator can control the power of alpha rhythms and use the level of power in the alpha frequency band to determine whether a "yes" or "no" message is sent. The messaging system can be activated by blinking the eyes a specified number of times and detecting these blinks via electrodes mounted on the forehead. Once the messaging system is activated, the sender of a message generates a high level of alpha rhythms for a "yes" signal and a low level of alpha rhythms for a "no" signal. The message is decoded by processing the EEG signal for power in the alpha band and transmitting the content of the message (yes' or 'no') to the bioTU device worn by the recipient as described above.

Example 2

Verbal Communication by Delivering bioTU in a Pattern that Corresponds to Morse Code In this example, bioTU is used for verbal communication based on Morse code. The targeted brain region is primary somatosensory cortex that represents haptic input to the right shoulder by targeting a medial portion of the pre-central gyrus in the left hemisphere. Most of this portion of somatosensory cortex is located directly under the skull, so the bioTU waveform needs to be delivered to a depth less than 1 cm. Two brief but distinguishable durations of bioTU are chosen to represent the "dash" and "dot" of Morse code. The short bioTU protocol is within a range between about 10 milliseconds and about 100 milliseconds. The long bioTU protocol is within a range between about 200 milliseconds and 300 milliseconds. Alternative bioTU durations may be beneficial in some embodiments. The short and long protocols are repeated according to the Morse code pattern of the message with bioTU protocols delivered at a frequency in a range of about 1 to about 20 Hz depending on the length of the "dash" and "dot" stimuli and the pattern of the message.

An extensive vocabulary of communication can be transmitted by using a coding system such as Morse code. The International Morse Code encodes the Roman alphabet, the Arabic numerals and a small set of punctuation and procedural signals as standardized sequences of short and long signals called "dots" and "dashes" respectively. Each character (letter or numeral) is represented by a unique sequence of dots and dashes. The duration of a dash is three times the duration of a dot. Each dot or dash is followed by a short silence, equal to the dot duration. The dot duration is the basic unit of time measurement in code transmission. Morse code can be transmitted by a single bioTU transducer that emits long and short pulses of brain stimulation targeted at sensory cortex such as somatosensory cortex. In one version of the device, the transducer can be targeted at the portion of primary somatosensory cortex that represents haptic input to, for instance, the right shoulder by targeting a medial portion of the pre-central gyrus in the left hemisphere. However, alternative embodiments that communicate to other portions of somatosensory cortex would also be beneficial.

Similar to an individual learning to read Morse code transmitted by flashes of light or tones, the recipient is trained to comprehend a Morse code message transmitted by bioTU. Once the recipient is sufficiently trained, a message can be sent to a bioTU device worn by the recipient that translates the text message to Morse code. A well-trained recipient may be able to comprehend a message with minimal attentional resources, permitting the recipient to attend to other visual, auditory, or tactile stimuli while receiving the message.

Morse code is designed for transmission using a single signaling source and thus requires the length of a flash, tone, or signal to vary in length to distinguish between "dots" and "dashes". An alternative embodiment of communicating verbal content via bioTU-mediated Morse code uses two transducers targeting separate areas of the brain such as bilateral somatosensory cortex corresponding to haptic sensation of the leg. The recipient is trained to associate stimulation on one side of the body as a "dot" and the other side of the body as a "dash". In practice, each stimulation can be short, meaning more information can be transmitted per unit time.

Example 3

Communicate the Visual Perception of a Color or Moving Visual Percept by bioTU Stimulation of Extra Striate Cortex In this example, bioTU is used to communicate the visual perception of a color or moving visual percept. In one embodiment, a visual perception is induced in a particular area of visual cortex to transmit a message related to a position in head-centered space. In a second embodiment, the color of light perceived is associated with a specific message. Ultrasound transducers target one or more brain regions and a bioTU protocol for activating the targeted brain regions is chosen. The targeted brain region is extra striate visual cortex, also referred to as visual association cortex. In man, visual association cortex is located in the occipital cortex anterior, lateral, ventral, and dorsal from the occipital pole. Although most of extra striate cortex is located directly under the occipital bone, some portions are wrapped between the hemispheres and thus require targeting at a greater depth of 1 to 8 centimeters. The duration of the bioTU protocol is chosen to be within a range between about 10 milliseconds and about 1 second or longer.

Regions of cerebral cortex in and near the occipital lobe process low-level aspects of visual stimuli such as movement, color, and edges. bioTU targeted to cortical areas involved in the early processing of vision can be used to communicate subjective experiences of visual stimuli without activating the normal visual transduction pathways through the eyes, optic nerve, and thalamus.

The functional organization of visual cortex has been elucidated based on electrophysiological and functional magnetic resonance imaging (fMRI) methods. The existence and anatomical locations of multiple retinotopic maps in visual cortex of humans and animals is well-known and permits targeted brain stimulation to induce visual percepts.

Electrical stimulation of extra striate visual cortex induces visual percepts related to color or movement in man. Farrell and colleagues studied 15 patients with subdural grids and strips implanted for medically intractable epilepsy in a location favorable to the study of the visual cortex by direct brain stimulation (Farrell et al., 2007). These invasive studies were used to map the source of seizures for subsequent surgery and resection and were thus invasive in nature with high risk for infection and pain.

Electrical stimulation of extra striate visual cortex produced visual percepts of points of light, colors, and moving objects. Subjects perceived flashing lights for electrical stimuli targeting visual association cortex. Colored circles (and, in some cases, halos of different colors around them) were induced by electrical stimuli targeting the posterior peri-calcarine cortex, the occipital pole, and the inferior occipital cortex. Moving objects (most commonly lights) were reported by subjects in response to stimulation of the visual association cortex and often induced a head movement in the direction of the moving light.

bioTU targeted to visual cortex offers a safe alternative for activating the visual system and thus communicate visual information in a private, direct, and controlled manner. bioTU transducers are attached to the skull coupled to the occipital bone or adjoining areas of the skull and targeted to the appropriate regions of visual cortex. bioTU targeted to one hemisphere induces visual percepts in the contralateral visual field. The perception of a color, moving light, or flash of light can be achieved by targeting to the appropriate region of visual cortex.

Personalization of targeting can be achieved for an individual in a testing session in which a target percept is indicated to the recipient (e.g. a color or a point of light moving in a particular portion of visual space with a particular velocity) and the positioning or targeting of a bioTU transducer is shifted until the intended percept is achieved in response to bioTU stimulation. The targeting for a particular percept can then be stored in a database so that the brain region can be targeted later in the same individual.

One potential application for communication of low-level visual percepts by bioTU is to instruct the recipient of a message to shift their gaze in order to attend to an object in a particular portion of the visual field. Attention is known to relate to the direction of gaze. The recipient has a pair of bioTU transducers mounted near the rear of the head for targeting visual association cortex on each hemisphere. The sender of a message desires that the recipient look at an object to their right and sends an instruction that is transmitted to the recipient's bioTU device and generates appropriate ultrasound waves to activate visual association cortex in the left hemisphere. The recipient perceives a movement in the recipient's right visual field and the recipient consciously or unconsciously shifts gaze to the right. Similarly, an instruction to look to the left provides bioTU directed to the right visual association cortex and induces a shift in the recipient's gaze to the left.

A second potential application uses a pair of ultrasound transducers to induce visual percepts of white and colored light. One ultrasound transducer targets visual association cortex for inducing a percept of a static, flashing, or moving white light. A second ultrasound transducer is positioned to induce visual perception of a colored light by targeting the posterior peri-calcarine cortex, the occipital pole, or the inferior occipital cortex. Each of the transducers are positioned to ensure targeting that achieves the desired visual effect. An individual sends a message to the recipient to communicate "white" or "color". The message is transmitted to the recipient's bioTU device and the appropriate ultrasound transducer is used to induce a visual percept that is white or colored.

Example 4

Communicate a Motor Command by Stimulating Primary or Supplementary Motor Cortex In this example, bioTU is used to communicate a motor command by stimulating primary or supplementary motor cortex. The targeted brain region is one or more brain regions chosen from primary motor cortex (M1), the supplementary motor area (SMA), or the premotor area. In man, M1 is located in the posterior frontal lobe along the pre-central gyrus. SMA and the premotor area are anterior to M1. The duration of the bioTU protocol is chosen to be within a range between about 10 milliseconds to about 5 seconds.

In some cases the bioTU protocols are delivered to multiple areas of motor cortex with a temporal offset of 10 milliseconds to 1 second to cause (or induce the subjective experience of) a sequence of movements with intervals chosen within a range of about 1 second to about 1 minute or longer.

bioTU can be used to communicate simple or complex motor commands via ultrasound brain stimulation to the appropriate regions of primary and supplementary motor cortex, respectively.

In man, M1 is located in the posterior frontal lobe along the pre-central gyrus. Stimulation of corticospinal neurons that originate in M1 with electrodes or transcranial magnetic stimulation induces movement of body parts in a somatotopic order and may also induce a desire to move or somatic sensations. Lesions to M1 cause contralateral paralysis. M1 is organized in a somatotopic manner for different body parts in an arrangement called the motor homunculus. Body areas for which fine motor control is possible such as the hands and face comprise large areas of M1, while body areas limited to more coarse movements such as the legs and trunk are represented by smaller areas of M1. The somatotopic arrangement of M1 permits targeting of brain stimulation for inducing specific movements. For instance, the most medial portions of the pre-central gyrus control the legs, trunk, and shoulders. More laterally, there are larger brain regions representing the hands, fingers, face, and lips.

SMA and the premotor area are anterior to M1 and implicated in motor planning and execution of complex movements. In non-human primates, stimulation of SMA generates multi-joint movements such as reaching. Electrical stimulation of the premotor area or SMA induces movement without awareness in man. Other reports suggest that electrical stimulation of the pre-motor area can induce speech arrest.

Movements can also be induced by electrical stimulation of motor nerves, muscles, or spinal ganglia. In contrast to these methods for eliciting movements, stimulation of primary motor cortex can induce an additional subjective somatic sensation of movement as has been shown via transcranial magnetic stimulation (TMS).

In one example embodiment of communication by bioTU stimulation of motor cortex, bioTU ultrasound transducers are placed bilaterally above M1. Each transducer is directed to an intermediate mediolateral portion of the precentral gyrus to activate descending corticospinal axons that project to the musculature of the hand. The sender of a message intends to communicate a message to the recipient by causing movement of one or both of the recipient's hands. This embodiment could facilitate communication by the sender to a third party via a movement induced in the recipient. In another embodiment, communication by bioTU causes a modulation of a self-generated movement.

Example 5

Communicate Touch to the Lips or Mouth by bioTU Stimulation

In this example, bioTU is used to communicate the subjective experience of touch to the lips and/or mouth. The targeted brain region or regions is chosen from the somatotopic area relating to the mouth and lips either unilaterally or bilaterally of primary motor cortex (M1), primary somatosensory cortex (S1), or both. In man, M1 is located in the posterior frontal lobe along the pre-central gyrus, and S1 is located in the anterior parietal lobe along the post-central gyrus. The representation of the mouth and lips in M1 and S1 is on the lateral portion of these gyri. Most of M1 and S1 are less than about 5 millimeters (mm) under the skull. Some portions of M1 and S1 are in sulci and require deeper targeting up to about 3 centimeters (cm). The duration of the bioTU is chosen to be within a range between about 10 milliseconds to about 1 minute or longer. In some cases the bioTU protocol may be repeated several times with intervals chosen within a range of about 1 second to about 1 minute or longer.

The sender and recipient may be husband and wife separated by distance to communicate the subjective experience of touch to the lips and/or mouth. The husband (sender) wishes to "communicate" touch to the lips and mouth of his wife. He transmits a message to trigger the touch that is identified as originating from him. The message is sent to the bioTU device worn by his wife which activates the mouth and lip areas of M1, S1, or both via one or more ultrasound transducers. His wife's mouth may move as she perceives the subjective experience. She recognizes the touch is delivered from her husband and feels positive emotions related to her feelings for her husband.

Example 6

Communicate Somatosensory Input Via bioTU in a Mouse

In this example, bioTU is used to communicate sensory input to the whiskers of a mouse. The targeted brain region is somatosensory barrel cortex bilaterally. In mice, barrel cortex is about 1 to 2 mm posterior and about 3 to 4 mm lateral relative to bregma. The thin skull of the mouse facilitates targeting of this superficial location. The duration of the bioTU protocol is chosen to be within a range between about 10 milliseconds to about 5 seconds. In one embodiment of this example, a second mouse is placed in a separate cage and video tracking is used to determine when the right or left whiskers of the second mouse touch an object. This event is transmitted to the appropriate hemisphere of the recipient mouse.

In an example embodiment of the invention, the exploration of an object by one mouse is communicated to another mouse by delivering transcranial ultrasound (bioTU) to the barrel cortex of a mouse. Mouse barrel cortex is the sensory cortex that receives thalamic inputs related to touch by the whiskers. Electrical and optogenetic stimulation studies have previously shown that direct activation of the barrel cortex can be used to simulate the mouse's exploration of the environment. Another application of barrel cortex stimulation previously reported is as an associative stimulus for a training paradigm. In this framework, a mouse can be trained to assign a particular response (such as a lever press or limb movement) with barrel cortex stimulation on the left or right side of the brain. Barrel cortex represents sensation by the contralateral whiskers, so stimulation of this brain region is thought to produce a subjective experience similar to—or, at minimum, can successfully serve as a cue in a training paradigm for—actual whisker activation.

Before the bioTU brain stimulation procedure begins, a mouse is implanted with a post for head fixation in a training apparatus that includes a styrofoam ball that can freely rotate due to its being supported by pressurized air. In some embodiments, an alternative head fixation system can be used. After recovery from surgery the mouse is habituated to head fixation on the ball system, then trained to run in response to stimulation of the whiskers delivered by a pair of electrodes fixed in the whisker pad area. Alternatively, the whiskers can be stimulated mechanically with a robotic arm or similar.

In the first step of training, a reward (chocolate milk or other positive reinforcing stimulus) is provided when the mouse runs spontaneously. In a subsequent step of training, the right whiskers are stimulated when the mouse begins to run in order to associate the stimulus with both running and activation of the whiskers. After several days of training in each of the preceding two regimes, reward is only delivered if the mouse runs in response to the whisker stimulation. The mouse continues to be trained in this manner until it reaches criterion performance.

A second mouse is placed in a separate, sound-proof training arena that is made of impermeable partitions resting on a Plexiglas infrared emitting base. Behavior is recorded by an infrared-sensitive camera placed directly above the arena to enable studies in the light or in the dark. Data are stored and analyzed using automated video processing software such as Videotrack software from ViewPoint (Montreal, Canada). A single small object (e.g. salt shaker) is placed in the middle of the training arena. When the mouse touches it with either its left or right whiskers, the corresponding region of (contralateral) barrel cortex in the trained, headfixed mouse is stimulated via bioTU. In this manner, the mouse exploring the object communicates to the trained, headfixed mouse the nature of its object exploration. In this example, neither mouse is aware that the other is sending—or receiving—a message.

Example 7

Ultrasound Neuromodulation for Immersive Gaming

In this example, bioTU is used to communicate sensory input related to somatosensory, visual, auditory, or vestibular perception. For each sensory modality, the appropriate area of sensory cortex is targeted.

Video games continue to evolve to provide a more realistic experience for the player. In addition to increasingly realistic graphics and sounds, techniques for interacting with other sensory modalities have been developed. For instance, some gaming systems offer handheld controllers, steering wheels for driving games, or other controller hardware that touch the user and vibrate at opportune times during the gaming experience. In a driving game, the steering wheel vibrates when the player crashes his car. In a football or boxing game, the handheld controller vibrates when the character controlled by the user is tackled or punched. These devices enhance the gaming experience by engaging sensory domains other than visual and auditory. Techniques to further extend the immersion of the gaming experience are desired.

In one of many potential examples of immersive gaming using bioTU, haptic stimuli delivered through, for instance, handheld controllers are replaced by direct activation of somatosensory brain regions. In one example embodiment, the game is a karate-style game in which the gamer fights an opponent controlled by another player or the gaming system. The gamer wears a bioTU helmet or other hardware attachment with ultrasound transducers targeting primary sensory cortex. It is well known that primary sensory cortex has a somatotopic arrangement extending from the ventromedial to posterolateral portions of cortex immediately posterior to the central sulcus. The array of ultrasound transducers target different portions of somatosensory cortex based on their positioning. During the course of game play, different portions of somatosensory cortex are activated by bioTU when the gamer's character is punched or kicked in that body area. The gamer feels the force of the impact directly and enjoys a more immersive gaming experience.

In another embodiment, one ultrasound transducer is held in place above sensory cortex on each side of the head with a headband. The headband may be connected to headphones to deliver auditory stimuli. In one example embodiment, bioTU is used in a first person shooter style 'Zombie' game. The ultrasound transducers are activated on one side of the head to indicate that a threat is present to that side of the player, requiring the gamer to turn in that direction to shoot a computer generated Zombie or one controlled by an opponent. bioTU can also be used to indicate that the gamer's character has been wounded on that side of the body. After wounding, intermittent bioTU delivered to the gamer could serve as a distracting stimulus representative in the context of the game as reduced strength or the presence of an injury.

In another embodiment, bioTU stimulation targeting vestibular cortex can be used to induce the feeling of balance changes for any game with fast motion (skiing, racing, football, etc). A similar application could also be used in a shooter game (i.e. the player feels a quick shift in balance after he has been shot or injured). In yet another embodiment, bioTU is targeted to the visual cortex to communicate a visual sensory experience when the character controlled by the gamer is injured or walks from a dark to light room in the gaming environment. In yet another embodiment, bioTU can be used to activate auditory cortex to communicate an instruction to the gamer relevant to the gaming experience.

Example 8

Ultrasound Neuromodulation in a Movie Theater During a Horror Movie

In this example, bioTU is used to communicate sensory experiences or alterations in cognitive state to an individual attending a movie.

Moviegoers enjoy immersive entertainment experiences. In recent years, the movie-going experience has been enhanced by higher definition projection systems, surround-sound speaker systems, IMAX theaters, and three-dimensional (3D) movies. One way to further enhance movies can be achieved by delivering ultrasound neuromodulation to one or more brain regions during pre-determined moments during the movie.

In this example embodiment, an individual attending a movie receives a bioTU neuromodulation device when they enter the theater. The bioTU device is placed on the head and may take the form of a cap, helmet, or headband. The bioTU device includes one or more ultrasound transducers, controller hardware and software to drive the transducers with the appropriate time-varying patterns of ultrasound, and a mechanism to receive instructions for what bioTU stimulus to deliver and when to trigger it.

In one embodiment, the bioTU device may plug into the seat for power and to connect to the theater system to receive bioTU stimulation parameters and a triggering signal for delivering bioTU. In another embodiment, the bioTU device contains a battery and communicates wirelessly to a transmitter placed in the theater for communicating the type and timing of bioTU stimulation. For instance, the instructions for bioTU delivered by the theater controls may determine which of several bioTU transducers wearably attached to a moviegoer are activated during a particular epoch of the movie.

Moviegoers are leant hardware as they enter the theater, similar to how 3D glasses are distributed upon entering a 3D movie. The moviegoer puts on the bioTU device before the movie begins. The bioTU device is designed to target one or more brain regions. For instance, the bioTU device may be worn over the head like a headband and contain ultrasound transducers targeting somatosensory cortex or areas of prefrontal cortex that relate to emotion in the cingulate cortex.

The team of individuals who filmed and edited the movie will define times during the movie when bioTU is delivered to the audience. In one embodiment, during a horror movie a bioTU stimulus is delivered that targets somatosensory cortex of the left side of the body when a villain unknowingly approaches. The moviegoer is startled and thus experiences a more immersive experience. In another embodiment, bioTU is targeted to a brain region that, when activated, leads to a feeling of love and connectedness by activating oxytocin circuitry. In yet another embodiment, bioTU targeted to brain regions that increase physiological arousal is used to excite the moviegoer during a suspenseful scene. In alternative embodiments, a plurality of potential targets can be used to communicate sensory experiences or alterations in cognitive state that accordingly affect the moviegoer's entertainment experience.

Example 9

Communication of Movement, Acceleration, Rotation, or Tilt for Pilot Training

In this example, bioTU is used to communicate movements that would be experienced by a pilot or astronaut in order to create a more realistic training environment. The targeted brain regions are chosen from vestibular cortical regions such as the temporal-parietal junction, central sulcus, intraparietal sulcus, and insular cortex. In man, these regions are located at varying depths from the surface of the skull and thus would be amenable to targeting with bioTU. The duration of the bioTU is chosen to be within a range between about 10 milliseconds to about 5 seconds. In some cases the bioTU protocol may be repeated several times with intervals chosen within a range of about 1 second to about 1 minute or longer.

Flight simulators are a common tool for training pilots, astronauts, or other operators of complex mechanical equipment. Designers of flight simulators go to great lengths to create a simulated experience that is realistic. Equipment panels are similar or identical to actual cockpit controls, visual displays present external visual cues of the flying environment or runway, and the dynamics of controlling the simulated airplane are made to approximate those of the actual airplane.

Despite the best efforts of simulator designers, the simulated flying experience differs from the true experience of flying in important ways. For instance, simulators cannot fully re-create the subjective perceptions of acceleration, tilt, yaw, rotation, and gravitational (g) forces. Although some flight simulators are mounted on hydraulic lifts for shifting the orientation of the simulator, these movements lack realism and reduce the efficacy of training, particularly for high performance jets or spaceships that encounter intense acceleration and g-forces. Devices and methods for further enhancing the realism of pilot training would be advantageous.

In one example embodiment, g-forces, forward acceleration, and various rotations are communicated directly to the training pilot by bioTU. In this respect, bioTU is used as an alternative to galvanic vestibular stimulation. The design of the simulator includes development of software for translating movements of the simulated plane into bioTU stimulation parameters that approximately re-create the experience of the pilot's body moving through space. In one embodiment of this example device, each pilot is pre-screened to determine the parameters of bioTU stimulation necessary to evoke a particular subjective experience of acceleration, rotation, and g-forces.

At the beginning of the simulator training session, bioTU transducers are mounted in the pilot's helmet. The ultrasound transducers are targeted to activate vestibular pathways that represent tilt, yaw, rotation, and forward acceleration and other brain regions that underlie the subjective experience of piloting an aircraft. During the training exercise, the pilot uses the flight controls to move the simulated plane. The simulator calculates the vestibular movements of the simulated plane based on the pilot's control inputs and delivers a pattern of bioTU stimulation via one or more transducers to re-create the subjective experience of the pilot.

Example 10

Communication of Mirth and Laughter

In this example, bioTU is used to communicate positive emotional affect related to subjective experiences of happiness that include the feeling of mirth and the motor behavior of laughter. One or more brain regions shown to be related to these cognitive states are targeted by bioTU. Advantageous targets include the inferior temporal gyrus, cingulate gyrus, and subthalamic nucleus. The duration of the bioTU is chosen to be within a range between about 100 milliseconds and about 5 seconds. To achieve an extended period of mirth and laughter, the bioTU protocol may be repeated several times with intervals chosen within a range of about 1 second to about 1 hour or longer.

Data from invasive electrical stimulation studies in patients undergoing monitoring for intractable seizures indicate that distinct brain regions underlie the emotional and motor aspects of mirth and laughter. The motor aspects of a positive affect such as smiling and laughter—but not feelings of mirth—were induced by electrical stimulation in the left cingulate gyrus (Sperli et al., 2006). At low stimulation intensities, stimulation in the inferior temporal gyrus in another patient induced mirth without laughter (Satow et al., 2003). However, both mirth and laughter were elicited by stimulation in the inferior temporal gyrus higher stimulation intensities (Satow et al., 2003) and, in another patient, electrical stimulation targeting the cingulate gyrus (Arroyo et al., 1993). These findings confirm that the emotional and motor centers underlying positive affect are functionally connected.

A bioTU protocol designed to communicate the feelings of happiness and/or mirth concurrently with the motor response of laughter could employ alternative embodiments. In one embodiment, a single ultrasound transducer targets either the inferior temporal gyrus or the cingulate gyrus (unilaterally or bilaterally) and a bioTU protocol that strongly activates the underlying cortical region is used to induce emotional and motor responses. In an alternative embodiment, two ultrasound transducers deliver bioTU protocols targeted to the inferior temporal gyrus and the right cingulate gyrus to induce the emotional and motor aspects of mirth and laughter, respectively. For some individuals, embodiments of a communication system for laughter and mirth may use alternative targets such as the subthalamic nucleus.

bioTU targeted to one or more of the brain regions described in this example can be used to communicate an emotional message of happiness, mirth, and laughter from a sender to a recipient. The sender may be a friend or loved-one of the recipient who wishes to make the recipient feel happy. For instance, the message of happiness may accompany an amusing picture of a loved one, a joke, or a description of an enjoyable shared experience. The message is transmitted to a bioTU device wearably attached to the recipient that induces one or both of motor (laughter) and emotional (mirth) aspects of the subjective experience of extreme happiness and positive affect in the recipient.

In other embodiments of a system for communicating subjective feelings of happiness via bioTU, the recipient may be an individual who is depressed or who has recently experienced a sad event such as the death of a loved-one or who has a pathological inability to experience happiness (anhedonia). In each of these embodiments, a friend, doctor, psychiatrist, or other caretaker communicates the subjective feeling of happiness to the recipient that they would otherwise be unlikely or unable to experience.

Example 11

Communicate a Feeling of Fear

In this example, bioTU is used to communicate the subjective experience of fear. One or more brain regions shown to be related to the experience of fear are targeted by bioTU. Advantageous targets include the amygdala, insular cortex, internal capsule, nucleus accumbens, and anterior temporal gyrus. The duration of the bioTU is chosen to be within a range between about 100 milliseconds and about 5 seconds. To achieve an extended period of fear, the bioTU protocol may be repeated several times with intervals chosen within a range of about 1 second to about 1 hour or longer.

Electrical stimulation of several brain regions has been associated with states of fear in humans. Stimulation of the insular cortex—particularly the posterior insular cortex—induces an experience of pain in subjects undergoing presurgical evaluation of epilepsy via depth electrodes. Other brain regions for which stimulation has been reported to induce fear in a subject include the internal capsule and nucleus accumbens region, the anterior temporal gyrus, amygdala, and lateral temporal neocortex. The amygdala is a particularly advantageous target for communicating a message of fear due to its well-known role in social processing, emotional memory, and stress responses.

In various embodiments of a system to communicate a message that induces a feeling of fear in the recipient, one or more of the several fear-related brain regions described in this example may be targeted with bioTU. Moreover, in some embodiments, variation between individuals in the brain circuits underlying the processing of fear may require a beneficial feature in which alternative targeting configurations are tested combinatorically to determine which brain regions achieve the desired fearful response most effectively.

bioTU targeted to one or more of the brain regions described in this example can be used to communicate an emotional message of fear from a sender to a recipient. The message is transmitted to a bioTU device wearably attached to the recipient that induces a subjective experience of fear. A communication for inducing a subjective feeling of fear has various beneficial applications. One embodiment of a system for communicating the subjective feeling of fear would be used for training first responders, military personnel, intelligence agents, or individuals in similar contexts that require acting in a skilled manner despite the presence of fear. The recipients who are being trained receive a more realistic training experience due to the realistic subjective experience of fear.

Other applications for communication of fear are advantageous for entertainment. Fear-inducing entertainment experiences are often enjoyable and include theme parks rides, haunted houses, and scary movies. The fearfulness of these experiences can be enhanced via bioTU-mediated communication of fear to attendees of such events.

Example 12

Communication of an Emotional Attachment to Another (Pair Bonding)

In this example, bioTU is used by a pair or group of individuals to communicate an emotional connection or strong mutual attachment that may be referred to as a 'pair bond'. One or more brain regions are targeted that play a role in emotional processing and/or pair-bonding. Pair-bonding circuitry is known to involve the neuropeptide oxytocin. In man, important aspects of brain circuits related to emotional processing and oxytocin include the amygdala, hypothalamus, anterior cingulate cortex, hippocampus, nucleus accumbens, and suprachiasmatic nucleus. These regions are at deep locations in the brain and thus amenable to targeting with bioTU for neuromodulation. The duration of the bioTU for communicating an emotional connection or pair bond is chosen to be within a range between about 10 milliseconds and about 5 seconds. In some cases the bioTU protocol may be repeated several times with intervals chosen within a range of about 1 second to about 1 hour or longer.

Communication of emotions related to a strong bond with another for instance between a husband and a wife, parent and child, or good friends can be achieved through spoken or written language, posture, facial expressions, touch, or other means. In our modern world relationships are often defined by remote, Internet-based interactions. Improved mechanisms for engaging social-processing, emotional-processing, and/or oxytocin-related circuitry to enhance pair bonding would be desired to improve the quantity and quality of interpersonal relationships.

A communication system related to enhanced pair bonding or emotional connections can take many forms. The message to enhance pair-bonding circuitry from one or more senders is transmitted to a bioTU device wearably attached to the recipient that induces neuromodulation of oxytocin or other emotional processing brain circuits in the recipient. Beneficial embodiments of a communication system between two or more individuals based on bioTU neuromodulation directed to one or more of the brain regions enumerated in this example can take several forms.

A husband and wife may renew their emotional connection by communicating via bioTU an enhancement of the brain circuitry underlying emotional attachment. This embodiment is similar in some respects to the couple renewing their vows.

Two individuals on a dating site may agree to each receive a communicated enhancement of oxytocin circuitry before their first date.

A psychiatrist, counselor, detective, or other individual who requires high acuity for processing social cues could receive a communicated enhancement of oxytocin circuitry automatically based on the physiological state of one or more individuals they are observing.

A mother suffering from post-partum depression—or emotionally distant father—receives a bioTU-mediated enhancement of oxytocin circuitry to ensure an appropriately strong parent-child bond is formed.

Or numerous other embodiments in which a strong personal connection is desired between one or more individuals.

Example 13

Communicate a Modulation of Risk-Taking Behavior

In this example, bioTU is used to communicate a modification of risk-taking behavior. The targeted brain region is dorsolateral prefrontal cortex, a brain region readily accessed via bioTU. The duration of the bioTU is chosen to be within a range between about 10 milliseconds and about 5 seconds. In some cases the bioTU protocol may be repeated several times with intervals chosen within a range of about 1 second to about 1 hour or longer.

Prefrontal cortex is the seat of executive control and decision-making. Risk is a fundamental component of decision-making behavior and regions of prefrontal cortex are thought to contribute to risk assessment and the role risk plays in decision-making. Repetitive transcranial magnetic stimulation (rTMS) and transcranial direct current stimulation (tDCS) studies directed to dorsolateral prefrontal cortex have identified lateralization of structures involved in modulating risk. Data indicate that neurostimulation that increases the relative activity in left dorsolateral prefrontal cortex increases risk-taking behavior, while neurostimulation that increases the relative activity in right dorsolateral prefrontal cortex decreases risk-taking behavior. bioTU is an advantageous brain stimulation technology for modulating risk-taking behavior due to the flexibility and richness of stimulation parameters for causing activation, inhibition, or modulation of neural circuit activity and its capacity for specific targeting to left and right dorsolateral prefrontal cortex. In this manner, risk-taking behavior can be increased, decreased, or otherwise adjusted in a titrated manner.

A communication system related to modulating risk-taking behavior can take many forms. The message to modulate risk-taking may be a message to increase risk-taking behavior, reduce risk-taking behavior, or maintain risk-taking within a specified range. The message is transmitted to a bioTU device wearably attached to the recipient that induces neuromodulation of left and/or right dorsolateral prefrontal cortex. The communication system for modulating risk-taking behavior via bioTU can take one of several forms:

Employers may modulate the risk-taking behavior of traders in financial markets based on market forces, the current portfolio of the recipient (trader), or other metrics so that the trader chooses positions with an acceptable risk profile.

Pilots, bus drivers, train drivers, and other operators of heavy equipment could receive communication to reduce risk-taking behavior via an automated system based on their physiological state, machine state, or other environmental or contextual factor.

Parole officers, psychiatrists, counselors, doctors, alcoholics anonymous sponsors, parents, or another individual who seeks to reduce risk-seeking behavior in another individual may send a message to modify risk-taking behavior to an at-risk recipient such as a parolee, psychiatric patient, addict, child, or other at-risk individual.

Example 14

Communicate a Relaxed State by Enhancing Alpha Rhythms

In this example, bioTU is used to communicate an enhancement of alpha rhythms. The targeted brain region is the occipital lobe. The duration of the bioTU is chosen to be within a range between about 10 milliseconds and about 5 seconds. In some cases the bioTU protocol may be repeated several times with intervals chosen within a range of about 1 second to about 1 hour or longer.

Alpha rhythms (alternately referred to as alpha waves) are 8-12 Hz oscillations thought to originate in the thalamus or occipital lobe. Alpha rhythms can be readily recorded by electroencephalography (EEG). Although EEG recordings in wide areas of the brain can detect alpha rhythms, peak power in this frequency band is found in the occipital lobe. Recently, transcranial alternating current stimulation (tACS) delivered to the occipital lobe was shown to enhance alpha rhythms in humans (Zaehle et al., 2010).

bioTU is a promising alternative for enhancing alpha rhythms due to its improved focusing capacity and the painlessness of delivery. In this example, bioTU is used to communicate a state of quiet, wakeful relaxation to the recipient. The communication of enhanced alpha rhythms can be useful for reducing stress, enhancing a meditative state, or reducing obsessive compulsive behavior. The sender of the alpha rhythm-enhancing message may be a counselor, psychiatrist, friend, loved one, yoga teacher, meditative tutor, doctor, or other individual who wishes to provide a state of relaxation and reduced stress to the recipient. The message to enhance the recipient's alpha rhythms is transmitted to a bioTU device wearably attached to the recipient that induces enhanced alpha rhythms in the recipient.

Example 15

Communicate a State of High Attention and Mental Acuity by Enhancing Gamma Rhythms In this example, bioTU is used to communicate an enhancement of gamma rhythms. bioTU is targeted to one or more regions of cerebral cortex that may include sensory cortex, motor cortex, association cortex, frontal cortex, or another region of cortex. The duration of the bioTU is chosen to be within a range between about 10 milliseconds and about 5 seconds. In some cases the bioTU protocol may be repeated several times with intervals chosen within a range of about 1 second to about 1 minute or longer.

Gamma rhythms (alternately referred to as gamma waves) are oscillations in the range of frequencies between about 25 Hz and about 40 Hz. In some cases, the upper range for gamma rhythms is higher, up to about 80 Hz or higher frequencies. Gamma rhythms are thought to be associated with perception, consciousness, and higher mental activity. Gamma rhythms can occur in various cortical regions and may play a role in binding of activity across brain regions, a process whereby cognitive processes occurring in parallel in various cognitive domains are linked in a conscious or subconscious manner.

Recently, transcranial alternating current stimulation (tACS) at gamma rhythm frequencies was shown to induce haptic sensations when delivered to primary somatosensory cortex (Feurra et al., 2011). bioTU for communication of an enhancement of gamma rhythms is advantageous due to the potential for targeting many regions of cerebral cortex in parallel to engage gamma rhythm-sensitive processes in discrete brain regions for the purpose of binding them together.

The communication of enhanced gamma rhythms can be useful for increasing attention and mental acuity. The sender of the gamma rhythm-enhancing message may be a teacher, tutor, parent, friend, loved one, employer, boss, or other individual who wishes to provide a state of attention and higher mental acuity to the recipient. The message to enhance the recipient's gamma rhythms is transmitted to a bioTU device wearably attached to the recipient that induces enhanced gamma rhythms in the recipient at one or more targeted brain regions.

Example 16

Specific Embodiments of bioTU Syntax for Communication

One or more ultrasound transducers having a center frequency of 0.5 MHz is coupled to the head of an individual using acoustic coupling gel or a silicon coupling puck. The center frequency of the transducers may be 0.5 MHz or 0.25 MHz or any combination of ultrasonic frequencies above 0.03 MHz and below 2 MHz.

Ultrasound transducers may be focused or unfocused. The transducer or transducer may be positioned over one or more areas of the head of an individual. For example, in one embodiment one ultrasound transducer is positioned on the head over the right motor cortex and one transducer is positioned on the head over the left dorsolateral prefrontal cortex.

Any one of several strategies may be used to identify the cortical areas to be targeted. For example, in one embodiment the motor cortex may be identified using transcranial magnetic stimulation (TMS) to identify the hand knob region of motor cortex identified as the region directly underneath a TMS coil at a position that most robustly activates hand muscles such as the first dorsal interosseous. In other embodiments, structural magnetic resonance imaging data from a subject may be used to identify regions of the cortex.

Communication using ultrasound transducers directly coupled to the head of a subject is accomplished by using any one of several approaches whereby ultrasound having distinct waveform parameters is transmitted through the skull of a user as described above. In one embodiment for example, transmission of ultrasound through the skull from a transducer coupled to the head of a user from a location positioned over the right motor cortex may be used to communicate directions to the user conveying a "go" signal thereby informing the user to engage in a behavioral action such as to press a button. In the same embodiment, transmission of ultrasound through the skull from a transducer coupled to the head of a user from a location positioned over the left dorsolateral prefrontal cortex of the user may be used to communicate directions to the user conveying a "no-go" signal thereby informing the user to "stop" a behavioral action such as to stop pressing a button. In such an embodiment the same ultrasound waveform for example having a pulse duration of 200 microseconds repeated at a pulse repetition frequency of 100 Hz for a total duration of 0.5 seconds can be used to communicate the "go" or "no-go" direction. In this particular embodiment, the "go" or "no-go" direction is conveyed as a function of the region of the brain targeted with ultrasound whereby a right motor cortex target equals "go" and left dorsolateral prefrontal cortex equals "no-go".

In another embodiment, four ultrasound transducers are used positioned at four discrete locations over the user's head to target the right motor cortex (R M1), the left motor cortex (L M1), the right dorsolateral prefrontal cortex (R dlPFC), and the left dorsolateral prefrontal cortex (L dlPFC). In this embodiment a bioTU Syntax is provided which provides a hierarchy of communication commands as shown in the figure below where ultrasound transmitted through the skull directed to the R M1 communicates to the user a right hand go command, ultrasound transmitted through the skull directed to the L M1 communicates a left hand go command, ultrasound transmitted through the skull directed to the right dlPFC communicates to the user a right hand no-go command, and ultrasound transmitted to the left dlPFC communicates to the user a left hand no-go command as illustrated. These commands are communicated to the user to evoke a behavioral action such as pressing (go) or to stop pressing a button (no-go) with the hand as directed. The communication of commands is only experienced by the user of bioTU and cannot be experienced by nearby observers not having ultrasound transmitted through their skull.

In another embodiment, different ultrasound waveforms are used to communicate specific information through a single transducer positioned at one or more locations on the head as discrete ultrasound waveform profiles are targeted to one or more brain regions. For example, in one embodiment a bioTU Syntax is provided whereby a bioTU waveform composed of 0.5 MHz ultrasound having pulse durations of 200 microseconds delivered at a pulse repetition frequency of 100 Hz for 0.5 seconds delivered from a transducer positioned over the R M1 of a user communicates a "go" command to signal the pressing of a button. In the same embodiment the bioTU Syntax indicates a bioTU waveform composed of 0.5 MHz ultrasound having a pulse duration of 400 microseconds delivered at a pulse repetition frequency of 10 Hz for 1 second from a transducer at the same position over the R M1 of a user communicates a "no-go" command to signal the termination of button pressing.

As with any form of communication, the rules of the language are defined by a syntax. As such, bioTU can be used in various forms of complexity ranging from simple embodiments as described above to more complex embodiments depending on the syntax provided. In a more complex embodiment, communication between two bioTU users can be achieved whereby a user interface delivers a bioTU signal from one user to another user. In this example embodiment, one user may choose to communicate agreement or disagreement with another user or may wish to communicate the feeling or emotion of being happy or sad to another user. This is demonstrated in one example embodiment whereby one user implements an interface to deliver bioTU through transducers positioned over the other user's head in discrete locations such as M1 and dlPFC or a non-cortical brain region such as the amygdala. In this embodiment the bioTU Syntax indicates an ultrasound waveform (0.5 MHz, pulse duration of 200 microseconds, pulse repetition frequency of 200 Hz for 1 second) transmitted through the skull targeting R M1 to communicate "agreement", targeting of L M1 to communicate "disagreement", targeting of R dlPFC to communicate the feeling of being "happy", and targeting of L dlPFC to communicate the feeling of being "sad" as illustrated. In this embodiment one user can activate the interface to deliver a bioTU waveform from a transducer positioned over the R dlPFC of another user to communicate the feeling of being "happy" or to deliver a bioTU waveform from a transducer positioned over the L M1 of the other user to communicate "disagreement" with an answer to a question or choice.

In another complex embodiment, a commander or administrator may communicate commands to several users. In an example embodiment bioTU may be used to communicate navigational commands to a group of users. In this example embodiment, the bioTU Syntax provides for four discrete bioTU waveforms delivered from a single transducer positioned over the L dlPFC of users to communicate directions to walk forward (e.g. an ultrasound waveform with 0.5 MHz acoustic frequency, 0.2 millisecond pulse duration, 100 Hz pulse repetition frequency, and 1 second duration), walk backwards (e.g. an ultrasound waveform with 0.5 MHz acoustic frequency, 0.5 millisecond pulse duration, 10 Hz pulse repetition frequency, and 1 second duration), turn right (e.g. an ultrasound waveform with 0.5 MHz acoustic frequency, 0.2 millisecond pulse duration, 500 Hz pulse repetition frequency, and 1 second duration), or turn left (e.g. an ultrasound waveform with 0.5 MHz acoustic frequency, 0.2 millisecond pulse duration, 1000 Hz pulse repetition frequency, and 0.5 second duration). In another example embodiment as illustrated, bioTU may be used to provide navigational commands by monitoring users' positions from sensors or global positioning satellites to provide navigational assistance by communicating directional commands to navigate to a destination or goal position.

In some embodiments, a bioTU Syntax component of the system is configured to vary multiple ultrasound parameters between two messages so that the recipient can distinguish them more easily. In other embodiments, a bioTU Syntax component of the system is configured to vary only a single ultrasound parameter between two messages in order to increase the bandwidth of communication or the number of unique messages that can be transmitted with a fixed number or arrangement of transducers or transducer arrays.

Besides providing descriptions of bioTU Syntax to describe various aspects of the bioTU language communicated by transcranial transmission of ultrasound having discrete waveform parameters or targeting different brain regions or any combination of waveform and brain target, several features of user interfaces are required. Methods for enabling users to select bioTU waveforms are accomplished through a user interface having several buttons or whereby selections can be made through a touchscreen interface on a control box.

BioTU user interfaces used for communication may be comprised of a headband to position and hold transducers in place over selected head locations to target specific brain targets, such as dlPFC or M1.

Methods enabling users to define his/her own bioTU Syntax are provided whereby users may operationally define the meaning of a particular bioTU waveform or the meaning of a bioTU waveform targeting a particular location. In this embodiment, users can select from any number of a predetermined set of available bioTU waveforms and set the meaning of that waveform using a U+ or bioTU user interface connected to a computer or other input device such as a smartphone or tablet through a hard wire such as a FireWire cable or USB cable or wirelessly using WiFi, WiMax, IR, RF, Bluetooth, or other method of transmitting and receiving data between devices. In another embodiment, users may synthesize their own bioTU waveforms, as well as operationally define the meaning of that waveform for communication purposes. In some embodiments, a system can be configured to offer users an option to 'upgrade' to make additional bioTU waveforms available for them to define and use in communication with another user.

In the above embodiments, bioTU or U+ may be used to communicate concepts, ideas, emotions, commands, directions, or for any other purpose routine methods of communication are presently used.

What is claimed is:

1. A method for communicating information to an individual, said method comprising:
   translating the information into a series of ultrasound pulses for transmission to one or more target locations of a brain of the individual; and
   directing the series of ultrasound pulses to the one or more target locations of the brain through a cranium of the individual to produce a cognitive effect which the individual perceives as the information.

2. The method of claim 1, wherein the acoustic energy is directed at a target region in the brain to cause a selected cognitive effect.

3. The method of claim 2, wherein the target region and cognitive effect are selected from the group consisting of:

| Cognitive effect | Target region |
| --- | --- |
| Perception of touch | Somatosensory cortex |
| Auditory perception | Auditory cortex |
| Vestibular perception | Temporal-parietal junction, central sulcus, intraparietal sulcus, and insular cortex |
| Visual perception | Primary and extrastriate visual cortex |
| Olfactory perception | Piriform cortex |
| Language comprehension | Wernicke's area |
| Language production | Broca's area |
| Long-term memory | Hippocampus and parahippocampal formation (and connected portions of cortex, e.g. entorhinal cortex and perirhinal cortex) |
| Modulation of pain processing | Rostral anterior cingulate cortex |
| Emotion | Limbic system (e.g. amygdala) |
| Motor control and movements | Primary and supplementary motor cortex; thalamus; cerebellum; basal ganglia; substantia nigra |
| Attention | Gamma rhythms |
| Relaxation | Alpha rhythms |
| Empathy, social interaction | Brainstem nuclei, hypothalamus, amygdala, anterior cingulated cortex, prefrontal cortex, ventromedial prefrontal cortex, and other brain regions involved in oxytocin and arginine vasopressin function |
| Mirth and laughter | Inferior temporal gyrus, cingulated gyrus, subthalamic nucleus |
| Fear | Amygdala, insular cortex, internal capsule, nucleus accumbens, and anterior temporal gyrus |
| Physiological arousal, sleep state | Various brainstem nuclei |
| Modulation of risk taking | Dorsolateral prefrontal cortex. |

4. The method of claim 3, wherein modulating comprises at least one of:
   (a) controlling the duration of the cognitive effect which is perceived by the individual;
   (b) generating a series of off and on pulses of the cognitive effect which are perceived as a code by the individual
   (c) directing the ultrasonic energy to different target regions to produce a perceptible pattern of different cognitive effects; and
   (d) controlling the intensity of the cognitive effect in a perceptible pattern.

5. The method of claim 1, wherein the acoustic energy has a frequency in a range between 100 kHz and 10 MHz.

6. The method of claim 1 wherein the acoustic energy has a spatial-peak, temporal-average intensity in brain tissue in a range from 0.0001 mW/cm$^2$ to 1 W/cm$^2$.

7. The method of claim 6, wherein the spatial-peak, temporal-average intensity in brain tissue is modulated to encode the information.

8. The method of claim 1, wherein the heating of brain tissue at the target location is no more than 2 degrees Celsius for no more than 5 seconds.

9. The method of claim 1, wherein the pulse length in a range between 0.5 microsecond and 5 seconds.

10. The method of claim 9, wherein the pulse length is modulated.

11. The method of claim 1, wherein the pulse repetition frequency is in a range between 50 Hz and 25 kHz.

12. A system for communicating information to an individual, said system comprising:
    means for translating the information into a series of ultrasound pulses for transmission to one or more target locations of the individual's brain;
    means for directing acoustic energy to the one or more target locations of the individual's brain through the individual's cranium to produce a cognitive effect; and
    means for modulating the acoustic energy to encode the information transmitted to the one or more target locations with the series of ultrasound pulses, wherein the information is perceptible to the individual through variations in the cognitive effect.

13. The system of claim 12, wherein the acoustic energy is directed at a target region in the brain to cause a selected cognitive effect.

14. The system as of claim 13, wherein the target region and cognitive effect are selected from the group consisting of:

| Cognitive effect | Target region |
| --- | --- |
| Perception of touch | Somatosensory cortex |
| Auditory perception | Auditory cortex |
| Vestibular perception | Temporal-parietal junction, central sulcus, intraparietal sulcus, and insular cortex |
| Visual perception | Primary and extrastriate visual cortex |
| Olfactory perception | Piriform cortex |
| Language comprehension | Wernicke's area |
| Language production | Broca's area |
| Long-term memory | Hippocampus and parahippocampal formation (and connected portions of cortex, e.g. entorhinal cortex and perirhinal cortex) |
| Modulation of pain processing | Rostral anterior cingulate cortex |
| Emotion | Limbic system (e.g. amygdala) |
| Motor control and movements | Primary and supplementary motor cortex; thalamus; cerebellum; basal ganglia; substantia nigra |
| Attention | Gamma rhythms |
| Relaxation | Alpha rhythms |
| Empathy, social interaction | Brainstem nuclei, hypothalamus, amygdala, anterior cingulated cortex, prefrontal cortex, ventromedial prefrontal cortex, and other brain regions involved in oxytocin and arginine vasopressin function |
| Mirth and laughter | Inferior temporal gyrus, cingulated gyrus, subthalamic nucleus |
| Fear | Amygdala, insular cortex, internal capsule, nucleus accumbens, and anterior temporal gyrus |
| Physiological arousal, sleep state | Various brainstem nuclei |
| Modulation of risk taking | Dorsolateral prefrontal cortex. |

15. The system of claim 14, wherein modulating comprises at least one of:
    (a) controlling the duration of the cognitive effect which is perceived by the individual;
    (b) generating a series of off and on pulses of the cognitive effect which are perceived as a code by the individual;
    (c) directing the ultrasonic energy to different target regions to produce a perceptible pattern of different cognitive effects; and
    (d) controlling the intensity of the cognitive effect in a perceptible pattern.

16. The system of claim 12, wherein the acoustic energy has a frequency in a range between about 100 kHZ and about 10 MHz.

17. The system of claim 12, wherein the acoustic energy has a spatial-peak, temporal-average intensity in brain tissue in a range from 0.0001 mW/cm2 to 1 W/cm2.

18. The system of claim 17, wherein the spatial-peak, temporal-average intensity in brain tissue is modulated to encode the information.

19. The system of claim 12, wherein the heating of brain tissue at the target location is no more than 2 degrees Celsius for no more than 5 seconds.

20. The system of claim 12, wherein the pulse length is in a range between 0.5 microsecond and 5 seconds.

21. The system of claim 20, wherein the pulse length is modulated during the bioTU protocol.

22. The system of claim 12, wherein the pulse repetition frequency is in a range between 50 Hz and 25 kHz.

23. The method of claim 1 whereby the communication protocol specifies one or more of the acoustic frequency, duration, intensity, pulse repetition frequency, number of cycles, or duty cycle of the ultrasound wave.

24. A system for communicating information to an individual, comprising:
    one or more ultrasound transducers;
    a processor coupled to the one or more ultrasound transducers, the processor comprising instructions to,
        translate the information into a series of ultrasound pulses to one or more target locations of a brain of the individual;
        direct the series of ultrasound pulses to the one or more target locations of the brain through a cranium of the individual to produce a cognitive effect which the individual perceives as the information.

25. The system of claim 24, whereby the one or more target locations of the brain are specified and targeted for brain stimulation as part of a communication protocol.

26. The method of claim 1, wherein the information comprises symbolic information.

27. The system of claim 12, wherein the information comprises symbolic information.

28. The system of claim 24, wherein the information comprises symbolic information.

* * * * *